United States Patent
Scheuermann et al.

(10) Patent No.: US 7,981,150 B2
(45) Date of Patent: Jul. 19, 2011

(54) ENDOPROSTHESIS WITH COATINGS

(75) Inventors: Torsten Scheuermann, Munich (DE);
Jan Weber, Maastricht (NL); Yixin Xu,
Newton, MA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 99 days.

(21) Appl. No.: 11/860,253

(22) Filed: Sep. 24, 2007

(65) Prior Publication Data
US 2008/0147177 A1    Jun. 19, 2008

Related U.S. Application Data

(60) Provisional application No. 60/857,849, filed on Nov. 9, 2006.

(51) Int. Cl.
*A61F 2/06* (2006.01)
*A61F 2/02* (2006.01)
(52) U.S. Cl. ........................................................ 623/1.39
(58) Field of Classification Search ............... 623/23.72, 623/23.73, 23.74, 23.75, 23.76
See application file for complete search history.

(56) References Cited

U.S. PATENT DOCUMENTS

| | | | |
|---|---|---|---|
| 3,751,283 A | 8/1973 | Dawson | |
| 3,758,396 A | 9/1973 | Vieth et al. | |
| 3,910,819 A | 10/1975 | Rembaum et al. | |
| 3,948,254 A | 4/1976 | Zaffaroni | |
| 3,952,334 A * | 4/1976 | Bokros et al. | 623/11.11 |
| 3,970,445 A | 7/1976 | Gale et al. | |
| 3,993,072 A | 11/1976 | Zaffaroni | |
| 4,044,404 A | 8/1977 | Martin et al. | |
| 4,101,984 A | 7/1978 | MacGregor | |
| 4,143,661 A | 3/1979 | LaForge et al. | |
| 4,202,055 A * | 5/1980 | Reiner et al. | 623/23.57 |
| 4,237,559 A | 12/1980 | Borom | |
| 4,308,868 A | 1/1982 | Jhabvala | |
| 4,321,311 A | 3/1982 | Strangman | |
| 4,330,891 A | 5/1982 | Branemark et al. | |
| 4,334,327 A | 6/1982 | Lyman et al. | |
| 4,401,546 A | 8/1983 | Nakamura et al. | |
| 4,407,695 A | 10/1983 | Deckman et al. | |
| 4,475,972 A | 10/1984 | Wong | |
| 4,565,744 A | 1/1986 | Walter et al. | |
| 4,585,652 A | 4/1986 | Miller et al. | |
| 4,655,771 A | 4/1987 | Wallsten | |
| 4,657,544 A | 4/1987 | Pinchuk | |
| 4,665,896 A | 5/1987 | LaForge et al. | |
| 4,705,502 A | 11/1987 | Patel | |
| 4,733,665 A | 3/1988 | Palmaz | |
| 4,738,740 A | 4/1988 | Pinchuk et al. | |

(Continued)

FOREIGN PATENT DOCUMENTS

AT    232704    3/2003
(Continued)

OTHER PUBLICATIONS

U.S. Appl. No. 11/752,735, filed May 23, 2007, Scheuermann et al.
(Continued)

*Primary Examiner* — Alvin J. Stewart
(74) *Attorney, Agent, or Firm* — Fish & Richardson P.C.

(57) ABSTRACT

An endoprosthesis such as a coronary stent includes a polymeric reservoir of drug and an over coating formed of ceramic or metal for controlling elution of drag from the reservoir.

22 Claims, 8 Drawing Sheets

U.S. PATENT DOCUMENTS

| | | | |
|---|---|---|---|
| 4,743,252 A | 5/1988 | Martin et al. | |
| 4,784,659 A | 11/1988 | Fleckenstein et al. | |
| 4,800,882 A | 1/1989 | Gianturco | |
| 4,842,505 A | 6/1989 | Annis et al. | |
| 4,886,062 A | 12/1989 | Wiktor | |
| 4,902,290 A | 2/1990 | Fleckenstein et al. | |
| 4,954,126 A | 9/1990 | Wallsten | |
| 4,976,692 A | 12/1990 | Atad | |
| 4,994,071 A | 2/1991 | MacGregor | |
| 5,061,275 A | 10/1991 | Wallsten et al. | |
| 5,061,914 A | 10/1991 | Busch et al. | |
| 5,073,365 A | 12/1991 | Katz et al. | |
| 5,091,205 A | 2/1992 | Fan | |
| 5,102,403 A | 4/1992 | Alt | |
| 5,120,322 A | 6/1992 | Davis et al. | |
| 5,125,971 A | 6/1992 | Nonami et al. | |
| 5,147,370 A | 9/1992 | McNamara et al. | |
| 5,163,958 A | 11/1992 | Pinchuk | |
| 5,171,607 A | 12/1992 | Cumbo | |
| 5,195,969 A | 3/1993 | Wang et al. | |
| 5,205,921 A | 4/1993 | Shirkanzadeh | |
| 5,219,611 A | 6/1993 | Giannelis et al. | |
| 5,232,444 A | 8/1993 | Just et al. | |
| 5,236,413 A | 8/1993 | Feiring | |
| 5,250,242 A | 10/1993 | Nishio et al. | |
| 5,270,086 A | 12/1993 | Hamlin | |
| 5,279,292 A | 1/1994 | Baumann et al. | |
| 5,290,585 A | 3/1994 | Elton | |
| 5,302,414 A | 4/1994 | Alkhimov et al. | |
| 5,304,121 A | 4/1994 | Sahatjian | |
| 5,314,453 A | 5/1994 | Jeutter | |
| 5,322,520 A * | 6/1994 | Milder | 604/265 |
| 5,326,354 A | 7/1994 | Kwarteng | |
| 5,348,553 A | 9/1994 | Whitney | |
| 5,366,504 A | 11/1994 | Andersen et al. | |
| 5,368,881 A | 11/1994 | Kelman et al. | |
| 5,378,146 A | 1/1995 | Sterrett | |
| 5,380,298 A | 1/1995 | Zabetakis et al. | |
| 5,383,935 A | 1/1995 | Shirkhanzadeh | |
| 5,397,307 A | 3/1995 | Goodin | |
| 5,405,367 A | 4/1995 | Schulman et al. | |
| 5,439,446 A | 8/1995 | Barry | |
| 5,443,496 A | 8/1995 | Schwartz et al. | |
| 5,447,724 A | 9/1995 | Helmus et al. | |
| 5,449,373 A | 9/1995 | Pinchasik et al. | |
| 5,449,382 A | 9/1995 | Dayton | |
| 5,464,450 A * | 11/1995 | Buscemi et al. | 623/1.2 |
| 5,464,650 A | 11/1995 | Berg et al. | |
| 5,474,797 A | 12/1995 | Sioshansi et al. | |
| 5,500,013 A | 3/1996 | Buscemi et al. | |
| 5,527,337 A | 6/1996 | Stack et al. | |
| 5,545,208 A * | 8/1996 | Wolff et al. | 623/1.22 |
| 5,549,664 A * | 8/1996 | Hirata et al. | 623/1.48 |
| 5,551,954 A | 9/1996 | Buscemi et al. | |
| 5,569,463 A | 10/1996 | Helmus et al. | |
| 5,578,075 A * | 11/1996 | Dayton | 623/1.15 |
| 5,587,507 A | 12/1996 | Kohn et al. | |
| 5,591,224 A | 1/1997 | Schwartz et al. | |
| 5,603,556 A | 2/1997 | Klink | |
| 5,605,696 A * | 2/1997 | Eury et al. | 424/423 |
| 5,607,463 A | 3/1997 | Schwartz et al. | |
| 5,607,467 A | 3/1997 | Froix | |
| 5,609,629 A | 3/1997 | Fearnot et al. | |
| 5,614,549 A | 3/1997 | Greenwald et al. | |
| 5,624,411 A | 4/1997 | Tuch | |
| 5,649,951 A | 7/1997 | Davidson | |
| 5,649,977 A | 7/1997 | Campbell | |
| 5,672,242 A | 9/1997 | Jen | |
| 5,674,192 A | 10/1997 | Sahatjian et al. | |
| 5,674,242 A | 10/1997 | Phan et al. | |
| 5,679,440 A | 10/1997 | Kubota | |
| 5,681,196 A | 10/1997 | Jin et al. | |
| 5,690,670 A * | 11/1997 | Davidson | 606/198 |
| 5,693,085 A | 12/1997 | Buirge et al. | |
| 5,693,928 A | 12/1997 | Egitto et al. | |
| 5,711,866 A | 1/1998 | Lashmore et al. | |
| 5,733,924 A | 3/1998 | Kanda et al. | |
| 5,733,925 A | 3/1998 | Kunz et al. | |
| 5,741,331 A | 4/1998 | Pinchuk | |
| 5,744,515 A | 4/1998 | Clapper | |
| 5,749,809 A | 5/1998 | Lin | |
| 5,758,562 A | 6/1998 | Thompson | |
| 5,761,775 A | 6/1998 | Legome et al. | |
| 5,769,883 A | 6/1998 | Buscemi et al. | |
| 5,772,864 A | 6/1998 | Moller et al. | |
| 5,776,184 A | 7/1998 | Tuch | |
| 5,780,807 A | 7/1998 | Saunders | |
| 5,788,687 A | 8/1998 | Batich et al. | |
| 5,788,979 A | 8/1998 | Alt et al. | |
| 5,795,626 A | 8/1998 | Gabel et al. | |
| 5,797,898 A | 8/1998 | Santini, Jr. et al. | |
| 5,807,407 A | 9/1998 | England et al. | |
| 5,817,046 A | 10/1998 | Glickman | |
| 5,824,045 A | 10/1998 | Alt | |
| 5,824,048 A * | 10/1998 | Tuch | 128/898 |
| 5,824,049 A | 10/1998 | Ragheb et al. | |
| 5,824,077 A | 10/1998 | Mayer | |
| 5,830,480 A | 11/1998 | Ducheyne et al. | |
| 5,837,313 A | 11/1998 | Ding et al. | |
| 5,843,089 A | 12/1998 | Sahatjian et al. | |
| 5,843,172 A | 12/1998 | Yan | |
| 5,852,088 A | 12/1998 | Dismukes et al. | |
| 5,858,556 A | 1/1999 | Eckert et al. | |
| 5,873,904 A * | 2/1999 | Ragheb et al. | 623/1.13 |
| 5,874,134 A | 2/1999 | Rao et al. | |
| 5,879,697 A | 3/1999 | Ding et al. | |
| 5,882,335 A | 3/1999 | Leone et al. | |
| 5,888,591 A | 3/1999 | Gleason et al. | |
| 5,891,108 A | 4/1999 | Leone et al. | |
| 5,891,192 A | 4/1999 | Murayama et al. | |
| 5,902,266 A | 5/1999 | Leone et al. | |
| 5,922,021 A | 7/1999 | Jang | |
| 5,928,247 A | 7/1999 | Barry et al. | |
| 5,951,881 A | 9/1999 | Rogers et al. | |
| 5,954,706 A | 9/1999 | Sahatjian | |
| 5,962,136 A | 10/1999 | Dewez et al. | |
| 5,968,091 A | 10/1999 | Pinchuk et al. | |
| 5,968,092 A | 10/1999 | Buscemi et al. | |
| 5,968,640 A | 10/1999 | Lubowitz et al. | |
| 5,972,027 A * | 10/1999 | Johnson | 623/1.42 |
| 5,977,204 A | 11/1999 | Boyan et al. | |
| 5,980,564 A | 11/1999 | Stinson | |
| 5,980,566 A * | 11/1999 | Alt et al. | 623/23.7 |
| 6,013,591 A | 1/2000 | Ying et al. | |
| 6,017,577 A | 1/2000 | Hostettler et al. | |
| 6,022,812 A | 2/2000 | Smith et al. | |
| 6,025,036 A | 2/2000 | McGill et al. | |
| 6,034,295 A | 3/2000 | Rehberg et al. | |
| 6,045,877 A | 4/2000 | Gleason et al. | |
| 6,063,101 A | 5/2000 | Jacobsen et al. | |
| 6,071,305 A | 6/2000 | Brown et al. | |
| 6,074,135 A | 6/2000 | Tapphorn et al. | |
| 6,096,070 A | 8/2000 | Ragheb et al. | |
| 6,099,561 A * | 8/2000 | Alt | 623/1.44 |
| 6,099,562 A | 8/2000 | Ding et al. | |
| 6,106,473 A | 8/2000 | Violante et al. | |
| 6,120,536 A | 9/2000 | Ding et al. | |
| 6,120,660 A | 9/2000 | Chu et al. | |
| 6,122,564 A | 9/2000 | Koch et al. | |
| 6,139,573 A | 10/2000 | Sogard et al. | |
| 6,139,913 A | 10/2000 | Van Steenkiste et al. | |
| 6,153,252 A | 11/2000 | Hossainy et al. | |
| 6,156,435 A | 12/2000 | Gleason et al. | |
| 6,159,142 A | 12/2000 | Alt | |
| 6,171,609 B1 | 1/2001 | Kunz | |
| 6,174,329 B1 | 1/2001 | Callol et al. | |
| 6,174,330 B1 | 1/2001 | Stinson | |
| 6,180,184 B1 | 1/2001 | Gray et al. | |
| 6,187,037 B1 | 2/2001 | Satz | |
| 6,190,404 B1 | 2/2001 | Palmaz et al. | |
| 6,193,761 B1 | 2/2001 | Treacy | |
| 6,200,685 B1 | 3/2001 | Davidson | |
| 6,203,536 B1 | 3/2001 | Berg et al. | |
| 6,206,915 B1 | 3/2001 | Fagan et al. | |
| 6,206,916 B1 | 3/2001 | Furst | |
| 6,210,715 B1 | 4/2001 | Starling et al. | |
| 6,212,434 B1 * | 4/2001 | Scheiner et al. | 607/123 |

| | | |
|---|---|---|
| 6,212,607 B1 | 4/2001 | Scheiner et al. |
| 6,214,042 B1 | 4/2001 | Jacobsen et al. |
| 6,217,607 B1 * | 4/2001 | Alt ................. 623/1.1 |
| 6,231,600 B1 | 5/2001 | Zhong |
| 6,240,616 B1 | 6/2001 | Yan |
| 6,241,762 B1 | 6/2001 | Shanley |
| 6,245,104 B1 * | 6/2001 | Alt ................. 427/2.25 |
| 6,248,344 B1 * | 6/2001 | Ylanen et al. ................. 424/423 |
| 6,249,952 B1 | 6/2001 | Ding |
| 6,251,136 B1 | 6/2001 | Guruwaiya et al. |
| 6,253,443 B1 | 7/2001 | Johnson |
| 6,254,632 B1 | 7/2001 | Wu et al. |
| 6,270,831 B2 | 8/2001 | Kumar et al. |
| 6,273,908 B1 | 8/2001 | Ndondo-Lay |
| 6,273,913 B1 | 8/2001 | Wright et al. |
| 6,280,411 B1 | 8/2001 | Lennox |
| 6,283,386 B1 | 9/2001 | Van Steenkiste et al. |
| 6,284,305 B1 | 9/2001 | Ding et al. |
| 6,287,331 B1 | 9/2001 | Heath |
| 6,287,332 B1 | 9/2001 | Bolz et al. |
| 6,287,628 B1 | 9/2001 | Hossainy et al. |
| 6,290,721 B1 | 9/2001 | Heath |
| 6,299,604 B1 | 10/2001 | Ragheb et al. |
| 6,306,144 B1 | 10/2001 | Sydney et al. |
| 6,315,708 B1 | 11/2001 | Salmon et al. |
| 6,315,794 B1 | 11/2001 | Richter |
| 6,323,146 B1 | 11/2001 | Pugh et al. |
| 6,325,825 B1 | 12/2001 | Kula et al. |
| 6,327,504 B1 | 12/2001 | Dolgin et al. |
| 6,331,330 B1 | 12/2001 | Choy et al. |
| 6,335,029 B1 | 1/2002 | Kamath et al. |
| 6,337,076 B1 | 1/2002 | Studin |
| 6,342,507 B1 | 1/2002 | Naicker et al. |
| 6,348,960 B1 | 2/2002 | Etori et al. |
| 6,358,532 B2 * | 3/2002 | Starling et al. ................. 424/489 |
| 6,358,556 B1 | 3/2002 | Ding et al. |
| 6,364,856 B1 | 4/2002 | Ding et al. |
| 6,367,412 B1 * | 4/2002 | Ramaswamy et al. ...... 118/723 I |
| 6,368,658 B1 * | 4/2002 | Schwarz et al. ................. 427/2.15 |
| 6,379,383 B1 | 4/2002 | Palmaz et al. |
| 6,387,121 B1 | 5/2002 | Alt |
| 6,387,124 B1 | 5/2002 | Buscemi et al. |
| 6,390,967 B1 | 5/2002 | Forman et al. |
| 6,391,052 B2 | 5/2002 | Bulrge et al. |
| 6,395,325 B1 | 5/2002 | Hedge et al. |
| 6,395,326 B1 | 5/2002 | Castro et al. |
| 6,398,806 B1 | 6/2002 | You |
| 6,413,271 B1 | 7/2002 | Hafeli et al. |
| 6,416,820 B1 | 7/2002 | Yamada et al. |
| 6,419,692 B1 * | 7/2002 | Yang et al. ................. 623/1.15 |
| 6,436,133 B1 | 8/2002 | Furst et al. |
| 6,440,503 B1 | 8/2002 | Merdan et al. |
| 6,458,153 B1 | 10/2002 | Bailey et al. |
| 6,465,052 B1 | 10/2002 | Wu |
| 6,468,304 B1 | 10/2002 | Dubois-Rande et al. |
| 6,471,721 B1 | 10/2002 | Dang |
| 6,471,980 B2 | 10/2002 | Sirhan et al. |
| 6,475,477 B1 | 11/2002 | Kohn et al. |
| 6,478,815 B1 | 11/2002 | Alt |
| 6,479,418 B2 * | 11/2002 | Li et al. ................. 501/81 |
| 6,488,715 B1 * | 12/2002 | Pope et al. ................. 623/22.21 |
| 6,491,666 B1 | 12/2002 | Santini, Jr. et al. |
| 6,491,720 B1 | 12/2002 | Vallana et al. |
| 6,503,921 B2 | 1/2003 | Naicker et al. |
| 6,504,292 B1 | 1/2003 | Choi et al. |
| 6,506,437 B1 | 1/2003 | Harish et al. |
| 6,506,972 B1 | 1/2003 | Wang |
| 6,514,283 B2 | 2/2003 | DiMatteo et al. |
| 6,514,289 B1 * | 2/2003 | Pope et al. ................. 623/23.6 |
| 6,517,888 B1 * | 2/2003 | Weber ................. 427/2.24 |
| 6,524,274 B1 | 2/2003 | Rosenthal et al. |
| 6,527,801 B1 | 3/2003 | Dutta |
| 6,527,938 B2 | 3/2003 | Bales et al. |
| 6,530,951 B1 * | 3/2003 | Bates et al. ................. 623/1.45 |
| 6,537,310 B1 | 3/2003 | Palmaz et al. |
| 6,544,582 B1 | 4/2003 | Yoe |
| 6,545,097 B2 | 4/2003 | Pinchuk et al. |
| 6,558,422 B1 | 5/2003 | Baker et al. |
| 6,558,733 B1 | 5/2003 | Hossainy et al. |
| 6,565,602 B2 | 5/2003 | Rolando et al. |
| 6,569,489 B1 * | 5/2003 | Li ................. 427/2.26 |
| 6,585,765 B1 | 7/2003 | Hossainy et al. |
| 6,599,558 B1 * | 7/2003 | Al-Lamee et al. ................. 427/2.24 |
| 6,607,598 B2 | 8/2003 | Schwarz et al. |
| 6,613,083 B2 | 9/2003 | Alt |
| 6,613,432 B2 | 9/2003 | Zamora et al. |
| 6,616,765 B1 | 9/2003 | Castro et al. |
| 6,620,194 B2 | 9/2003 | Ding et al. |
| 6,635,082 B1 | 10/2003 | Hossainy et al. |
| 6,638,302 B1 | 10/2003 | Curcio et al. |
| 6,641,607 B1 | 11/2003 | Hossainy et al. |
| 6,652,575 B2 | 11/2003 | Wang |
| 6,652,578 B2 | 11/2003 | Bailey et al. |
| 6,652,581 B1 | 11/2003 | Ding |
| 6,652,582 B1 | 11/2003 | Stinson |
| 6,660,034 B1 | 12/2003 | Mandrusov et al. |
| 6,663,662 B2 | 12/2003 | Pacetti et al. |
| 6,663,664 B1 | 12/2003 | Pacetti |
| 6,669,980 B2 | 12/2003 | Hansen |
| 6,673,105 B1 * | 1/2004 | Chen ................. 623/1.15 |
| 6,673,999 B1 | 1/2004 | Wang et al. |
| 6,676,987 B2 | 1/2004 | Zhong et al. |
| 6,676,989 B2 | 1/2004 | Kirkpatrick et al. |
| 0,022,824 A1 | 2/2004 | Li et al. |
| 6,689,803 B2 | 2/2004 | Hunter |
| 6,695,865 B2 | 2/2004 | Boyle et al. |
| 6,699,281 B2 | 3/2004 | Vallana et al. |
| 6,699,282 B1 | 3/2004 | Sceusa |
| 6,709,379 B1 | 3/2004 | Brandau et al. |
| 6,709,397 B2 | 3/2004 | Taylor |
| 6,709,451 B1 | 3/2004 | Noble et al. |
| 6,710,053 B2 | 3/2004 | Naicker et al. |
| 6,712,844 B2 | 3/2004 | Pacetti |
| 6,712,845 B2 | 3/2004 | Hossainy |
| 6,713,671 B1 | 3/2004 | Wang et al. |
| 6,716,444 B1 * | 4/2004 | Castro et al. ................. 424/422 |
| 6,723,120 B2 | 4/2004 | Yan |
| 6,725,901 B1 | 4/2004 | Kramer et al. |
| 6,726,712 B1 | 4/2004 | Raeder-Devens et al. |
| 6,730,120 B2 | 5/2004 | Berg et al. |
| 6,730,699 B2 | 5/2004 | Li et al. |
| 6,733,513 B2 | 5/2004 | Boyle et al. |
| 6,736,849 B2 * | 5/2004 | Li et al. ................. 623/17.11 |
| 6,740,077 B1 | 5/2004 | Brandau et al. |
| 6,752,826 B2 | 6/2004 | Holloway et al. |
| 6,752,829 B2 | 6/2004 | Kocur et al. |
| 6,753,071 B1 | 6/2004 | Pacetti |
| 6,758,859 B1 | 7/2004 | Dang et al. |
| 6,761,736 B1 | 7/2004 | Woo et al. |
| 6,764,505 B1 | 7/2004 | Hossainy et al. |
| 6,764,579 B2 | 7/2004 | Veerasamy et al. |
| 6,764,709 B2 | 7/2004 | Flanagan |
| 6,765,144 B1 | 7/2004 | Wang et al. |
| 6,767,360 B1 | 7/2004 | Alt et al. |
| 6,774,278 B1 | 8/2004 | Ragheb et al. |
| 6,776,022 B2 | 8/2004 | Kula et al. |
| 6,776,094 B1 | 8/2004 | Whitesides et al. |
| 6,780,424 B2 | 8/2004 | Claude |
| 6,780,491 B1 | 8/2004 | Cathey et al. |
| 6,783,543 B2 | 8/2004 | Jang |
| 6,790,228 B2 | 9/2004 | Hossainy et al. |
| 6,803,070 B2 | 10/2004 | Weber |
| 6,805,709 B1 | 10/2004 | Schaldach et al. |
| 6,805,898 B1 * | 10/2004 | Wu et al. ................. 427/2.25 |
| 6,807,440 B2 | 10/2004 | Weber |
| 6,815,609 B1 | 11/2004 | Wang et al. |
| 6,820,676 B2 | 11/2004 | Palmaz et al. |
| 6,827,737 B2 | 12/2004 | Hill et al. |
| 6,830,598 B1 | 12/2004 | Sung |
| 6,833,004 B2 | 12/2004 | Ishii et al. |
| 6,846,323 B2 | 1/2005 | Yip et al. |
| 6,846,841 B2 | 1/2005 | Hunter et al. |
| 6,849,085 B2 | 2/2005 | Marton |
| 6,849,089 B2 | 2/2005 | Stoll |
| 6,852,122 B2 | 2/2005 | Rush |
| 6,861,088 B2 | 3/2005 | Weber et al. |
| 6,866,805 B2 | 3/2005 | Hong et al. |
| 6,869,443 B2 | 3/2005 | Buscemi et al. |

| Patent | Date | Inventor | Ref |
|---|---|---|---|
| 6,869,701 B1 * | 3/2005 | Aita et al. | 428/698 |
| 6,875,227 B2 | 4/2005 | Yoon | |
| 6,878,249 B2 | 4/2005 | Kouyama et al. | |
| 6,884,429 B2 | 4/2005 | Koziak et al. | |
| 6,896,697 B1 | 5/2005 | Yip et al. | |
| 6,899,914 B2 | 5/2005 | Schaldach et al. | |
| 6,904,658 B2 | 6/2005 | Hines | |
| 6,908,622 B2 | 6/2005 | Barry et al. | |
| 6,908,624 B2 | 6/2005 | Hossainy et al. | |
| 6,913,617 B1 | 7/2005 | Reiss | |
| 6,915,796 B2 | 7/2005 | Sung | |
| 6,918,927 B2 | 7/2005 | Bates et al. | |
| 6,923,829 B2 | 8/2005 | Boyle et al. | |
| 6,924,004 B2 | 8/2005 | Rao et al. | |
| 6,932,930 B2 | 8/2005 | DeSimone et al. | |
| 6,936,066 B2 | 8/2005 | Palmaz et al. | |
| 6,939,320 B2 | 9/2005 | Lennox | |
| 6,951,053 B2 | 10/2005 | Padilla et al. | |
| 6,953,560 B1 | 10/2005 | Castro et al. | |
| 6,955,661 B1 | 10/2005 | Herweck et al. | |
| 6,955,685 B2 | 10/2005 | Escamilla et al. | |
| 6,962,822 B2 | 11/2005 | Hart et al. | |
| 6,971,813 B2 | 12/2005 | Shekalim et al. | |
| 6,973,718 B2 | 12/2005 | Sheppard, Jr. et al. | |
| 6,979,346 B1 | 12/2005 | Hossainy et al. | |
| 6,979,348 B2 | 12/2005 | Sundar | |
| 6,984,404 B1 | 1/2006 | Talton et al. | |
| 7,001,421 B2 | 2/2006 | Cheng et al. | |
| 7,011,680 B2 | 3/2006 | Alt | |
| 7,014,654 B2 | 3/2006 | Welsh et al. | |
| 7,018,408 B2 | 3/2006 | Bailey et al. | |
| 7,041,130 B2 | 5/2006 | Santini, Jr. et al. | |
| 7,048,939 B2 | 5/2006 | Elkins et al. | |
| 7,052,488 B2 | 5/2006 | Uhland | |
| 7,056,338 B2 | 6/2006 | Shanley et al. | |
| 7,056,339 B2 | 6/2006 | Elkins et al. | |
| 7,056,591 B1 | 6/2006 | Pacetti et al. | |
| 7,060,051 B2 | 6/2006 | Palasis | |
| 7,063,748 B2 | 6/2006 | Talton | |
| 7,066,234 B2 | 6/2006 | Sawitowski | |
| 7,077,859 B2 | 7/2006 | Sirhan et al. | |
| 7,078,108 B2 * | 7/2006 | Zhang et al. | 428/579 |
| 7,083,642 B2 | 8/2006 | Sirhan et al. | |
| 7,087,661 B1 | 8/2006 | Alberte et al. | |
| 7,099,091 B2 * | 8/2006 | Taniguchi et al. | 359/722 |
| 7,101,391 B2 | 9/2006 | Scheuermann et al. | |
| 7,101,394 B2 | 9/2006 | Hamm et al. | |
| 7,105,018 B1 | 9/2006 | Yip et al. | |
| 7,105,199 B2 | 9/2006 | Blinn et al. | |
| 7,144,840 B2 | 12/2006 | Yeung et al. | |
| 7,160,592 B2 * | 1/2007 | Rypacek et al. | 428/36.9 |
| 7,163,715 B1 | 1/2007 | Kramer | |
| 7,169,177 B2 | 1/2007 | Obara | |
| 7,169,178 B1 | 1/2007 | Santos et al. | |
| 7,195,640 B2 | 3/2007 | Falotico et al. | |
| 7,195,641 B2 | 3/2007 | Palmaz et al. | |
| 7,198,675 B2 | 4/2007 | Fox et al. | |
| 7,208,011 B2 | 4/2007 | Shanley et al. | |
| 7,208,172 B2 | 4/2007 | Birdsall et al. | |
| 7,229,471 B2 | 6/2007 | Gale et al. | |
| 7,235,096 B1 | 6/2007 | Van Tassel et al. | |
| 7,235,098 B2 | 6/2007 | Palmaz | |
| 7,238,199 B2 | 7/2007 | Feldman et al. | |
| 7,244,272 B2 * | 7/2007 | Dubson et al. | 623/1.44 |
| 7,247,166 B2 | 7/2007 | Pienknagura | |
| 7,247,338 B2 * | 7/2007 | Pui et al. | 427/2.24 |
| 7,261,735 B2 * | 8/2007 | Llanos et al. | 623/1.46 |
| 7,261,752 B2 | 8/2007 | Sung | |
| 7,273,493 B2 | 9/2007 | Ledergerber | |
| 7,294,409 B2 | 11/2007 | Lye et al. | |
| 7,311,727 B2 | 12/2007 | Mazumder et al. | |
| 7,344,563 B2 | 3/2008 | Vallana et al. | |
| 7,368,065 B2 * | 5/2008 | Yang et al. | 216/83 |
| 7,393,589 B2 | 7/2008 | Aharonov et al. | |
| 7,396,538 B2 | 7/2008 | Granada et al. | |
| 7,402,173 B2 | 7/2008 | Scheuermann et al. | |
| 7,416,558 B2 | 8/2008 | Yip et al. | |
| 7,435,256 B2 | 10/2008 | Stenzel | |
| 7,482,034 B2 | 1/2009 | Boulais | |
| 7,494,950 B2 | 2/2009 | Armitage et al. | |
| 7,497,876 B2 | 3/2009 | Tuke et al. | |
| 7,537,610 B2 * | 5/2009 | Reiss | 623/1.39 |
| 7,547,445 B2 | 6/2009 | Chudzik et al. | |
| 7,563,324 B1 * | 7/2009 | Chen et al. | 118/270 |
| 7,575,593 B2 | 8/2009 | Rea et al. | |
| 7,635,515 B1 | 12/2009 | Sherman | |
| 7,638,156 B1 | 12/2009 | Hossainy et al. | |
| 7,691,401 B2 * | 4/2010 | Castro et al. | 424/426 |
| 7,691,461 B1 | 4/2010 | Prabhu | |
| 7,713,297 B2 * | 5/2010 | Alt | 623/1.39 |
| 7,727,275 B2 | 6/2010 | Betts et al. | |
| 7,749,264 B2 * | 7/2010 | Gregorich et al. | 623/1.15 |
| 7,758,636 B2 | 7/2010 | Shanley et al. | |
| 7,771,773 B2 * | 8/2010 | Namavar | 427/2.1 |
| 7,837,726 B2 | 11/2010 | Von Oepen et al. | |
| 2001/0001834 A1 | 5/2001 | Palmaz et al. | |
| 2001/0002000 A1 | 5/2001 | Kumar et al. | |
| 2001/0002435 A1 | 5/2001 | Berg et al. | |
| 2001/0013166 A1 | 8/2001 | Yan | |
| 2001/0014717 A1 | 8/2001 | Hossainy et al. | |
| 2001/0014821 A1 | 8/2001 | Juman et al. | |
| 2001/0027299 A1 | 10/2001 | Yang et al. | |
| 2001/0029660 A1 | 10/2001 | Johnson | |
| 2001/0032011 A1 | 10/2001 | Stanford | |
| 2001/0032013 A1 | 10/2001 | Marton | |
| 2001/0044651 A1 | 11/2001 | Steinke et al. | |
| 2002/0000175 A1 | 1/2002 | Hintermaier et al. | |
| 2002/0004060 A1 | 1/2002 | Heublein et al. | |
| 2002/0007102 A1 | 1/2002 | Salmon et al. | |
| 2002/0007209 A1 | 1/2002 | Scheerder et al. | |
| 2002/0009604 A1 | 1/2002 | Zamora et al. | |
| 2002/0010505 A1 * | 1/2002 | Richter | 623/1.15 |
| 2002/0016623 A1 | 2/2002 | Kula et al. | |
| 2002/0016624 A1 | 2/2002 | Patterson et al. | |
| 2002/0028827 A1 | 3/2002 | Naicker et al. | |
| 2002/0032477 A1 | 3/2002 | Helmus et al. | |
| 2002/0038146 A1 | 3/2002 | Harry | |
| 2002/0042039 A1 | 4/2002 | Kim et al. | |
| 2002/0051730 A1 | 5/2002 | Bodnar et al. | |
| 2002/0051846 A1 | 5/2002 | Kirkpatrick et al. | |
| 2002/0052288 A1 | 5/2002 | Krell et al. | |
| 2002/0065553 A1 | 5/2002 | Weber | |
| 2002/0072734 A1 | 6/2002 | Liedtke | |
| 2002/0077520 A1 | 6/2002 | Segal et al. | |
| 2002/0077693 A1 | 6/2002 | Barclay et al. | |
| 2002/0087123 A1 | 7/2002 | Hossainy et al. | |
| 2002/0091375 A1 | 7/2002 | Sahatjian et al. | |
| 2002/0095871 A1 * | 7/2002 | McArdle et al. | 51/298 |
| 2002/0098278 A1 | 7/2002 | Bates et al. | |
| 2002/0099359 A1 | 7/2002 | Santini, Jr. et al. | |
| 2002/0099438 A1 | 7/2002 | Furst | |
| 2002/0103527 A1 | 8/2002 | Kocur et al. | |
| 2002/0103528 A1 | 8/2002 | Schaldach et al. | |
| 2002/0104599 A1 | 8/2002 | Tillotson et al. | |
| 2002/0121497 A1 | 9/2002 | Tomonto | |
| 2002/0123801 A1 * | 9/2002 | Pacetti et al. | 623/1.46 |
| 2002/0133222 A1 | 9/2002 | Das | |
| 2002/0133225 A1 | 9/2002 | Gordon | |
| 2002/0138100 A1 | 9/2002 | Stoll et al. | |
| 2002/0138136 A1 | 9/2002 | Chandresekaran et al. | |
| 2002/0140137 A1 | 10/2002 | Sapieszko et al. | |
| 2002/0142579 A1 | 10/2002 | Vincent et al. | |
| 2002/0144757 A1 | 10/2002 | Craig et al. | |
| 2002/0155212 A1 | 10/2002 | Hossainy | |
| 2002/0165265 A1 | 11/2002 | Hunter et al. | |
| 2002/0165600 A1 | 11/2002 | Banas et al. | |
| 2002/0165607 A1 | 11/2002 | Alt | |
| 2002/0167118 A1 | 11/2002 | Billiet et al. | |
| 2002/0168466 A1 | 11/2002 | Tapphorn et al. | |
| 2002/0169493 A1 | 11/2002 | Widenhouse et al. | |
| 2002/0178570 A1 | 11/2002 | Sogard et al. | |
| 2002/0182241 A1 * | 12/2002 | Borenstein et al. | 424/422 |
| 2002/0183581 A1 | 12/2002 | Yoe et al. | |
| 2002/0183682 A1 | 12/2002 | Darvish et al. | |
| 2002/0187260 A1 | 12/2002 | Sheppard, Jr. et al. | |
| 2002/0193336 A1 | 12/2002 | Elkins et al. | |
| 2002/0193869 A1 | 12/2002 | Dang | |
| 2002/0197178 A1 | 12/2002 | Yan | |

| | | |
|---|---|---|
| 2002/0198601 A1 | 12/2002 | Bales et al. |
| 2003/0003160 A1 | 1/2003 | Pugh et al. |
| 2003/0003220 A1 | 1/2003 | Zhong et al. |
| 2003/0004563 A1 | 1/2003 | Jackson et al. |
| 2003/0004564 A1* | 1/2003 | Elkins et al. ............... 623/1.15 |
| 2003/0006250 A1 | 1/2003 | Tapphorn et al. |
| 2003/0009214 A1 | 1/2003 | Shanley |
| 2003/0009233 A1 | 1/2003 | Blinn et al. |
| 2003/0018380 A1 | 1/2003 | Craig et al. |
| 2003/0018381 A1 | 1/2003 | Whitcher et al. |
| 2003/0021820 A1 | 1/2003 | Ahola et al. |
| 2003/0023300 A1 | 1/2003 | Bailey et al. |
| 2003/0028242 A1 | 2/2003 | Vallana et al. |
| 2003/0028243 A1 | 2/2003 | Bates et al. |
| 2003/0032892 A1 | 2/2003 | Erlach et al. |
| 2003/0033007 A1 | 2/2003 | Sirhan et al. |
| 2003/0044446 A1 | 3/2003 | Moro et al. |
| 2003/0047028 A1 | 3/2003 | Kunitake et al. |
| 2003/0047505 A1 | 3/2003 | Grimes et al. |
| 2003/0050687 A1 | 3/2003 | Schwade et al. |
| 2003/0059640 A1 | 3/2003 | Marton et al. |
| 2003/0060871 A1 | 3/2003 | Hill et al. |
| 2003/0060873 A1 | 3/2003 | Gertner et al. |
| 2003/0060877 A1 | 3/2003 | Falotico et al. |
| 2003/0064095 A1 | 4/2003 | Martin et al. |
| 2003/0069631 A1 | 4/2003 | Stoll |
| 2003/0074053 A1 | 4/2003 | Palmaz et al. |
| 2003/0074075 A1 | 4/2003 | Thomas et al. |
| 2003/0077200 A1 | 4/2003 | Craig et al. |
| 2003/0083614 A1 | 5/2003 | Eisert |
| 2003/0083646 A1 | 5/2003 | Sirhan et al. |
| 2003/0083731 A1 | 5/2003 | Kramer et al. |
| 2003/0087024 A1 | 5/2003 | Flanagan |
| 2003/0088307 A1* | 5/2003 | Shulze et al. ............... 623/1.15 |
| 2003/0088312 A1 | 5/2003 | Kopia et al. |
| 2003/0100865 A1 | 5/2003 | Santini, Jr. et al. |
| 2003/0104028 A1 | 6/2003 | Hossainy et al. |
| 2003/0105511 A1 | 6/2003 | Welsh et al. |
| 2003/0108659 A1 | 6/2003 | Bales et al. |
| 2003/0114917 A1 | 6/2003 | Holloway et al. |
| 2003/0114921 A1 | 6/2003 | Yoon |
| 2003/0118649 A1* | 6/2003 | Gao et al. .................. 424/471 |
| 2003/0125803 A1 | 7/2003 | Vallana et al. |
| 2003/0130206 A1 | 7/2003 | Koziak et al. |
| 2003/0130718 A1 | 7/2003 | Palmas et al. |
| 2003/0138645 A1 | 7/2003 | Gleason et al. |
| 2003/0139799 A1* | 7/2003 | Ley et al. .................. 623/1.15 |
| 2003/0144728 A1 | 7/2003 | Scheuermann et al. |
| 2003/0150380 A1 | 8/2003 | Yoe |
| 2003/0153901 A1 | 8/2003 | Herweck et al. |
| 2003/0153971 A1 | 8/2003 | Chandrasekaran |
| 2003/0158598 A1 | 8/2003 | Ashton et al. |
| 2003/0167878 A1 | 9/2003 | Al-Salim et al. |
| 2003/0170605 A1 | 9/2003 | Long et al. |
| 2003/0181975 A1 | 9/2003 | Ishii et al. |
| 2003/0185895 A1 | 10/2003 | Lanphere et al. |
| 2003/0185964 A1 | 10/2003 | Weber et al. |
| 2003/0190406 A1 | 10/2003 | Hossainy et al. |
| 2003/0195613 A1 | 10/2003 | Curcio et al. |
| 2003/0203991 A1 | 10/2003 | Schottman et al. |
| 2003/0204168 A1 | 10/2003 | Bosma et al. |
| 2003/0208256 A1 | 11/2003 | DiMatteo et al. |
| 2003/0211135 A1 | 11/2003 | Greenhalgh et al. |
| 2003/0216803 A1 | 11/2003 | Ledergerber |
| 2003/0219562 A1 | 11/2003 | Rypacek et al. |
| 2003/0225450 A1 | 12/2003 | Shulze et al. |
| 2003/0236323 A1 | 12/2003 | Ratner et al. |
| 2003/0236514 A1 | 12/2003 | Schwarz |
| 2004/0000540 A1 | 1/2004 | Soboyejo et al. |
| 2004/0002755 A1 | 1/2004 | Fischell et al. |
| 2004/0006382 A1 | 1/2004 | Sohier |
| 2004/0013873 A1 | 1/2004 | Wendorff et al. |
| 2004/0016651 A1 | 1/2004 | Windler |
| 2004/0018296 A1 | 1/2004 | Castro et al. |
| 2004/0019376 A1 | 1/2004 | Alt |
| 2004/0026811 A1 | 2/2004 | Murphy et al. |
| 2004/0028875 A1* | 2/2004 | Van Rijn et al. ............... 428/98 |
| 2004/0029303 A1 | 2/2004 | Hart et al. |
| 2004/0029706 A1 | 2/2004 | Barrera et al. |
| 2004/0030218 A1 | 2/2004 | Kocur et al. |
| 2004/0030377 A1 | 2/2004 | Dubson et al. |
| 2004/0039438 A1* | 2/2004 | Alt ............... 623/1.15 |
| 2004/0039441 A1 | 2/2004 | Rowland et al. |
| 2004/0044397 A1 | 3/2004 | Stinson |
| 2004/0047980 A1 | 3/2004 | Pacetti et al. |
| 2004/0058858 A1 | 3/2004 | Hu |
| 2004/0059290 A1 | 3/2004 | Palasis |
| 2004/0059407 A1 | 3/2004 | Escamilla et al. |
| 2004/0059409 A1* | 3/2004 | Stenzel ............... 623/1.15 |
| 2004/0067301 A1 | 4/2004 | Ding |
| 2004/0071861 A1 | 4/2004 | Mandrusov et al. |
| 2004/0073284 A1 | 4/2004 | Bates et al. |
| 2004/0073298 A1 | 4/2004 | Hossainy |
| 2004/0078071 A1 | 4/2004 | Escamilla et al. |
| 2004/0086674 A1 | 5/2004 | Holman |
| 2004/0088038 A1 | 5/2004 | Dehnad et al. |
| 2004/0088041 A1 | 5/2004 | Stanford |
| 2004/0092653 A1 | 5/2004 | Ruberti et al. |
| 2004/0093071 A1 | 5/2004 | Jang |
| 2004/0093076 A1 | 5/2004 | White et al. |
| 2004/0098089 A1 | 5/2004 | Weber |
| 2004/0098119 A1 | 5/2004 | Wang |
| 2004/0102758 A1 | 5/2004 | Davila et al. |
| 2004/0106984 A1 | 6/2004 | Stinson |
| 2004/0106985 A1 | 6/2004 | Jang |
| 2004/0106987 A1 | 6/2004 | Palasis et al. |
| 2004/0106994 A1 | 6/2004 | De Maeztus Martinez et al. |
| 2004/0111150 A1 | 6/2004 | Berg et al. |
| 2004/0116999 A1 | 6/2004 | Ledergerber |
| 2004/0117005 A1 | 6/2004 | Gadde et al. |
| 2004/0117008 A1 | 6/2004 | Wnendt et al. |
| 2004/0122504 A1 | 6/2004 | Hogendijk |
| 2004/0126566 A1 | 7/2004 | Axen et al. |
| 2004/0133270 A1 | 7/2004 | Grandt |
| 2004/0134886 A1 | 7/2004 | Wagner et al. |
| 2004/0142014 A1 | 7/2004 | Litvack et al. |
| 2004/0143317 A1 | 7/2004 | Stinson et al. |
| 2004/0143321 A1 | 7/2004 | Litvack et al. |
| 2004/0148010 A1 | 7/2004 | Rush |
| 2004/0148015 A1 | 7/2004 | Lye et al. |
| 2004/0158308 A1 | 8/2004 | Hogendijk et al. |
| 2004/0167572 A1 | 8/2004 | Roth et al. |
| 2004/0167612 A1 | 8/2004 | Grignani et al. |
| 2004/0171978 A1 | 9/2004 | Shalaby |
| 2004/0172124 A1 | 9/2004 | Vallana et al. |
| 2004/0178523 A1 | 9/2004 | Kim et al. |
| 2004/0181252 A1 | 9/2004 | Boyle et al. |
| 2004/0181275 A1 | 9/2004 | Noble et al. |
| 2004/0181276 A1 | 9/2004 | Brown et al. |
| 2004/0185168 A1 | 9/2004 | Weber et al. |
| 2004/0191293 A1 | 9/2004 | Claude |
| 2004/0191404 A1 | 9/2004 | Hossainy et al. |
| 2004/0202692 A1 | 10/2004 | Shanley et al. |
| 2004/0204750 A1 | 10/2004 | Dinh |
| 2004/0211362 A1 | 10/2004 | Castro et al. |
| 2004/0215169 A1 | 10/2004 | Li |
| 2004/0215313 A1 | 10/2004 | Cheng |
| 2004/0219214 A1 | 11/2004 | Gravett et al. |
| 2004/0220510 A1 | 11/2004 | Koullick et al. |
| 2004/0220662 A1 | 11/2004 | Dang et al. |
| 2004/0224001 A1 | 11/2004 | Pacetti et al. |
| 2004/0225346 A1 | 11/2004 | Mazumder et al. |
| 2004/0225347 A1 | 11/2004 | Lang |
| 2004/0228905 A1 | 11/2004 | Greenspan et al. |
| 2004/0230176 A1 | 11/2004 | Shanahan et al. |
| 2004/0230290 A1 | 11/2004 | Weber et al. |
| 2004/0230293 A1 | 11/2004 | Yip et al. |
| 2004/0234737 A1 | 11/2004 | Pacetti |
| 2004/0234748 A1 | 11/2004 | Stenzel |
| 2004/0236399 A1 | 11/2004 | Sundar |
| 2004/0236415 A1 | 11/2004 | Thomas |
| 2004/0236416 A1 | 11/2004 | Falotico |
| 2004/0237282 A1 | 12/2004 | Hines |
| 2004/0242106 A1 | 12/2004 | Rabasco et al. |
| 2004/0243217 A1 | 12/2004 | Andersen et al. |
| 2004/0243241 A1 | 12/2004 | Istephanous |
| 2004/0247671 A1 | 12/2004 | Prescott et al. |
| 2004/0249444 A1 | 12/2004 | Reiss |

| | | | | | | |
|---|---|---|---|---|---|---|
| 2004/0249449 A1 | 12/2004 | Shanley et al. | | 2005/0220853 A1 | 10/2005 | Dao et al. |
| 2004/0254635 A1 | 12/2004 | Shanley et al. | | 2005/0221072 A1 | 10/2005 | Dubrow et al. |
| 2004/0261702 A1 | 12/2004 | Grabowy et al. | | 2005/0228477 A1 | 10/2005 | Grainger et al. |
| 2005/0002865 A1 | 1/2005 | Klaveness et al. | | 2005/0228491 A1 | 10/2005 | Snyder et al. |
| 2005/0010275 A1 | 1/2005 | Sahatjian et al. | | 2005/0232968 A1 | 10/2005 | Palmaz et al. |
| 2005/0015142 A1 | 1/2005 | Austin et al. | | 2005/0233965 A1 | 10/2005 | Schwartz et al. |
| 2005/0019265 A1 | 1/2005 | Hammer et al. | | 2005/0244459 A1 | 11/2005 | DeWitt et al. |
| 2005/0019371 A1 | 1/2005 | Anderson et al. | | 2005/0251245 A1 | 11/2005 | Sieradzki et al. |
| 2005/0020614 A1 | 1/2005 | Prescott et al. | | 2005/0251249 A1 | 11/2005 | Sahatjian et al. |
| 2005/0021127 A1 | 1/2005 | Kawula | | 2005/0255707 A1 | 11/2005 | Hart et al. |
| 2005/0021128 A1 | 1/2005 | Nakahama et al. | | 2005/0261760 A1 | 11/2005 | Weber |
| 2005/0027350 A1 | 2/2005 | Momma et al. | | 2005/0266039 A1 | 12/2005 | Weber |
| 2005/0033411 A1 | 2/2005 | Wu et al. | | 2005/0266040 A1 | 12/2005 | Gerberding |
| 2005/0033412 A1 | 2/2005 | Wu et al. | | 2005/0267561 A1 | 12/2005 | Jones et al. |
| 2005/0033417 A1 | 2/2005 | Borges et al. | | 2005/0271703 A1 | 12/2005 | Anderson et al. |
| 2005/0037047 A1 | 2/2005 | Song | | 2005/0271706 A1 | 12/2005 | Anderson et al. |
| 2005/0038498 A1 | 2/2005 | Dubrow et al. | | 2005/0276837 A1 | 12/2005 | Anderson et al. |
| 2005/0042288 A1 | 2/2005 | Koblish et al. | | 2005/0278016 A1 | 12/2005 | Welsh et al. |
| 2005/0055080 A1 | 3/2005 | Istephanous et al. | | 2005/0278021 A1 | 12/2005 | Bates et al. |
| 2005/0055085 A1 | 3/2005 | Rivron et al. | | 2005/0281863 A1 | 12/2005 | Anderson et al. |
| 2005/0060020 A1 | 3/2005 | Jenson | | 2005/0285073 A1 | 12/2005 | Singh et al. |
| 2005/0060021 A1* | 3/2005 | O'Brien et al. .............. 623/1.15 | | 2005/0287188 A1 | 12/2005 | Anderson et al. |
| 2005/0069630 A1 | 3/2005 | Fox et al. | | 2006/0013850 A1 | 1/2006 | Domb |
| 2005/0070989 A1 | 3/2005 | Lye et al. | | 2006/0015175 A1 | 1/2006 | Palmaz et al. |
| 2005/0070990 A1 | 3/2005 | Stinson et al. | | 2006/0015361 A1 | 1/2006 | Sattler et al. |
| 2005/0070996 A1 | 3/2005 | Dinh et al. | | 2006/0020742 A1 | 1/2006 | Au et al. |
| 2005/0072544 A1 | 4/2005 | Palmaz et al. | | 2006/0025848 A1 | 2/2006 | Weber et al. |
| 2005/0074479 A1 | 4/2005 | Weber et al. | | 2006/0034884 A1 | 2/2006 | Stenzel |
| 2005/0074545 A1 | 4/2005 | Thomas | | 2006/0035026 A1 | 2/2006 | Atanasoska et al. |
| 2005/0077305 A1 | 4/2005 | Guevara | | 2006/0038027 A1 | 2/2006 | O'Connor et al. |
| 2005/0079199 A1 | 4/2005 | Heruth et al. | | 2006/0051397 A1 | 3/2006 | Maier et al. |
| 2005/0079201 A1 | 4/2005 | Rathenow et al. | | 2006/0052744 A1 | 3/2006 | Weber |
| 2005/0079356 A1 | 4/2005 | Rathenow et al. | | 2006/0052863 A1 | 3/2006 | Harder et al. |
| 2005/0087520 A1 | 4/2005 | Wang et al. | | 2006/0052864 A1 | 3/2006 | Harder et al. |
| 2005/0092615 A1 | 5/2005 | Birdsall et al. | | 2006/0062820 A1 | 3/2006 | Gertner et al. |
| 2005/0096731 A1 | 5/2005 | Looi et al. | | 2006/0069427 A1 | 3/2006 | Savage et al. |
| 2005/0100577 A1 | 5/2005 | Parker et al. | | 2006/0075044 A1 | 4/2006 | Fox et al. |
| 2005/0100609 A1 | 5/2005 | Claude | | 2006/0075092 A1 | 4/2006 | Kidokoro |
| 2005/0102025 A1 | 5/2005 | Laroche et al. | | 2006/0079863 A1 | 4/2006 | Burgmeier et al. |
| 2005/0106212 A1 | 5/2005 | Gertner et al. | | 2006/0085062 A1 | 4/2006 | Lee et al. |
| 2005/0107870 A1 | 5/2005 | Wang et al. | | 2006/0085065 A1 | 4/2006 | Krause et al. |
| 2005/0110214 A1 | 5/2005 | Shank et al. | | 2006/0088561 A1 | 4/2006 | Eini et al. |
| 2005/0113936 A1 | 5/2005 | Brustad et al. | | 2006/0088566 A1 | 4/2006 | Parsonage et al. |
| 2005/0119723 A1 | 6/2005 | Peacock | | 2006/0088567 A1 | 4/2006 | Warner et al. |
| 2005/0129727 A1 | 6/2005 | Weber et al. | | 2006/0088666 A1 | 4/2006 | Kobrin et al. |
| 2005/0131509 A1 | 6/2005 | Atanassoska et al. | | 2006/0093643 A1 | 5/2006 | Stenzel |
| 2005/0131521 A1 | 6/2005 | Marton | | 2006/0093646 A1 | 5/2006 | Cima et al. |
| 2005/0131522 A1 | 6/2005 | Stinson et al. | | 2006/0095123 A1 | 5/2006 | Flanagan |
| 2005/0136090 A1 | 6/2005 | Falotico et al. | | 2006/0100696 A1 | 5/2006 | Atanasoska et al. |
| 2005/0137677 A1 | 6/2005 | Rush | | 2006/0115512 A1 | 6/2006 | Peacock et al. |
| 2005/0137679 A1 | 6/2005 | Changelian et al. | | 2006/0121080 A1 | 6/2006 | Lye et al. |
| 2005/0137684 A1 | 6/2005 | Changelian et al. | | 2006/0122694 A1 | 6/2006 | Stinson et al. |
| 2005/0149102 A1* | 7/2005 | Radisch et al. .............. 606/194 | | 2006/0125144 A1 | 6/2006 | Weber et al. |
| 2005/0149170 A1 | 7/2005 | Tassel et al. | | 2006/0127442 A1 | 6/2006 | Helmus |
| 2005/0159804 A1 | 7/2005 | Lad et al. | | 2006/0127443 A1 | 6/2006 | Helmus |
| 2005/0159805 A1 | 7/2005 | Weber et al. | | 2006/0129215 A1 | 6/2006 | Helmus et al. |
| 2005/0160600 A1 | 7/2005 | Bien et al. | | 2006/0129225 A1 | 6/2006 | Kopia et al. |
| 2005/0163954 A1 | 7/2005 | Shaw | | 2006/0136048 A1 | 6/2006 | Pacetti et al. |
| 2005/0165467 A1 | 7/2005 | Hunter et al. | | 2006/0140867 A1 | 6/2006 | Helfer et al. |
| 2005/0165468 A1 | 7/2005 | Marton | | 2006/0141156 A1 | 6/2006 | Viel et al. |
| 2005/0165476 A1 | 7/2005 | Furst et al. | | 2006/0142853 A1 | 6/2006 | Wang et al. |
| 2005/0171595 A1 | 8/2005 | Feldman et al. | | 2006/0153729 A1 | 7/2006 | Stinson et al. |
| 2005/0180919 A1 | 8/2005 | Tedeschi | | 2006/0155361 A1 | 7/2006 | Schomig et al. |
| 2005/0182478 A1 | 8/2005 | Holman et al. | | 2006/0167543 A1 | 7/2006 | Bailey et al. |
| 2005/0186250 A1 | 8/2005 | Gertner et al. | | 2006/0171985 A1 | 8/2006 | Richard et al. |
| 2005/0187608 A1* | 8/2005 | O'Hara .................. 623/1.15 | | 2006/0178727 A1 | 8/2006 | Richter |
| 2005/0192657 A1 | 9/2005 | Colen et al. | | 2006/0184235 A1 | 8/2006 | Rivron et al. |
| 2005/0192664 A1 | 9/2005 | Eisert | | 2006/0193886 A1 | 8/2006 | Owens et al. |
| 2005/0196424 A1 | 9/2005 | Chappa | | 2006/0193887 A1 | 8/2006 | Owens et al. |
| 2005/0196518 A1 | 9/2005 | Stenzel | | 2006/0193888 A1 | 8/2006 | Lye et al. |
| 2005/0197687 A1 | 9/2005 | Molaei et al. | | 2006/0193889 A1 | 8/2006 | Spradlin et al. |
| 2005/0203606 A1 | 9/2005 | Vancamp | | 2006/0193890 A1 | 8/2006 | Owens et al. |
| 2005/0208094 A1* | 9/2005 | Armitage et al. .............. 424/423 | | 2006/0199876 A1* | 9/2006 | Troczynski et al. .......... 523/115 |
| 2005/0208098 A1 | 9/2005 | Castro et al. | | 2006/0200229 A1 | 9/2006 | Burgermeister et al. |
| 2005/0208100 A1 | 9/2005 | Weber et al. | | 2006/0200231 A1 | 9/2006 | O'Brien et al. |
| 2005/0209681 A1 | 9/2005 | Curcio et al. | | 2006/0210595 A1 | 9/2006 | Singhvi et al. |
| 2005/0211680 A1 | 9/2005 | Li et al. | | 2006/0212109 A1 | 9/2006 | Sirhan et al. |
| 2005/0214951 A1 | 9/2005 | Nahm et al. | | 2006/0222679 A1 | 10/2006 | Shanley et al. |
| 2005/0216074 A1 | 9/2005 | Sahatjian et al. | | 2006/0222844 A1 | 10/2006 | Stinson |

| | | |
|---|---|---|
| 2006/0224234 A1 | 10/2006 | Jayaraman |
| 2006/0229711 A1* | 10/2006 | Yan et al. ..................... 623/1.38 |
| 2006/0229713 A1 | 10/2006 | Shanley et al. |
| 2006/0229715 A1 | 10/2006 | Istephanous et al. |
| 2006/0230476 A1 | 10/2006 | Atanasoska et al. |
| 2006/0233941 A1 | 10/2006 | Olson |
| 2006/0251701 A1 | 11/2006 | Lynn et al. |
| 2006/0263512 A1 | 11/2006 | Glocker |
| 2006/0263515 A1 | 11/2006 | Rieck et al. |
| 2006/0264138 A1* | 11/2006 | Sowinski et al. ............ 442/315 |
| 2006/0271156 A1* | 11/2006 | Ledergerber ................ 623/1.13 |
| 2006/0271169 A1 | 11/2006 | Lye et al. |
| 2006/0275554 A1 | 12/2006 | Zhao et al. |
| 2006/0276877 A1 | 12/2006 | Owens et al. |
| 2006/0276878 A1 | 12/2006 | Owens et al. |
| 2006/0276879 A1 | 12/2006 | Lye et al. |
| 2006/0276884 A1* | 12/2006 | Lye et al. ..................... 623/1.39 |
| 2006/0276885 A1* | 12/2006 | Lye et al. ..................... 623/1.39 |
| 2006/0276910 A1 | 12/2006 | Weber |
| 2006/0280770 A1 | 12/2006 | Hossainy et al. |
| 2006/0292388 A1 | 12/2006 | Palumbo et al. |
| 2007/0003589 A1 | 1/2007 | Astafieva et al. |
| 2007/0003817 A1 | 1/2007 | Umeda et al. |
| 2007/0032858 A1 | 2/2007 | Santos et al. |
| 2007/0032864 A1 | 2/2007 | Furst et al. |
| 2007/0036905 A1 | 2/2007 | Kramer |
| 2007/0038176 A1 | 2/2007 | Weber et al. |
| 2007/0038289 A1 | 2/2007 | Nishide et al. |
| 2007/0048452 A1 | 3/2007 | Feng et al. |
| 2007/0052497 A1 | 3/2007 | Tada |
| 2007/0055349 A1 | 3/2007 | Santos et al. |
| 2007/0055354 A1 | 3/2007 | Santos et al. |
| 2007/0059435 A1 | 3/2007 | Santos et al. |
| 2007/0065418 A1 | 3/2007 | Vallana et al. |
| 2007/0071789 A1 | 3/2007 | Pantelidis et al. |
| 2007/0072978 A1 | 3/2007 | Zoromski et al. |
| 2007/0073385 A1 | 3/2007 | Schaeffer et al. |
| 2007/0073390 A1* | 3/2007 | Lee .............................. 623/1.46 |
| 2007/0106347 A1 | 5/2007 | Lin |
| 2007/0110888 A1 | 5/2007 | Radhakrishnan et al. |
| 2007/0112421 A1 | 5/2007 | O'Brien |
| 2007/0123973 A1 | 5/2007 | Roth et al. |
| 2007/0128245 A1* | 6/2007 | Rosenberg et al. ........... 424/423 |
| 2007/0129789 A1* | 6/2007 | Cottone et al. ............... 623/1.41 |
| 2007/0134288 A1 | 6/2007 | Parsonage et al. |
| 2007/0135908 A1 | 6/2007 | Zhao |
| 2007/0148251 A1 | 6/2007 | Hossainy et al. |
| 2007/0151093 A1 | 7/2007 | Curcio et al. |
| 2007/0154513 A1 | 7/2007 | Atanasoska et al. |
| 2007/0156231 A1 | 7/2007 | Weber |
| 2007/0173923 A1* | 7/2007 | Savage et al. ................ 623/1.15 |
| 2007/0181433 A1 | 8/2007 | Birdsall et al. |
| 2007/0190104 A1 | 8/2007 | Kamath et al. |
| 2007/0191923 A1 | 8/2007 | Weber et al. |
| 2007/0191928 A1 | 8/2007 | Rolando et al. |
| 2007/0191931 A1 | 8/2007 | Weber et al. |
| 2007/0191943 A1 | 8/2007 | Shrivastava et al. |
| 2007/0198081 A1 | 8/2007 | Castro et al. |
| 2007/0202466 A1 | 8/2007 | Schwarz et al. |
| 2007/0207186 A1* | 9/2007 | Scanlon et al. ............... 424/424 |
| 2007/0208412 A1* | 9/2007 | Elmaleh ....................... 623/1.15 |
| 2007/0212547 A1 | 9/2007 | Fredrickson et al. |
| 2007/0213827 A1* | 9/2007 | Arramon .................... 623/17.11 |
| 2007/0219626 A1 | 9/2007 | Rolando et al. |
| 2007/0224116 A1 | 9/2007 | Chandrasekaran et al. |
| 2007/0224224 A1 | 9/2007 | Cordeira Da Silva et al. |
| 2007/0224235 A1 | 9/2007 | Tenney et al. |
| 2007/0224244 A1 | 9/2007 | Weber et al. |
| 2007/0244569 A1* | 10/2007 | Weber et al. ................ 623/23.75 |
| 2007/0254091 A1 | 11/2007 | Fredrickson et al. |
| 2007/0255392 A1 | 11/2007 | Johnson |
| 2007/0264303 A1 | 11/2007 | Atanasoska et al. |
| 2007/0269480 A1 | 11/2007 | Richard et al. |
| 2007/0299509 A1 | 12/2007 | Ding |
| 2008/0003251 A1 | 1/2008 | Zhou |
| 2008/0004691 A1 | 1/2008 | Weber et al. |
| 2008/0008654 A1 | 1/2008 | Clarke et al. |
| 2008/0038146 A1 | 2/2008 | Wachter et al. |
| 2008/0050413 A1 | 2/2008 | Horvers et al. |
| 2008/0050415 A1 | 2/2008 | Atanasoska et al. |
| 2008/0051881 A1 | 2/2008 | Feng et al. |
| 2008/0057103 A1 | 3/2008 | Roorda |
| 2008/0058921 A1* | 3/2008 | Lindquist ..................... 623/1.42 |
| 2008/0069854 A1* | 3/2008 | Xiao et al. ..................... 424/423 |
| 2008/0071348 A1 | 3/2008 | Boismier et al. |
| 2008/0071349 A1* | 3/2008 | Atanasoska et al. ......... 623/1.15 |
| 2008/0071350 A1* | 3/2008 | Stinson ........................ 623/1.15 |
| 2008/0071351 A1* | 3/2008 | Flanagan et al. ............. 623/1.15 |
| 2008/0071352 A1* | 3/2008 | Weber et al. ................. 623/1.15 |
| 2008/0071353 A1* | 3/2008 | Weber et al. ................. 623/1.15 |
| 2008/0071355 A1* | 3/2008 | Weber et al. ................. 623/1.16 |
| 2008/0071358 A1* | 3/2008 | Weber et al. ................. 623/1.42 |
| 2008/0086199 A1* | 4/2008 | Dave et al. ................... 623/1.42 |
| 2008/0086201 A1* | 4/2008 | Weber et al. ................. 623/1.42 |
| 2008/0097577 A1* | 4/2008 | Atanasoska et al. ......... 623/1.15 |
| 2008/0107890 A1 | 5/2008 | Bureau et al. |
| 2008/0124373 A1* | 5/2008 | Xiao et al. ..................... 424/423 |
| 2008/0140186 A1 | 6/2008 | Grignani et al. |
| 2008/0145400 A1* | 6/2008 | Weber et al. ................. 424/423 |
| 2008/0147177 A1 | 6/2008 | Scheuermann et al. |
| 2008/0152929 A1 | 6/2008 | Zhao |
| 2008/0160259 A1 | 7/2008 | Nielson et al. |
| 2008/0161906 A1* | 7/2008 | Atanasoska et al. ......... 623/1.38 |
| 2008/0171929 A1 | 7/2008 | Katims |
| 2008/0188836 A1 | 8/2008 | Weber et al. |
| 2008/0190034 A1* | 8/2008 | Rosenflanz et al. ............. 51/307 |
| 2008/0241218 A1 | 10/2008 | McMorrow et al. |
| 2008/0243231 A1 | 10/2008 | Flanagan et al. |
| 2008/0243240 A1 | 10/2008 | Doty et al. |
| 2008/0249600 A1 | 10/2008 | Atanasoska et al. |
| 2008/0249615 A1 | 10/2008 | Weber |
| 2008/0255508 A1* | 10/2008 | Wang ....................... 604/103.02 |
| 2008/0255657 A1 | 10/2008 | Gregorich et al. |
| 2008/0262607 A1 | 10/2008 | Fricke |
| 2008/0275543 A1 | 11/2008 | Lenz et al. |
| 2008/0288048 A1 | 11/2008 | Rolando et al. |
| 2008/0290467 A1 | 11/2008 | Shue et al. |
| 2008/0294236 A1 | 11/2008 | Anand et al. |
| 2008/0294246 A1 | 11/2008 | Scheuermann et al. |
| 2008/0306584 A1 | 12/2008 | Kramer-Brown |
| 2009/0012603 A1 | 1/2009 | Xu et al. |
| 2009/0018639 A1* | 1/2009 | Kuehling ..................... 623/1.15 |
| 2009/0018642 A1 | 1/2009 | Benco |
| 2009/0018644 A1 | 1/2009 | Weber et al. |
| 2009/0018647 A1 | 1/2009 | Benco et al. |
| 2009/0028785 A1 | 1/2009 | Clarke |
| 2009/0030504 A1 | 1/2009 | Weber et al. |
| 2009/0076588 A1 | 3/2009 | Weber |
| 2009/0076595 A1 | 3/2009 | Lindquist et al. |
| 2009/0081450 A1 | 3/2009 | Ascher et al. |
| 2009/0112310 A1 | 4/2009 | Zhang |
| 2009/0118809 A1 | 5/2009 | Scheuermann et al. |
| 2009/0118812 A1 | 5/2009 | Kokate et al. |
| 2009/0118813 A1* | 5/2009 | Scheuermann et al. ..... 623/1.15 |
| 2009/0118814 A1 | 5/2009 | Schoenle et al. |
| 2009/0118815 A1 | 5/2009 | Arcand et al. |
| 2009/0118818 A1* | 5/2009 | Foss et al. ................... 623/1.42 |
| 2009/0118820 A1 | 5/2009 | Gregorich et al. |
| 2009/0118821 A1* | 5/2009 | Scheuermann et al. ..... 623/1.49 |
| 2009/0118822 A1 | 5/2009 | Holman et al. |
| 2009/0118823 A1 | 5/2009 | Atanasoska et al. |
| 2009/0123517 A1 | 5/2009 | Flanagan et al. |
| 2009/0123521 A1 | 5/2009 | Weber et al. |
| 2009/0138077 A1 | 5/2009 | Weber et al. |
| 2009/0149942 A1* | 6/2009 | Edelman et al. ............. 623/1.15 |
| 2009/0157165 A1* | 6/2009 | Miller et al. ................. 623/1.15 |
| 2009/0157166 A1 | 6/2009 | Singhal et al. |
| 2009/0157172 A1 | 6/2009 | Kokate et al. |
| 2009/0177273 A1 | 7/2009 | Piveteau et al. |
| 2009/0186068 A1 | 7/2009 | Miller et al. |
| 2009/0192593 A1 | 7/2009 | Meyer et al. |
| 2009/0202610 A1* | 8/2009 | Wilson ......................... 424/426 |
| 2009/0208428 A1 | 8/2009 | Hill et al. |
| 2009/0220612 A1* | 9/2009 | Perera ........................... 424/497 |
| 2009/0259300 A1 | 10/2009 | Dorogy, Jr. et al. |
| 2009/0264975 A1 | 10/2009 | Flanagan et al. |
| 2009/0281613 A1* | 11/2009 | Atanasoska et al. ......... 623/1.15 |
| 2009/0287301 A1* | 11/2009 | Weber .......................... 623/1.46 |

| | | |
|---|---|---|
| 2009/0306765 A1* | 12/2009 | Weber .................. 623/1.15 |
| 2009/0317766 A1 | 12/2009 | Heidenau et al. |
| 2010/0008970 A1* | 1/2010 | O'Brien et al. ............. 424/426 |
| 2010/0030326 A1* | 2/2010 | Radhakrishnan et al. ... 623/1.46 |
| 2010/0042206 A1 | 2/2010 | Yadav et al. |
| 2010/0057197 A1* | 3/2010 | Weber et al. ................ 623/1.42 |
| 2010/0070022 A1 | 3/2010 | Kuehling |
| 2010/0070026 A1 | 3/2010 | Ito et al. |
| 2010/0131050 A1 | 5/2010 | Zhao |

FOREIGN PATENT DOCUMENTS

| | | |
|---|---|---|
| AT | 288234 | 2/2005 |
| AU | 4825696 | 10/1996 |
| AU | 5588896 | 12/1996 |
| AU | 5266698 | 6/1998 |
| AU | 6663298 | 9/1998 |
| AU | 716005 | 2/2000 |
| AU | 5686499 | 3/2000 |
| AU | 2587100 | 5/2000 |
| AU | 2153600 | 6/2000 |
| AU | 1616201 | 5/2001 |
| AU | 737252 | 8/2001 |
| AU | 2317701 | 8/2001 |
| AU | 5215401 | 9/2001 |
| AU | 5890401 | 12/2001 |
| AU | 3597401 | 6/2002 |
| AU | 2002353068 | 3/2003 |
| AU | 2002365875 | 6/2003 |
| AU | 2003220153 | 9/2003 |
| AU | 2003250913 | 1/2004 |
| AU | 770395 | 2/2004 |
| AU | 2003249017 | 2/2004 |
| AU | 2003256499 | 2/2004 |
| AU | 771367 | 3/2004 |
| AU | 2003271633 | 4/2004 |
| AU | 2003272710 | 4/2004 |
| AU | 2003285195 | 6/2004 |
| AU | 2003287633 | 6/2004 |
| AU | 2003290675 | 6/2004 |
| AU | 2003290676 | 6/2004 |
| AU | 2003291470 | 6/2004 |
| AU | 2003295419 | 6/2004 |
| AU | 2003295535 | 6/2004 |
| AU | 2003295763 | 6/2004 |
| AU | 2004202073 | 6/2004 |
| AU | 2003300323 | 7/2004 |
| AU | 2004213021 | 9/2004 |
| AU | 2003293557 | 1/2005 |
| AU | 780539 | 3/2005 |
| BR | 8701135 | 1/1988 |
| BR | 0207321 | 2/2004 |
| BR | 0016957 | 6/2004 |
| BR | 0316065 | 9/2005 |
| BR | 0316102 | 9/2005 |
| CA | 1283505 | 4/1991 |
| CA | 2172187 | 10/1996 |
| CA | 2178541 | 12/1996 |
| CA | 2234787 | 10/1998 |
| CA | 2235031 | 10/1998 |
| CA | 2238837 | 2/1999 |
| CA | 2340652 | 3/2000 |
| CA | 2392006 | 5/2001 |
| CA | 2337565 | 8/2001 |
| CA | 2409862 | 11/2001 |
| CA | 2353197 | 1/2002 |
| CA | 2429356 | 8/2002 |
| CA | 2435306 | 8/2002 |
| CA | 2436241 | 8/2002 |
| CA | 2438095 | 8/2002 |
| CA | 2460334 | 3/2003 |
| CA | 2425665 | 4/2003 |
| CA | 2465704 | 4/2003 |
| CA | 2464906 | 5/2003 |
| CA | 2468677 | 6/2003 |
| CA | 2469744 | 6/2003 |
| CA | 2484383 | 1/2004 |
| CA | 2497602 | 4/2004 |
| CA | 2499976 | 4/2004 |
| CA | 2503625 | 5/2004 |
| CA | 2504524 | 5/2004 |
| CA | 2505576 | 5/2004 |
| CA | 2513721 | 5/2004 |
| CA | 2505080 | 6/2004 |
| CA | 2506622 | 6/2004 |
| CA | 2455670 | 7/2004 |
| CA | 2508247 | 7/2004 |
| CA | 2458172 | 8/2004 |
| CA | 2467797 | 11/2004 |
| CA | 2258898 | 1/2005 |
| CA | 2308177 | 1/2005 |
| CA | 2475968 | 1/2005 |
| CA | 2489668 | 6/2005 |
| CA | 2490170 | 6/2005 |
| CA | 2474367 | 1/2006 |
| CA | 2374090 | 5/2007 |
| CA | 2282748 | 11/2007 |
| CA | 2336650 | 1/2008 |
| CA | 2304325 | 5/2008 |
| CN | 1430491 | 7/2003 |
| CN | 1547490 | 11/2004 |
| CN | 1575154 | 2/2005 |
| CN | 1585627 | 2/2005 |
| CN | 1669537 | 9/2005 |
| DE | 3516411 | 11/1986 |
| DE | 3608158 | 9/1987 |
| DE | 19916086 | 10/1999 |
| DE | 19855421 | 5/2000 |
| DE | 19916315 | 9/2000 |
| DE | 9422438 | 4/2002 |
| DE | 1096902 | 5/2002 |
| DE | 10064596 | 6/2002 |
| DE | 10107339 | 9/2002 |
| DE | 69712063 | 10/2002 |
| DE | 10127011 | 12/2002 |
| DE | 10150995 | 4/2003 |
| DE | 69807634 | 5/2003 |
| DE | 69431457 | 6/2003 |
| DE | 10200387 | 8/2003 |
| DE | 69719161 | 10/2003 |
| DE | 02704283 | 4/2004 |
| DE | 60106962 | 4/2005 |
| DE | 60018318 | 12/2005 |
| DE | 69732439 | 1/2006 |
| DE | 69828798 | 1/2006 |
| DE | 102004044738 | 3/2006 |
| DE | 69830605 | 5/2006 |
| DE | 102005010100 | 9/2006 |
| DE | 602005001867 | 5/2008 |
| DE | 69829015 | 3/2009 |
| DK | 127987 | 9/1987 |
| DK | 914092 | 8/2002 |
| EP | 0222853 | 5/1987 |
| EP | 0129147 | 1/1990 |
| EP | 0734721 | 10/1996 |
| EP | 0650604 | 9/1998 |
| EP | 0865762 | 9/1998 |
| EP | 0875217 | 11/1998 |
| EP | 0633840 | 11/1999 |
| EP | 0953320 | 11/1999 |
| EP | 0971644 | 1/2000 |
| EP | 0982041 | 3/2000 |
| EP | 1105169 | 6/2001 |
| EP | 1124594 | 8/2001 |
| EP | 1127582 | 8/2001 |
| EP | 1131127 | 9/2001 |
| EP | 1132058 | 9/2001 |
| EP | 1150738 | 11/2001 |
| EP | 1172074 | 1/2002 |
| EP | 1181943 | 2/2002 |
| EP | 0914092 | 4/2002 |
| EP | 1216665 | 6/2002 |
| EP | 0747069 | 9/2002 |
| EP | 0920342 | 9/2002 |
| EP | 1242130 | 9/2002 |
| EP | 0623354 | 10/2002 |
| EP | 0806211 | 10/2002 |
| EP | 1275352 | 1/2003 |
| EP | 0850604 | 2/2003 |

| | | | | | | |
|---|---|---|---|---|---|---|
| EP | 1280512 | 2/2003 | | EP | 1441667 | 1/2007 |
| EP | 1280568 | 2/2003 | | EP | 1192957 | 2/2007 |
| EP | 1280569 | 2/2003 | | EP | 1236447 | 2/2007 |
| EP | 1294309 | 3/2003 | | EP | 1764116 | 3/2007 |
| EP | 0824900 | 4/2003 | | EP | 1185215 | 4/2007 |
| EP | 1308179 | 5/2003 | | EP | 1442757 | 4/2007 |
| EP | 1310242 | 5/2003 | | EP | 1786363 | 5/2007 |
| EP | 1314405 | 5/2003 | | EP | 1787602 | 5/2007 |
| EP | 1316323 | 6/2003 | | EP | 1788973 | 5/2007 |
| EP | 1339448 | 9/2003 | | EP | 1796754 | 6/2007 |
| EP | 1347791 | 10/2003 | | EP | 1330273 | 7/2007 |
| EP | 1347792 | 10/2003 | | EP | 0900060 | 8/2007 |
| EP | 1348402 | 10/2003 | | EP | 1355588 | 8/2007 |
| EP | 1348405 | 10/2003 | | EP | 1355589 | 8/2007 |
| EP | 1359864 | 11/2003 | | EP | 1561436 | 8/2007 |
| EP | 1365710 | 12/2003 | | EP | 1863408 | 12/2007 |
| EP | 1379290 | 1/2004 | | EP | 1071490 | 1/2008 |
| EP | 0902666 | 2/2004 | | EP | 1096902 | 1/2008 |
| EP | 1460972 | 2/2004 | | EP | 0895762 | 2/2008 |
| EP | 0815806 | 3/2004 | | EP | 0916317 | 2/2008 |
| EP | 1400219 | 3/2004 | | EP | 1891988 | 2/2008 |
| EP | 0950386 | 4/2004 | | EP | 1402849 | 4/2008 |
| EP | 1461165 | 4/2004 | | EP | 1466634 | 7/2008 |
| EP | 1416884 | 5/2004 | | EP | 1572032 | 7/2008 |
| EP | 1424957 | 6/2004 | | EP | 1527754 | 8/2008 |
| EP | 1429816 | 6/2004 | | EP | 1968662 | 9/2008 |
| EP | 1448116 | 8/2004 | | EP | 1980223 | 10/2008 |
| EP | 1448118 | 8/2004 | | EP | 1988943 | 11/2008 |
| EP | 1449545 | 8/2004 | | EP | 1490125 | 1/2009 |
| EP | 1449546 | 8/2004 | | EP | 1829626 | 2/2009 |
| EP | 1254674 | 9/2004 | | EP | 1229901 | 3/2009 |
| EP | 1453557 | 9/2004 | | EP | 1128785 | 4/2009 |
| EP | 1457214 | 9/2004 | | EP | 2051750 | 4/2009 |
| EP | 1476882 | 9/2004 | | EP | 1427353 | 5/2009 |
| EP | 0975340 | 10/2004 | | ES | 2169012 | 7/2002 |
| EP | 1319416 | 11/2004 | | FR | 2867059 | 9/2005 |
| EP | 1479402 | 11/2004 | | GB | 2397233 | 7/2004 |
| EP | 1482867 | 12/2004 | | JP | 7002180 | 1/1995 |
| EP | 1011529 | 1/2005 | | JP | 3673973 | 2/1996 |
| EP | 0875218 | 2/2005 | | JP | 3249383 | 10/1996 |
| EP | 1181903 | 2/2005 | | JP | 3614652 | 11/1998 |
| EP | 1504775 | 2/2005 | | JP | 10295824 | 11/1998 |
| EP | 1042997 | 3/2005 | | JP | 11188109 | 7/1999 |
| EP | 1754684 | 3/2005 | | JP | 2000312721 | 11/2000 |
| EP | 1520594 | 4/2005 | | JP | 2001098308 | 4/2001 |
| EP | 1521603 | 4/2005 | | JP | 2001522640 | 11/2001 |
| EP | 1028672 | 6/2005 | | JP | 2002065862 | 3/2002 |
| EP | 1539041 | 6/2005 | | JP | 2002519139 | 7/2002 |
| EP | 1543798 | 6/2005 | | JP | 2002523147 | 7/2002 |
| EP | 1550472 | 6/2005 | | JP | 2003024449 | 1/2003 |
| EP | 1328213 | 7/2005 | | JP | 2003521274 | 7/2003 |
| EP | 1551569 | 7/2005 | | JP | 2003290361 | 10/2003 |
| EP | 1554992 | 7/2005 | | JP | 2003533333 | 11/2003 |
| EP | 1560613 | 8/2005 | | JP | 2004500925 | 1/2004 |
| EP | 1562519 | 8/2005 | | JP | 2004522559 | 7/2004 |
| EP | 1562654 | 8/2005 | | JP | 2004223264 | 8/2004 |
| EP | 1570808 | 9/2005 | | JP | 2004267750 | 9/2004 |
| EP | 1575631 | 9/2005 | | JP | 2004275748 | 10/2004 |
| EP | 1575638 | 9/2005 | | JP | 2004305753 | 11/2004 |
| EP | 1575642 | 9/2005 | | JP | 2005501654 | 1/2005 |
| EP | 0900059 | 10/2005 | | JP | 2005502426 | 1/2005 |
| EP | 1581147 | 10/2005 | | JP | 2005040584 | 2/2005 |
| EP | 1586286 | 10/2005 | | JP | 2005503184 | 2/2005 |
| EP | 1254673 | 11/2005 | | JP | 2005503240 | 2/2005 |
| EP | 1261297 | 11/2005 | | JP | 2005507285 | 3/2005 |
| EP | 0927006 | 1/2006 | | JP | 2005511139 | 4/2005 |
| EP | 1621603 | 2/2006 | | JP | 2005511242 | 4/2005 |
| EP | 1218665 | 5/2006 | | JP | 2005131364 | 5/2005 |
| EP | 1222941 | 5/2006 | | JP | 2005152526 | 6/2005 |
| EP | 1359867 | 5/2006 | | JP | 2005152527 | 6/2005 |
| EP | 1656961 | 5/2006 | | JP | 2005199054 | 7/2005 |
| EP | 1277449 | 6/2006 | | JP | 2005199058 | 7/2005 |
| EP | 0836839 | 7/2006 | | JP | 2008516726 | 5/2008 |
| EP | 1684817 | 8/2006 | | KR | 20027462 | 8/2002 |
| EP | 1687042 | 8/2006 | | KR | 2003/0003465 | 7/2004 |
| EP | 0907339 | 11/2006 | | KR | 2005/0117361 | 12/2005 |
| EP | 1359865 | 11/2006 | | NZ | 331388 | 1/2000 |
| EP | 1214108 | 1/2007 | | SU | 393044 | 12/1973 |
| EP | 1416885 | 1/2007 | | WO | WO86/06617 | 11/1986 |

| | | | | | | |
|---|---|---|---|---|---|---|
| WO | WO93/06792 | 4/1993 | | WO | WO03/083181 | 10/2003 |
| WO | WO93/07934 | 4/1993 | | WO | WO03/094774 | 11/2003 |
| WO | WO93/16656 | 9/1993 | | WO | WO2004/004602 | 1/2004 |
| WO | WO94/16646 | 8/1994 | | WO | WO2004/004603 | 1/2004 |
| WO | WO95/03083 | 2/1995 | | WO | WO2004/006491 | 1/2004 |
| WO | WO96/04952 | 2/1996 | | WO | WO2004/006807 | 1/2004 |
| WO | WO96/09086 | 3/1996 | | WO | WO2004/006976 | 1/2004 |
| WO | WO96/32907 | 10/1996 | | WO | WO2004/006983 | 1/2004 |
| WO | WO97/41916 | 11/1997 | | WO | WO2004/010900 | 2/2004 |
| WO | WO98/17331 | 4/1998 | | WO | WO2004/014554 | 2/2004 |
| WO | WO98/18408 | 5/1998 | | WO | WO2004/026177 | 4/2004 |
| WO | WO98/23228 | 6/1998 | | WO | WO2004/028347 | 4/2004 |
| WO | WO98/36784 | 8/1998 | | WO | WO2004/028587 | 4/2004 |
| WO | WO98/38946 | 9/1998 | | WO | WO2004/043292 | 5/2004 |
| WO | WO98/38947 | 9/1998 | | WO | WO2004/043298 | 5/2004 |
| WO | WO98/40033 | 9/1998 | | WO | WO2004/043300 | 5/2004 |
| WO | WO98/57680 | 12/1998 | | WO | WO2004/043509 | 5/2004 |
| WO | WO99/16386 | 4/1999 | | WO | WO2004/043511 | 5/2004 |
| WO | WO99/23977 | 5/1999 | | WO | WO2004/045464 | 6/2004 |
| WO | WO99/42631 | 8/1999 | | WO | WO2004/045668 | 6/2004 |
| WO | WO99/49928 | 10/1999 | | WO | WO2004/058100 | 7/2004 |
| WO | WO99/52471 | 10/1999 | | WO | WO2004/060428 | 7/2004 |
| WO | WO99/62432 | 12/1999 | | WO | WO2004/064911 | 8/2004 |
| WO | WO00/01322 | 1/2000 | | WO | WO2004/071548 | 8/2004 |
| WO | WO00/10622 | 3/2000 | | WO | WO2004/072104 | 8/2004 |
| WO | WO00/25841 | 5/2000 | | WO | WO2004/073768 | 9/2004 |
| WO | WO00/27303 | 5/2000 | | WO | WO2004/080579 | 9/2004 |
| WO | WO00/30710 | 6/2000 | | WO | WO2004/087251 | 10/2004 |
| WO | WO00/48660 | 8/2000 | | WO | WO2004/096176 | 11/2004 |
| WO | WO00/64506 | 11/2000 | | WO | WO2004/105639 | 12/2004 |
| WO | WO01/35928 | 5/2001 | | WO | WO2004/108021 | 12/2004 |
| WO | WO01/41827 | 6/2001 | | WO | WO2004/108186 | 12/2004 |
| WO | WO01/45862 | 6/2001 | | WO | WO2004/108346 | 12/2004 |
| WO | WO01/45763 | 7/2001 | | WO | WO2004/110302 | 12/2004 |
| WO | WO01/66036 | 9/2001 | | WO | WO2005/004754 | 1/2005 |
| WO | WO01/80920 | 11/2001 | | WO | WO2005/006325 | 1/2005 |
| WO | WO01/87263 | 11/2001 | | WO | WO2005/011529 | 2/2005 |
| WO | WO01/87342 | 11/2001 | | WO | WO2005/014892 | 2/2005 |
| WO | WO01/87374 | 11/2001 | | WO | WO2005/027794 | 3/2005 |
| WO | WO01/89417 | 11/2001 | | WO | WO2005/032456 | 4/2005 |
| WO | WO01/89420 | 11/2001 | | WO | WO2005/034806 | 4/2005 |
| WO | WO02/26162 | 4/2002 | | WO | WO2005/042049 | 5/2005 |
| WO | WO02/30487 | 4/2002 | | WO | WO2005/044361 | 5/2005 |
| WO | WO02/38827 | 5/2002 | | WO | WO2005/049520 | 6/2005 |
| WO | WO02/42521 | 5/2002 | | WO | WO2005/051450 | 6/2005 |
| WO | WO02/43796 | 6/2002 | | WO | WO2005/053766 | 6/2005 |
| WO | WO02/47581 | 6/2002 | | WO | WO2005/063318 | 7/2005 |
| WO | WO02/058753 | 8/2002 | | WO | WO2005/072437 | 8/2005 |
| WO | WO02/060349 | 8/2002 | | WO | WO2005/082277 | 9/2005 |
| WO | WO02/060350 | 8/2002 | | WO | WO2005/082283 | 9/2005 |
| WO | WO02/060506 | 8/2002 | | WO | WO2005/086733 | 9/2005 |
| WO | WO02/064019 | 8/2002 | | WO | WO2005/089825 | 9/2005 |
| WO | WO02/065947 | 8/2002 | | WO | WO2005/091834 | 10/2005 |
| WO | WO02/069848 | 9/2002 | | WO | WO2005/099621 | 10/2005 |
| WO | WO02/074431 | 9/2002 | | WO | WO2005/099626 | 10/2005 |
| WO | WO02/076525 | 10/2002 | | WO | WO2005/110285 | 11/2005 |
| WO | WO02/078668 | 10/2002 | | WO | WO2005/115276 | 12/2005 |
| WO | WO02/083039 | 10/2002 | | WO | WO2005/115496 | 12/2005 |
| WO | WO02/085253 | 10/2002 | | WO | WO2005/117752 | 12/2005 |
| WO | WO02/085424 | 10/2002 | | WO | WO2006/014969 | 2/2006 |
| WO | WO02/085532 | 10/2002 | | WO | WO2006/015161 | 2/2006 |
| WO | WO02/096389 | 12/2002 | | WO | WO2006/020742 | 2/2006 |
| WO | WO03/009779 | 2/2003 | | WO | WO2006/029364 | 3/2006 |
| WO | WO03/022178 | 3/2003 | | WO | WO2006/029708 | 3/2006 |
| WO | WO03/024357 | 3/2003 | | WO | WO2006/036801 | 4/2006 |
| WO | WO03/026713 | 4/2003 | | WO | WO2006/055237 | 5/2006 |
| WO | WO03/035131 | 5/2003 | | WO | WO2006/061598 | 6/2006 |
| WO | WO03/037220 | 5/2003 | | WO | WO2006/063157 | 6/2006 |
| WO | WO03/037221 | 5/2003 | | WO | WO2006/063158 | 6/2006 |
| WO | WO03/037223 | 5/2003 | | WO | WO2006/083418 | 8/2006 |
| WO | WO03/037398 | 5/2003 | | WO | WO2006/104644 | 10/2006 |
| WO | WO03/039407 | 5/2003 | | WO | WO2006/104976 | 10/2006 |
| WO | WO03/045582 | 6/2003 | | WO | WO2006/105256 | 10/2006 |
| WO | WO03/047463 | 6/2003 | | WO | WO2006/107677 | 10/2006 |
| WO | WO03/051233 | 6/2003 | | WO | WO2006/116752 | 11/2006 |
| WO | WO03/055414 | 7/2003 | | WO | WO2006/124365 | 11/2006 |
| WO | WO03/061755 | 7/2003 | | WO | WO2007/016961 | 2/2007 |
| WO | WO03/072287 | 9/2003 | | WO | WO2007/034167 | 3/2007 |
| WO | WO03/077802 | 9/2003 | | WO | WO2007/070666 | 6/2007 |

| | | |
|---|---|---|
| WO | WO2007/095167 | 8/2007 |
| WO | WO2007/124137 | 11/2007 |
| WO | WO2007/126768 | 11/2007 |
| WO | WO2007/130786 | 11/2007 |
| WO | WO2007/133520 | 11/2007 |
| WO | WO2007/143433 | 12/2007 |
| WO | WO2007/145961 | 12/2007 |
| WO | WO2007/147246 | 12/2007 |
| WO | WO2008/002586 | 1/2008 |
| WO | WO2008/002778 | 1/2008 |
| WO | WO2008/024149 | 2/2008 |
| WO | WO2008/024477 | 2/2008 |
| WO | WO2008/024669 | 2/2008 |
| WO | WO2008/033711 | 3/2008 |
| WO | WO2008/034048 | 3/2008 |
| WO | WO2008/036549 | 3/2008 |
| WO | WO2008/039319 | 4/2008 |
| WO | WO2008/045184 | 4/2008 |
| WO | WO2008/057991 | 5/2008 |
| WO | WO2008/061017 | 5/2008 |
| WO | WO2008/063539 | 5/2008 |
| WO | WO2008/082698 | 7/2008 |
| WO | WO2008/106223 | 9/2008 |
| WO | WO2008/108987 | 9/2008 |
| WO | WO2008/124513 | 10/2008 |
| WO | WO2008/124519 | 10/2008 |
| WO | WO2008/140482 | 11/2008 |
| WO | WO2008/147848 | 12/2008 |
| WO | WO2008/147853 | 12/2008 |
| WO | WO2009/009627 | 1/2009 |
| WO | WO2009/009628 | 1/2009 |
| WO | WO2009/012353 | 1/2009 |
| WO | WO2009/014692 | 1/2009 |
| WO | WO2009/014696 | 1/2009 |
| WO | WO2009/020520 | 2/2009 |
| WO | WO2009/059081 | 5/2009 |
| WO | WO2009/059085 | 5/2009 |
| WO | WO2009/059086 | 5/2009 |
| WO | WO2009/059098 | 5/2009 |
| WO | WO2009/059129 | 5/2009 |
| WO | WO2009/059141 | 5/2009 |
| WO | WO2009/059146 | 5/2009 |
| WO | WO2009/059165 | 5/2009 |
| WO | WO2009/059166 | 5/2009 |
| WO | WO2009/059180 | 5/2009 |
| WO | WO2009/059196 | 5/2009 |
| WO | WO2009/089382 | 7/2009 |
| WO | WO2009/091384 | 7/2009 |
| WO | WO2009/094270 | 7/2009 |
| WO | WO2009/126766 | 10/2009 |
| ZA | 9710342 | 6/1998 |

OTHER PUBLICATIONS

U.S. Appl. No. 11/752,772, filed May 23, 2007, Scheuermann et al.
U.S. Appl. No. 60/845,136, filed Sep. 15, 2006, Weber et al.
U.S. Appl. No. 60/857,849, Weber et al.
Nanoparticle Coatings, available from http://www.mantisdeposition.com (downloaded from the Internet on Jan. 10, 2007) Mantis Deposition Ltd., England.
A.H. Kean et al. "The Analysis of Coatings Produced by Accelerated Nanoparticles" *Mantis Deposition Ltd., NSTI Nano Tech 2006*, Boston, May 7-11, 2006.
J. Kraft et al., "Thin films from fast clusters: golden TiN layers on a room temperature substrate" *Surface and Coatings Technology* 158-159: pp. 131-135 (2002).
Y. Qiang et al., "Hard coatings (TiN, $Ti_xAl_{1-x}N$) deposited at room temperature by energetic cluster impact" *Surface and Coatings Technology* 100-101:pp. 27-32 (1998).
Schetsky, L. McDonald, "Shape Memory Alloys", Encyclopedia of Chemical Technology (3rd ed.), John Wiley & Sons, vol. 20:pp. 726-736 (1982).
International Preliminary Report on Patentability, issued in the PCT application PCT/US2007/084286, filed on Nov. 9, 2001.
U.S Appl. No. 11/694,436, filed Mar. 30, 2007, Atanasoska et al.
"Cyclic voltammetry"from Wikipedia, (http://en.wikipedia.org/wiki/Cyclic_voltammetry) (downloaded [2007]).
"Electrophoretic deposition"from Wikipedia, (http://en.wikipedia.org/wiki/electrophoretic_deposition) (downloaded [2007]).
"Impressive Progress In Interventional Cardiology—From 1st Balloon Inflation To First Bioabsorbable Stent," Medical News Today, May 15, 2006, (http://www.medicalnewstoday.com/articles/43313.php).
"JOMED Starts Clinical Studies on Tacrolimus-Eluting Coronary Stents," Jomed Press Release, 2 pages, Jan. 14, 2002.
"Nano PLD," PVD Products, Inc. Wilmington, Ma, (2003).
"Sputtering," Wikipedia.com, (http://en.wikipedia.org/wiki/Sputtering) (downloaded [2009]).
"Ultraviolet-Ozone Surface Treatment," Three Bond Technical News #17, pp. 1-10, Issued Mar. 20, 1987, (http://www.threebond.co.jp/en/technical/technicalnews/pdf/tech17.pdf).
Abbott et al., "Voltammetric and impedance studies of the electropolishing of type 316 stainless steel in a choline chloride based ionic liquid," Electrochimica Acta, vol. 51, pp. 4420-4425, (2006).
Abstract: "Edelstahlfreier stent aus niobium mit iridiumoxyd (IrOx)-beschichtung: Erste Ergebnisse der LUSTY-studie", (Stainless steel-free Stent out of niobium with iridiumoxyd (IrOx)-coating: Initial results of the LUSTY-study), Annual Meeting of the German Society for Cardiology, Apr. 24-26, 2003.
Adanur et al., "Nanocomposite Fiber Based Web and Membrane Formation and Characterization," Journal of Industrial Textiles, vol. 36, No. 4, pp. 311-327, Apr. 2007.
Advincula et al., "Surface modification of surface sol-gel derived titanium oxide films by self-assembled monolayers (SAMs) and non-specific protein adsorption studies," Colloids and Surfaces B: Biointerfaces, vol. 42, pp. 29-43, (2005).
Akhras, "Bare metal stent, lunar IrOx2 coated or drug-eluting stent for patients with CAD?", PowerPoint presentation, Oct., 2006.
Akhras, Comparison of Iridiumoxide Coated Stent with Paclitaxel-Eluting Stent and a Bare Metal Stent in Patients With Coronary Artery Disease; Abstract, Oct. 2006.
Al-Lamee, "Programmable Elution Profile Coating for Drug-Eluting Stents," Medical Device Technology: Materials, pp. 12-15, Mar. 2005.
Amanatides et al., "Electrical and optical properties of $CH_4/H_2$ RF plasmas for diamond-like thin film deposition," Diamond & Related materials, vol. 14, pp. 292-295, (2005).
Amberg et al., "Silver Deposition on Temperature Sensitive Substrates by Means of an Inverted Cylindrical Magnetron," Poster, 2003.
Anders, "Ion Plating and Beyond: Pushing the Limits of Energetic Deposition," Vacuum Technology & Coating, pp. 41-46, Dec. 2002.
Andersson et al., "Influence of Systematically Varied Nanoscale Topography on the Morphology of Epithelial Cells," IEEE Transactions on Nanobioscience, vol. 2, No. 2, pp. 49-57, Jun. 2003.
Andersson et al., "Nanoscale features influence epithelial cell morphology and cytokine production," Biomaterials, 2003. vol. 24, No. 20, pp. 3427-3436, (2003).
Annis et al., "An Elastomeric Vascular Prosthesis," Transactions—American Society for Artificial Internal Organs. vol. XXIV, pp. 209-214, (1978).
Ansell et al., "X-Ray Rhotoelectron Spectroscopic Studies of Tin Electrodes after Polarization in Sodium Hydroxide Solution," Journal of Electrochemical Society: Electrochemical Science and Technology, vol. 124, No. 9, pp. 1360-1364, Sep. 1977.
Antunes et al., "Characterization of Corrosion Products Formed on Steels in the First Months of Atmospheric Exposure", Materia, vol. 8, No. 1, pp. 27-34, (2003).
Armani et al., "Microfabrication Technology for Polycaprolactone, a Biodegradable Polymer," Journal of Micromechanics and Microengineering, vol. 10, pp. 80-84, (2000).
Arnold et al., "Activation of Integrin Function by Nanopatterned Adhesive Interface," ChemPhysChem, vol. 5, pp. 383-388, (2004).
Ashfold et al., "Pulsed laser ablation and deposition of thin films," Chem. Soc. Rev., vol. 33, pp. 23-31, (2004).
Asoh et al., "Conditions for Fabrication of Ideally Ordered Anodic Porous Alumina Using Pretextured A1," Journal of the Electrochemical Society, vol. 148, pp. B152-B156, (2001).

Atanasoska et al., "XPS Studies on Conducting Polymers: Polypyrrole Films Doped with Perchlorate and Polymeric Anions," Chemistry Materials vol. 4, pp. 988-994, (1992).

Aughenbaugh et al., "Silica sol-gel for the controlled release of antibiotics. II. The effect of synthesis parameters on the in vitro release kinetics of vancomycin," Journal of Biomedical Materials Research, vol. 57, No. 3, pp. 321-326, Dec. 5, 2001.

Awad et al., "Deposition of duplex $Al_2O_3$/TiN coatings on aluminum alloys for tribological applications using a combined microplasma oxidation (MPO) and arc ion plating (AIP)," Wear, vol. 260, pp. 215-222, (2006).

AxynTec product review, AxynTec Dunnschichttechnik GmbH (www.axyntec.de) (2002).

Ayon et al., "Drug loading of nonopouros $TiO_2$ films," Institute of Physics Publishing, Biomedical Materials, vol. 1, pp. L11-L15, (2006).

Azom, "Porous Coatings for Improved Implant Life—Total Hip Replacements," [downloaded Sep. 1, 2005], (http://www.azom.com/Details.asp?ArticleID=1900).

Bak et al., "Electrodeposition of polymer next to the three-phase boundary," Electrochemisty Communications, vol. 7, pp. 1098-1104, (2005).

Balamuguran et al., "Bioactive Sol-Gel Hydroxyapatite Surface for Biomedical Applications-In Vitro Study," Trends in Biomaterials & Artificial Organs, vol. 16, No. 1, pp. 18-20, (2002).

Balas et al., "Formation of Bone-Like Apatite on Organic Polymers Treated with a Silane-Coupling Agent and a Titania Solution," Biomaterials, vol. 27, pp. 1704-1710, (2006).

Balaur et al., "Tailoring the wettability of $TiO_2$ nanotube layers," Electrochemistry Communications, vol. 7, pp. 1066-1070, (2005).

Banks et al., "Femtosecond Laser-Induced Forward Transfer (LIFT): A Technique for Versatile Micro-Printing Applications," European Conference on Lasers and Electro-Optics and the International Quantum Electronics Conference, Jun. 17-22, 2007.

Banks et al., "Nano-droplets Deposited in Microarrays by Femtosecond Ti: Saphire Laser-Induced Forward Transfer," Optoelectronics Reaserch Centre, University of Southhampton, Applied Physics Letters, vol. 89, Issue 19, (2006).

Barbucci et al, Micro and nano-structured surfaces,: Journal Of Materials Science: Materials In Medicine, vol. 14, No. 8, pp. 721-725, (2003).

Bates et al. "Description of research activites: Block copolymers," Organization for Minnesota Nanotechnology Institute, University of Minnesota, (2002).

Bayoumi et al., "Formation of self-organized titania nano-tubes by dealloying and anodic oxidation," Electrochemistry Communications, vol. 8, pp. 38-44, (2006).

Békési et al., "Efficient Submicron Processing of Metals with Femtosecond UV Pulses," Applied Physics A, vol. 76, pp. 355-357 (2003).

Benson, "Drug Delivery Technology and Access," Polygenetics, Inc., pp. 1-10, Oct. 2005.

Benson, "Highly Porous Polymers," American Laboratory, pp. 1-14, Apr. 2003.

Berg et al., "Controlled Drug Release from Porous Polyelectrolyte Multilayers," Biomacromolecules, vol. 7, pp. 357-364, (2006).

Berkland et al., "Controlling surface nano-structure using flow-limited field-injection electrostatic spraying (FFESS) of poly(D,L-lactide-co-glycolide)," Biomaterials, vol. 25, pp. 5649-5658, (2004).

Berry et al., "The fibroblast response to tubes exhibiting internal nanotopography," Biomaterials, vol. 26, No. 24, pp. 4985-4992, (2005).

Biederman et al. "Plasma Polymer-Metal Composite Films," Plasma Deposition, Treatment and Etching of Polymers, pp. 269-320, (1990).

Bock et al., "Anion and water involvement in hydrous Ir oxide redox reactions in acidic solutions," Journal of Electroanalytical Chemistry, vol. 475, pp. 20-27, (1999).

Bolle et al., "Characterization of submicrometer periodic structures produced on polymer surfaces with low-fluence ultraviolet laser radiation," Journal of Applied Physics, vol. 73, No. 7, pp. 3516-3524, Apr. 1, 1993.

Bolzán et al., "The Potentiodynamic behaviour of iridium electrodes in aqueous 3.7 M $H_2SO_4$ in the 293-195 K Range," Journal of Electroanalytical Chemistry, vol. 461, pp. 40-51, (1999).

Boulmedais et la., "Controlled Electrodissolution of Polyelectrolyte Multilayers: A Platform Technology Towards the Surface-Initiated Delivery of Drugs," Advanced Functional Materials, vol. 63, pp. 63-70, (2006).

Boura et al., "Endothelial cell—interactions with polyelectrolyte multilayer films," Biomaterials, vol. 26. pages 4568-4575, (2005).

Bradley et al., "Visuotopic Mapping Through a Multichannel Stimulating Implant in Primate V1," Journal of Neurophysiology, vol. 93, pp. 1659-1670, (2005).

Bretagnol et al., "Functional Micropatterning Surface by Combination of Plasma Polymerization and Lift-Off Process," Plasma Process and Polymers, vol. 3, pp. 30-38, Nov. 14, 2005.

Bretagnol et al., "Surface Functionalization and Patterning Techniques to Design Interfaces for Biomedical and Biosensor Applications," Plasma Processes and Polymers, vol. 3, pp. 443-455, (2006).

Brody et al., "Characterization Nanoscale topography of the Aortic Heart Valve Basement Membrane for Tissue Engineering Heart Valve Scaffold Design," Tissue Engineering, vol. 12, No. 2, pp. 413-421, Nov. 2, 2006.

Brukner et al., "Metal plasma immersion ion implantation and deposition (MPIIID): chromium on magnesium," Surface and Coatings Technology vol. 103-104, pp. 227-230, (1998).

Brunetti et al., "Oxide/hydroxide films on tin. Part I: Kinetic aspects of the electroformation and electroreductions of the films," Journal of Electroanalytical Chemisty, (2007).

Bu et al., "Preparation of nanocrystalline TiO2 porour films from terpineol-ethanol-PEG system," Journal of Materials Science, vol. 41, pp. 2067-2073, (2006).

Bu et al., "Synthesis of $TiO_2$ Porous Thin Films by Polythylene Glycol Templating and Chemistry of the Process," Journal of the European Ceramic Society, vol. 25, pp. 673-679 (2005).

Burmeister et al., "Colloid Monolayers as Versatile Lithographic Masks," Langmuir, vol. 13, pp. 2983-2987, (1997).

Buster et al., "Crystal habits of the Magnesium Hydroxide mineral Brucite within Coral Skeletons," American Geophysical Union Annual Meeting, Abstract and Poster, (2006).

Buttiglieri et al., "Endothelization and adherence of leucocytes to nanostructured surfaces," Biomaterials, vol. 24, pp. 2731-2738, (2003).

Calcagno et al., "Structural modification of polymer films by ion irradiation," Nuclear Instruments and Methods in Physics Research, vol. B65, pp. 413-422, (1992).

Carp et al., "Photoinduced Reactivity of Titanium Dioxide," Progress in Solid State Chemistry, vol. 32, pp. 33-177, (2004).

Caruso, "Nanoscale Particle Modifications via Sequential Electrostatic Assembly," Colloids and Colloid Assemblies: Synthesis, Modification, Organization and Utilization of Colloid Particles, pp. 266-269, Mar. 19, 2004.

Cassak, "ART: Bucking the Trend in Bioabsorbable Stents", Windhover Information Inc., In Vivo Jun. 2008.

Catledge et al, "Structure and Mechanical Properties of Functionally-Graded Nanostructured Metalloceramic Coatings," Mat. Res. Soc. Symp. Proc. vol. 778, pp. U7.8.1-U7.8.6, (2003).

Catledge et al., "Structural and mechanical properties of nanostructured metalloceramic coatings on colbalt chrome alloys," Applied Physics Letters, vol. 82, No. 10, pp. 1625-1627, Mar. 10, 2003.

Caves et al., "The evolving impact of microfabrication and nanotechnology on stent design," Journal of Vascular Surgery, pp. 1363-1368, Dec. 2006.

Caves et al., "The evolving impact of microfabrication and nanotechnology on stent design," Journal of Vascular Surgury, vol. 44, pp. 1363-1368, (2006).

Cernigoj et al., "Photocatalytically Active TiO2 Thin Films Produced by Surfactant-Assistant Sol-Gel Processing," Thin Solid Films, vol. 495, pp. 327-332, (2006).

Ceruti et al., "Preparation, characterization, cytotoxicity and pharmacokinetics of liposomes containing water-soluble prodrugs of paclitaxel," Journal of Controlled Release, vol. 63, pp. 141-153, (2000).

Champagne et al., "Nanometer-scale scanning sensors fabricated using stencil lithography," Applied Physics Letters, vol. 82, No. 7, pp. 1111-1113, Feb. 17, 2003.
Chandra et al., "Biodegradable Polymers," Progress in Polymer Science, vol. 23, pp. 1273-1335, (1998).
Chang et al., "Preparation and Characterization of Nanostructured Tin Oxide Films by Electrochemical Deposition," Electrochemical and Solid-State Letters, vol. 5, No. 8, pp. C71-C74, (2002).
Chen et al., "Blood compatiblity and $sp^3/sp^2$ contents of diamond-like carbon (DLC) synthesized by plasma immersion ion implantation-deposition," Surface and Coatings Technology, vol. 156, pp. 289-294, (2002).
Chen et al., "Fabrication of micro-field emitters on ceramic substrates," Microelectronic Engineering, vol. 84, pp. 94-100, (2007).
Chen et al., "Behavior of Cultured Human Umbilical Vein Endothelial Cells on Titanium Oxie Films Fabricated by Plasma Immersion Ion Implantation and Deposition," Surface & Coatings Technology, vol. 186, pp. 270-276, (2004).
Cheng et al., "Anatase Coating on NiTi Via a Low-Temperature Sol-Gel Route for Improving Corrosion Resistance," Scripta Materialia, vol. 51, pp. 1041-1045, (2004).
Cho et al., "A Novel Route to Three-Dimensionally Ordered Macroporous Polymers by Electron Irradiation of Polymer Colloids" Advanced Materials, vol. 17, No. 1, pp. 120-125, Jan. 6, 2005.
Cho et al., "Influence of Silica on Shape Memory Effect and Mechanical Properties of Polyurethane-Silica Hybrid," European Polymer Journal, vol. 40, pp. 1343-1348, (2004).
Cho et al., "Preparation and Characterization of Iridium Oxide Thin Films Grown by DC Reactive Sputtering," Japanese Journal of Applied Physics, vol. 36, Part 1, No. 3B, pp. 1722-1727, Mar. 1997.
Choi et al., "Synthesis and Characterization of Diamond-Like Carbon Protective AR Coating," Journal of the Korean Physical Society, vol. 45, p. S864, Dec. 2004.
Chougnet et al., "Substrates do influence the ordering of mesoporous thin films," Journal of Materials Chemistry, vol. 15, pp. 3340-3345, (2005).
Chougnet et al., "The Influence of the Nature of the Substrate on the Ordering of Mesoporous Thin Films," Thin Solid Films, vol. 495, pp. 40-44, (2006).
Chow et al., "Nanostructured Films and Coating by Evaporation, Sputtering, Thermal Spraying, Electro and Electroless Deposition," Handbook of Nanophase and Nanostructured Materials, vol. 1, Chapter 9, pp. 246-272, (2003).
Chow et al., "Preliminary Evaluation of KEM for Fabrication," Proceedings of the 12th General Meeting of JOWOG 31, Livermore, CA, University of California, (1996).
Chronakis, "Novel nanocomposites and nanoceramics based on polymer nanofibers using electrospinning process—A review," Journal of Materials Processing Technology, vol. 167, pp. 283-293, (2005).
Chu, "Recent developments and applications of plasma immersion ion implantation," Journal of Vacuum Science Technology, vol. B22, No. 1, pp. 289-296, Jan./Feb. 2004.
Chuang et al., "Titanium Oxide and Polyaniline Core-Shell Nanocomposites," Synthetic Metals, vol. 152, pp. 361-364, (2005).
Chung et al., "Roles of discontinuities in bio-inspired adhesive pads," Journal of the Rolyal Society: Interface, vol. 2, pp. 55-61, Feb. 8, 2005.
Clark, "Micropatterning Cell Adhesiveness", Immobilized Biomolecules in Analysis, Oxford University Press, pp. 95-111, (1998).
Clevy et al., "Micromanipulation and Micro-Assembly Systems," IEEE/RAS International Advanced Robotics Program, IARP'06, Paris, France, (2006).
Colina et al., "DNA deposition through laser induced forward transfer," Biosensors and Bioelectronics, vol. 20, pp. 1638-1642, (2005).
Costanzo et al., "Model-Based Simulations to Engineer Nanoporous Thin Films," LPCM Research, Pennsylvania State University, (2004), (http://lpcm.esm.psu.edui/~tjy107/research.htm).
Course: C-103, "An Introduction to Physical Vapor Deposition (PVD) Processes," Society of Vacuum Coaters, SVC Education Programs: course description and syllabus, Apr. 19, 2008.
Course: C-208, "Sputter Deposition in Manufacturing" Society of Vacuum Coaters, SVC Education Programs: course description and syllabus, Apr. 22, 2008.
Csete et al., "The existence of sub-micrometer micromechanical modulation generated by polarized UV laser illumination on polymer surfaces," Materials Science and Engineering C, vol. 23, pp. 939-944, (2003).
Csete et al., "The role of original surface roughness in laser-induced periodic surface structure formation process on poly-carbonate films," Thin Solid Films, vol. 453-454, pp. 114-120, (2004).
Curtis et al. "Cells react to nanoscale order and symmetry in their surroundings," IEEE Transactions On Nanobioscience, vol. 3, No. 1, pp. 61-65, Mar. 2004.
Curtis et al., "Nantotechniques and approaches in biotechnology," Trends in Biotechnology, vol. 19, No. 3, pp. 97-101, Mar. 2001.
Curtis et al., "New Depths in Cell Behaviour: Reactions of Cells to Nanotopography," Biochem, Soc, Symp, vol. 65, pp. 15-26, (1999).
Curtis et al., "New depths in cell behaviour: Reactions of cells to nanotopography," Biochemical Society Symposium, No. 65, pp. 15-26 (1997).
Curtis et al., "Topographical Controls of Cells," Biomaterials, vol. 18, pp. 1573-1583, (1997).
Curtis, "Tutorial on the biology of nanotopography," IEEE Transactions on Nanobioscience, vol. 3, No. 4, pp. 293-295, Dec. 2004.
Cyster et al., "The effect of surface chemistry and nanotopography of titanium nitride (TiN) films on 3T3-L1 fibroblasts," Journal of Biomedical Materials Research: A., vol. 67, No. 1, pp. 138-147, Oct. 2003.
Cyster et al., "The effect of surface chemistry and nanotopography of titanium nitride (TiN) films on primary hippocampal neurones," Biomaterials, vol. 25, pp. 97-107, (2004).
da Cruz et al., "Preparation, structure and electrochemistry of a polypyrrole hybrid film with $[Pd(dmit)_2]^{2-}$ bis(1,3-dithiole-2-thione-4,5-dithiolate)palladate(II)," Electrochimica Acta, vol. 52, pp. 1899-1909, (2007).
Dalby et al., "In vitro reaction of endothelial cells to polymer demixed nanotopography," Biomaterials, vol. 23, No. 14, pp. 2945-2954, (2002).
Dalby, "Topographically induced direct cell mechanotransduction," Medical Engineering & Physics, vol. 27, No. 9, pp. 730-742, (2005).
Damen et al., "Paclitaxel Esters of Malic Acid as Prodrugs with Improved Water Solubility," Bioorganic & Medicinal Chemistry, vol. 8, pp. 427-432, (2000).
D'Aquino, "Good Drug Therapy: It's Not Just the Molecule—It's the Delivery," CEP Magazine, (www.cepmagazine.org), 3 pages, Feb. 2004.
Datta et al., "Fundamental aspects and applicatio of electrochemical microfabrication," Electrochimica Acta, vol. 45, pp. 2535-2558, (2000).
Daxini et al., "Micropatterned polymer surface inprove retention of endothelial cells exposed to flow-induced shear stress," Biorheology, vol. 43, pp. 45-55, (2006).
De Aza et al., "Crack growth resistance of alumina, zirconia and zirconia toughened alumina ceramics for joint prostheses," Biomaterials, vol. 23, No. 3, pp. 937-945, Feb. 2002.
Deakin et al., "De-alloying of type 316 stainless steel in hot, concentrated sodium hydroxide solution," Corrosion Science, vol. 46, pp. 2117-2133, (2004).
Debiotech, "Debiostar, An Innovative Solution for Sustained Drug Delivery," Copyright 2001, (http://www.debiotech.com/products/drugdd/stent_page_1.html).
Debiotech, "Debiostent: An Innovatice Ceramic Coating for Implantable Medical Devices," [first downloaded on Sep. 1, 2005], (http://www.debiotech.com/products/drugdd/stent_page_1.html).
Debiotech, "Debiostent: Polymer free drug eluting coating," Jun. 14, 2007, (www.debiotech.com/products/druggd/stent_page_1.html).
Debiotech, "Debiotech Obtains Exclusive Rights to an Innovative Drug Eluting Stent Technology," Press release, 1 page, Mar. 7, 2003.
Demisse, "Computational Investigation of Conducting Polythiophenes and Substituted Polythiophenes," A Thesis Submitted to the School of Graduate Studies of Addis Ababa University, Ethiopia, Jun. 2007.

Deniau et al., "Study of the polymers obtained by electroreduction of methacrylonitrile," Journal of Electroanalytical Chemistry, vol. 505, pp. 33-43, (2001).

Desai et al., "Characterization of micromachined silicon membranes for immunoisolation and bioseparation applications," Journal of Membrane Science, vol. 159, pp. 221-231, (1999).

Desai et al., "Use of Microfabricated 'Nanopore' Membranes as a Rate-Limiting Barrier to Diffusion of Small and Large Molecules: Possible Role in Drug Delivery" BioMEMs and Nanotechnology World, (2001).

Desai, Integrating Cells with Microsystems: Application in Tissue Engineering and Cell-Based Delivery, PowerPoint presentation, May 10, 2002.

Di Mario et al., "Drug-eluting bioabsorbable magnesium stent," Journal of Interventional Cardiology, vol. 17, Issue 6, Dec. 2004.

Di Mario et al., "Moonlight: a controlled registry of an iridium oxide-coated stent with angographic follow-up," International Journal of Cardiology, vol. 95, pp. 329-331, (2004).

Di Mario, The Moonlight Study: Multicenter Objective Observational Lunar Iridium Oxide Intimal Growth Trial, PowerPoint presentation in 2002.

Dibra et al., "Influence of the stent surface topology on the outcomes of patients undergoing coronary stenting: a randomized double-blind controlled trial", Catheterization and Cardiovascular Interventions, vol. 65, pp. 374-380, (2005).

Dittmar et al., "Nanostructured Smart Drug Delivery Coatings," European Cells and Materials, vol. 31, Supplement 2, p. 73, (2007).

Dong et al., "Preparation of Submicron Polypyrrole/Poly(methly methacrylate) Coaxial Fibers and conversion to Polypyrrole Tubes and Carbon Tubes," Langmuir, vol. 22, pp. 11384-11387, (2006).

Doraiswamy et al., "Excimer laser forward transfer of mammalian cells using a novel triazene absorbing layer," Applied Surface Science, vol. 252, pp. 4743-4747, (2006).

DTI Technology Group: Materials-Coating, "Kinetic spray coating method," www.delphi.com, Jul. 2004.

Dumas et al., "Characterization of magnesium fluride thin films produced by argon ion beam-assisted deposition," Thin Solid Films, vol. 382, pp. 61-68, (2001).

Duncan et al., "Polymer-drug conjugates, PDEPT and PELT: basic principals for design and transfer from laboratory to clinic," Journal of Controlled Release, vol. 74, pp. 135-146, (2001).

Duncan, "The Dawning Era of Polymer Therapeutics," Nature Reviews: Drug Discovery, vol. 2, pp. 347-360, May 2003.

Dutta et al., "Self-Organization of Colloidal Nanoparticles," Encyclopedia of Nanoscience and Nanotechnology, vol. 9, pp. 617-640, (2003).

Duwez et al., "Mechanochemistry: targeted delivery of single molecules," Nature Nanotechnology, vol. 1, pp. 122-125, (2006).

EAG Technical Note, "Functional Sites on Non-polymeric Materials: Gas Plasma Treatment and Surface Analysis," Evans Analytical Group, (2003).

Eberli et al., "The Lunar Coronary Stent System," Handbook of coronary stents, 4th edition, Chapter 17 (Martin Dunitz Ltd 2002).

Eesley et al., "Thermal properties of kinetics spray A1-SiC metal-matrix composite," Journal of Materials Research, vol. 18, No. 4, pp. 855-860, Apr. 2003.

Egerhazi et al., "Thickness distribution of carbon nitride films grown by inverse-pulsed laster deposition," Applied Surface Science, vol. 247, pp. 182-187, (2005).

Electropolymerization, (http://intel.ucc.ie/sensors/Electropolym.htm) (downloaded [2007]).

Erlebacher et al., "Evolution of nonoporosity in dealloying," Nature, vol. 410, pp. 450-453, Mar. 22, 2001.

Esrom et al., "New approach of a laser-induced forward transfer for deposition of patterned thin metal films," Applied Surface Science, vol. 86, pp. 202-207, (1995).

Faupel et al., "Microstructure of pulsed laser deposited ceramic-metal and polymer-metal nanocomposite thin films," Applied Physics A, vol. 79, pp. 1233-1235 (2004).

Faust et al., "Biofunctionalised Biocompatible Titania Coatings for Implants," Euro Ceramics VII, Key Engineering Materials, vol. 206, No. 2, pp. 1547-1550, (2006).

Fernandez-Pradas et al., "Laser-induced forward transfer of biomolecules," Thin Solid Films, vol. 453-454, pp. 27-30, (2004).

Ferraz et al., "Influence of nanoporesize on platelet adhesion and activation," Journal of Materials Science: Materials in Medicine, vol. 19, pp. 3115-3121, (2008).

Figallo et al., "Micropatterned Biopolymer 3D Scaffold for Static and Dynamic Culture of Human Fibroblasts," Biotechnology Progress, vol. 23, pp. 210-216, (2007).

Flemming et al., "Effects of synthetic micro- and nano-structured surfaces on cell behavior," Biomaterials, vol. 20, No. 6, pp. 573-588, (1999).

Fogarassy et al., "Laser-induced forward transfer: A new approach for the deposition of high $T_c$ superconducting thin films," Journal of Materials Research, vol. 4, No. 5, pp. 1082-1086, Sep./Oct. 1989.

Fonseca et al., "Paclitaxel-loaded PLGA nanoparticles: preparation, physicochemical characterization and in vitro anti-tumoral activity," Journal of Controlled Release, vol. 83 pp. 273-286, (2002).

Forty, "Corrosion micromorphology of noble metal alloys and depletion gilding," Nature, vol. 282, pp. 597-598, Dec. 6, 1979.

Frechet, "Functional Polymers: from Plastic Electronics to Polymer-Assisted Therapeutics," Progress in Polymer Science, vol. 30, pp. 844-857, (2005).

Free Online Dictionary, "Aperture," definition, [first viewed Oct. 9, 2009].

Freitas et al., "Nimesulide PLA microsphere as a potential sustained release system for the treatment of inflammatory diseases," International Journal of Pharmaceutics, Vo. 295, pp. 201-211, (2005).

Freitas, "Nanomedicine, vol. I: Basic Capabilities," Landes Bioscience, pp. 87, 90, 255 and 265, (1999).

Friedrich et al., "Developing Interdisciplinary Undergraduate and Graduate Courses Through the Integration of Recent Research Results into the Curricula," (http://www.ineer.org/Events/ICEE1997/Proceedings/paper326.htm), 10 pages, [first downloaded Mar. 10, 2005.].

Fu et al., "Effects of mesh-assisted carbon plasma immersion ion implantation on the surface propoerties of insulating silicon carbide ceramics," Journal of Vacuum Science Technology, vol. A22, No. 2, pp. 356-360, Mar./Apr. 2004.

Fu et al., "Influence of thickness and dielectric properties on implantation efficacy in plasma immersion ion implantation of insulators," Journal of Applied Physics, vol. 95, No. 7, pp. 3319-3323, Apr. 1, 2004.

Fujisawa et al., "A novel textured surface for blood-contact," Biomaterials, vol. 20, pp. 955-962, (1999).

Fulton, "Ion-Assisted Filtered Cathodic Arc Deposition (IFCAD) System for Volume Production of Thin-Film Coatings," Society of Vacuum Coaters, 42nd Annual Technical Conference Proceedings, (1999).

Gabel et al., "Solid-State Spray Forming of Aluminum Near-Net Shapes," Journal of Metals, vol. 49, No. 8, pp. 31-33, (1997).

Gabel, "Low Temperature Metal Coating Method," Lawrence Livermore National Laboratory, Apr. 3, 2000.

Gadegaard et al., "Tubes with Controllable Internal Nanotopography," Advanced Materials, vol. 16, No. 20, pp. 1857-1860, Oct. 18, 2004.

Galinski et al., "Ionic liquids as electrolytes," Electrochimica Acta, vol. 51, 5567-5580, (2006).

Gao, "Chemical Vapor Deposition," Handbook of Nanophase and Nanostructured Materials, vol. 1: Synthesis, Chapter 5, (2003).

Geretovszky et al., "Correlation of compositional and structural changes during pulsed laser deposition of tantalum oxide films," Thin Solid Films, vol. 453-454, pp. 245-250, (2004).

Gillanders et al., "A Composite Sol-Gel/Fluoropolymer Matrix for Dissolved Oxygen Optical Sensing," Journal of Photochemistry and Photobiology A: Chemistry, vol. 163, pp. 193-199, (2004).

Glocker et al., "AC Reactive Sputtering with Inverted Cylindrical Magnetrons," Society of Vacuum Coaters, 43rd Annual Technical Conference Proceedings—Denver, pp. 81-85, Apr. 15-20, 2000.

Glocker et al., "Recent developments in inverted cylindrical magnetron sputtering," PowerPoint presentation, (2001).

Glocker et al., "Recent developments in inverted cylindrical magnetron sputtering," Surface and Coatings Technology, vol. 146-147, pp. 457-462, (2001).

Goddard et al., "Polymer surface modification for the attachmend of bioactive compounds," Progress in Polymer Science, vol. 32, pp. 698-725, (2007).

Goh et al., "Nanostructuring Titania by Embossing with Polymer Molds Made from Anodic Alumina Templates," Nano Letters, vol. 5, No. 8, pp. 1545-1559, (2005).

Gollwitzer et al., "Titania Coating as Local "Drug" Delivery System with Antibacterial and Biocompatible Properties," (2003).

Gong et al., "Controlled molecular release using nanopourous alumina capsules," Biomedical Microdevices, vol. 5, No. 1, pp. 75-80, Mar. 2003.

Gong et al., "Titanium oxide nanotube arrays prepared by anodic oxidation," Journal of Material Research, vol. 16, No. 12, pp. 3331-3334, (2001).

Goodison et al., "CD44 cell adhesion molecules," Journal of Clinical Pathology: Molecular Pathology, vol. 52, pp. 189-196, (1999).

Goodman et al., "Three-dimensional extracellular matrix textured biomaterials," Biomaterials, vol. 17, pp. 2087-295, (1996).

Gorb et al., "Biological microtribology: anisotropy in frictional forces of orthopteran attachment pads reflects the unltrastructure of a highly deformable material," Proceeding of the Royal Society, London series B, vol. 267, pp. 1239-1244, (2000).

Gotszalk et al., "Diagnostics of micro- and nanostructure using the scanning probe microscopy," Journal of Telecommunications and Information Technology, pp. 41-46, (2005).

Granqvist et al., "Biodegradable and bioactive hybrid organic-inorganic PEG-siloxane fibers: Preparation and Characterization," Colloid Polymer Science, vol. 282, pp. 495-501, (2004).

Greeley et al., "Electrochemical dissolution of surface alloys in acids: Thermodynamic trends from first-principles calculations," Electrochimica Acta, vol. 52, pp. 5829-5836, (2007).

Green et al., "XPS Characterisation of Surface Modified Ni-Ti Shape Memory Alloy," Materials Science and Engineering, vol. A224, pp. 21-26, (1997).

Gressel-Michel et al., "From a Microwave Flash-Synthesized $TiO_2$ Colloidal Suspension to $TiO_2$ Thin Films," Journal of Colloid and Interface Science, vol. 285, pp. 674-679, (2005).

Groth et al., "Layer-by-Layer Deposition of Polyelectrolytes—A Versatile Tool for the In Vivo Repair of Blood Vessels," Angewandte Chemie, International Edition, vol. 43, pp. 926-928, (2004).

Grubmuller, "What happens if the Room at the Bottom Runs Out? A Close Look at Small Water Pores," PNAS, vol. 100, No. 13, pp. 7421-7422, Jun. 24, 2003.

Gu et al., "Biomimetic titanium dioxide film with structural color and extremely stable hydrophilicity," Applied Physics Letters, vol. 85, No. 21, pp. 5067-5069 (2004).

Guangliang et al., "The effects of current density on the phase composition and microstructure properties of micro-arc oxidation coating," Journal of Alloys and Compounds, vol. 345, pp. 169-200, (2002).

Guo et al., "Formation of oxygen bubbles and its influence on current efficiency in micro-arc oxidation process of AZ91D magnesium alloy," Thin Solid Films, vol. 485, pp. 53-58, (2005).

Guo et al., "Growth of ceramic coatings on AZ91D magnesium alloys by micro-arc oxidation in aluminate-fluoride solutions and evaluacation of corrosion resistance," Applied Surface Science, col. 246, pp. 229-238, (2005).

Guo et al., "Investigation of corrosion behaviors of Mg-6Gd-3Y-0.4Zr alloy in NaCl aqueous solutions," Electrochimica Acta, vol. 52, pp. 2570-2579, (2007).

Guo et al., "Sol gel derived photocatalytic porous $TiO_2$ thin films," Surface & Coatings Technology, vol. 198, pp. 24-29, (2005).

GVD Corporation, "Nanocoatings for a New Era," [first downloaded Nov. 12, 2003].

Haag et al., "Polymer Therapeutics: Concepts and Applications," Angewandte Chemie, vol. 45, pp. 1198-1215, (2006).

Haberland et al., "Filling of micron-sized contact holes with copper by energetic cluster impact," Journal of Vacuum Science Technology A, vol. 12, No. 5, pp. 2925-2930, Sep./Oct. 1994.

Haery et al., "Drug-eluting stents: The beginning of the end of restenosis?," Cleveland Clinic Journal of Medicine, vol. 71, No. 10, pp. 815-824, (2004).

Hahn et al., "A novel approach for the formation of Mg(OH)2/MgO nanowhiskers on magnesium: Rapid anodization in chloride containing solutions", Electrochemistry Communications, vol. 10, pp. 288-292, (2008).

Halme et al., "Spray Deposition and Compression of $TiO_2$ Nanoparticle Films for Dye-Sensitized Solar Cells on Plastic Substrates," Solar Energy Materials & Solar Cells, vol. 90, pp. 887-899, (2006).

Hamley et al., "Nanostructure fabrication using block copolymers," Nanotechnology, vol. 14, pp. R39-R54, (2003).

Han et al., "Electron injection enhancement by diamond-like carbon film in organic electroluminescence devices," Thin Solid Films, vol. 420-421, pp. 190-194, (2002).

Han et al., "Pourous nanocrystalline titania films by plasma electrolytic oxidation," Surface and Coatings Technology, vol. 154, pp. 314-318, (2002).

Han et al., "Structure and in vitro bioactivity of titania-based films by micro-arc oxidation," Surface and Coatings Technology, vol. 168, pp. 249-258, (2003).

Han et al., "Synthesis of nanocrystalline titaniaa films by micro-arc oxidation," Materials Letters, vol. 56, pp. 744-747, (2002).

Hanley et al., "The growth and modification of materials via ion-surface processing," Surface Science, vol. 500, pp. 500-522, (2002).

Harris et al., "Fabrication of Perforated Thin Films with Helical and Chevron Pore Shapes," Electrochemical and Solid-State Letters, vol. 4, pp. C39-C42, (2004).

Harvard Nanopore, "Ion Beam Sculpting: Material Science—Fabricating Nanopores and Other Nanoscale Feature," [first downloaded Jul. 2, 2003], (http://www.mcb.harvard.edu.branton/projects-IonBeam/htm).

Hattori et al., "Photoreactivity of Sol-Gel $TiO_2$ Films Formed on Soda-Lime Glass Substrates: Effects of $SiO_2$ Underlayer Containing Fluorine," Langmuir, vol. 15, pp. 5422-5425, (1999).

Hau et al., "Surface-chemistry technology for microfluidics," Journal of Micromechanics and Microengineering, vol. 13, pp. 272-278, (2003).

Hausleiter et al., "Prvention of restenosis by a novel drug-eluting stent system with a dose-adjustable, polymer-free, on-site stent coating," European Heart Journal, vol. 26, pp. 1475-1481, (2005).

He et al., "Electrochemical Fabrication of Metal Nanowires," Encyclopedia of Nanoscience and Nanotechnology, vol. X, pp. 1-18, (2003).

He et al., "Optical properties of diamond-like carbon synthesized by plasma immersion ion processing," Journal of Vacuum Science Technology, vol. B17, No. 2, pp. 822-827, Mar./Apr. 1999.

Heidenau et al., "Structured Porous Titania as a Coating for Implant Materials," Key Eng Mater. vol. 192-195, pp. 87-90, (2001).

Heinig et al., "Modeling and Simulation of Ion Beam Systhesis of Nanoclusters," 6 pages, [first downloaded Jan. 3, 2000], (http://www.fz-rossendorf.de/pls/rois/Cms?pOId=10960&pFunc=Print&pLang=de).

Helmersson et al., "Ionized physical vapor deposition (IPVD): A review of technology and applications," Thin Solid Films, vol. 513, pp. 1-24, (2006).

Helmus et al. "Surface Analysis of a Series of Copolymers of $_L$-Glutamic Acid and $_L$-Leucine," Journal of Colloid and Interface Science, vol. 89, No. 2, pp. 567-570, (1982).

Helmus et al., "Plasma Interaction on Block Copolymers as Determined by Platelet Adhesion," Biomaterials: Interfacial Phenomena and Applications: Chapter 7, pp. 80-93, (1981).

Helmus et al., "The Effect of Surface Charge on Arterial Thrombosis," Journal of Biomedical Materials Research, vol. 18, pp. 165-183, (1984).

Hentze et al., "Porous polymers and resins for biotechnological and biomedical applications," Reviews in Molecular Biology, vol. 90, pp. 27-53, (2002).

Hoa et al., "Preparation of porous meterials with ordered hole structure," Advances in Colloid and Interface Science, vol. 121, pp. 9-23, (2006).

Hoffman, "Non-Fouling Surface Technologies," Journal of Biomaterials Science, Polymer Edition, vol. 10, No. 10, pp. 1011-1014, (1999).

Hoglund, "Controllable Degradation Product Migration From Biomedical Polyester-ethers," KTH Chemical Science and Engineering, Stockholm, May 24, 2007.

Holland et al., "Synthesis of Macroporous Minerals with Highly Ordered Three-Dimensional Arrays of Spheroidal Voids," Science, vol. 281, pp. 538-540, Jul. 24, 1998.

Hong et al., "The super-hydrophilicities of Bi-TiO2, V-TiO2, and Bi-V-TiO2 nano-sized particles and their benzene photodecompositions with H2O addition," Materials Letters, vol. 60, pp. 1296-1305, (2006).

Hopp et al., "Absorbing film assisted laser induced forward transfer of fungi (*Trichoderma conidia*)," Journal of Applied Physics, vol. 96, No. 6, pp. 3478-3481, Sep. 15, 2004.

Houbertz, "Laser interaction in sol-gel based materials—3-D lithography for photonic applications," Applied Surface Science, vol. 247, pp. 504-512, (2005).

Houdayer et al., "Preparation of new antimony(0)/polyaniline nanocomposites by a one-pot solution phase method," Materials Letter, vol. 61, pp. 171-176, (2007).

Hrudey et al., "Organic $Alq_3$ Nanostructures Fabricated with Glancing Angle Depostion," Vacuum Technology & Coating, May 2006.

Hsiao et al., "Soluble aromatic polyamides bearing asymmetrical diaryl ether groups," Polymer, vol. 45, pp. 7877-7885, (2004).

Hu et al., "Cyclic voltammetric deposition of hydrous ruthenium oxide for electrochemical capacitors: effects of codeposting iridium oxide," Electrochimica Acta, vol. 45, pp. 2684-2696, (2000).

Hu et al., "Voltammetric investigation of platinum oxides II. Efect of hydration on the reduction behavior," Electrochimica Acta, vol. 45, pp. 3063-3068, (2000).

Hüppauff et al., "Valency and Structure of Iridium in Anodic Iridium Oxide Films," Journal of Electrochemical Society, vol. 140, No. 3, pp. 598-602, Mar. 1993.

Hurley et al., "Nanopatterning of Alkynes on Hydrogen-Terminated Silicon Surfaces by Scanning Probe-Induced Cathodic Eletrografting," Journal of American Chemistry Society, vol. 125, pp. 11334-11339, (2003).

Hussain et al., "Atomic force microscope study of three-dimensional nanostructure sidewalls," Nanotechnology, vol. 18, pp. 1-8, (2007).

Ichinose et al., "A surface sol-gel process of $TiO_2$ and other metal oxide films with molecular precision," Chem. Mater. vol. 9, pp. 1296-1298, (1997).

Ichinose et al., "Ultrathin composite films: An indispensable resource for nanotechnolo ," Riken Review, No. 37, pp. 34-37, Jul. 2001.

Ignatova et al., "Combination of Electrografting and Aton-Transfer Radical Polymerization for Making the Stainless Steel Surface Antibacterial and Protein Antiadhesive," Langmuir, vol. 22, pp. 255-262, (2006).

Imai et al., "Preparation of Porous Anatase Coatings from Sol-Gel-Derived Titanium Dioxide and Titanium Dioxide-Silica by Water-Vapor Exposure," Journal of American Ceramics Society, vol. 82, No. 9, pp. 2301-2304, (1999).

Inflow Dynamics starts "LUSTY" Study, Company Press Release: First clinical trial with Niobium stents, (www.tctmd.com/industry-news/one.html?news_id=3364), Jun. 25, 2002.

Inoue et al., "Corrosion rate of magnesium and its alloys in buffered chloride solutions," Corrosion Science, vol. 44, pp. 603-610, (2002).

Inovati, "Award Winning—Environmentally-Safe, High-Quality, Metal Spray Process," Press Release, (2002), (http://www.inovati.com/papers/KM-PressRelease.doc).

Inovati, "Inovati to Develop Green Metal Coating Technology" Press Release, [first downloaded Sep. 1, 2005], (http://www.inovati.com/papers/bmdopr.html).

Inovati, "Low temperature, high-speed sprays make novel coatings," [first downloaded on Mar. 18, 2003], (http://www.inovati.com/papers/ampmar01.html).

Introduction to the Metal Printing Process: Future manufacturing equipment of advanced materials and complex geometrical shapes, (www.mpp.no/intro/intro.htm), downloaded Mar. 18, 2002.

Irhayem et al., "Glucose Detection Based on Electrochemically Formed Ir Oxide Films," Journal of Electroanalytical Chemisty, vol. 538-539, pp. 153-164, (2002).

Irvine et al., Nanoscale clustering of RGD peptides at surfaces using Comb polymers. 1. Synthesis and characterization of Comb thin films, Biomacromolecules, vol. 2, No. 1, pp. 85-94, Spring 2001.

Irvine et al., "Nanoscale clustering of RGD peptides at surfaces using comb polymers. 2. Surface segregation of comb polymers in polylactide," Biomacromolecules, vol. 2, No. 2, pp. 545-556, Summer 2001.

Ishizawa et al., "Characterization of thin hydroxyapatite layers formed on anodic titanium oxide films containing Ca and P by hydrothermal treatment," Journal of Biomedical Materials Research, vol. 29, pp. 1071-1079, (1995).

Ishizawa et al., "Histomorphometric evalucation of the thin hydroxyapatite layer formed through anodization followed by hydrothermal treatment," Journal of Biomedical Materials Research, vol. 35, pp. 199-206, (1997).

Isoflux Inc., "Isoflux specializes in vacuum coating equipment and coating process," http://www.isofluxinc.com/about.shtml, Jul. 2009.

Iurhayem et al. "Glucose detection based on electrochemically formed Ir oxide films," Journal of Electroanalytical Chemistry, vol. 539-539, pp. 153-164, (2002).

Jensen et al., "Low-temperature preparation of nanocrystalline anatase films through a sol-gel rout," Journal of Sol-Gel Science and Technology, vol. 39, pp. 229-233, (2006).

Jewell et al., "Multilayered polyelectolyte films promote the direct and localized delivery of DNA to cells," Journal of Controlled Release, vol. 106, pp. 214-223, (2005).

JMAR LLC, "Collimated Plasma Lithography (CPL)," [first downloaded Jul. 2, 2003], (http://www.jmar.com/co451.html).

Johnson, "What's an Ionic Liquid?," The Electrochemical Society: Interface, pp. 38-41, Spring 2007.

Juodkazis et al., "Alternative view of anodic surface oxidation of nobel metals," Electrochimica Acta, vol. 51, pp. 6159-6164, (2006).

Kamei et al., "Hydrophobic drawings on hydrophilic surfaces of single crystalline titanium dioxide: surface wettability control by mechanochemical treatment," Surface Science Letters, vol. 463 pp. L609-L612, (2000).

Kanda et al., "Characterization of Hard Diamond-Like Carbon Films Formed by Ar Gas Cluster Ion Beam-Assisted Fullerene Deposition," Japanese Journal of Applied Physics, vol. 41, Part 1, No. 6B, pp. 4295-4298, Jun. 2002.

Kang et al., "Controlled drug release using nanoporous anodic aluminum oxide on stent," Thin Solid Films, vol. 515, pp. 5184-5187, (2007).

Kaplan, "Cold Gass Plasma and Silanes," Presented at the 4th International Symposium on Silanes and Other Coupling Agents, Jul. 11-13, 2003.

Karuppuchamy et al., "Cathodic Electrodeposition of Oxide Semiconductor Thin Films and their Application to Dye-Sensitized Solar Cells," Solid State Ionics, vol. 151, pp. 19-27, (2002).

Karuppuchamy et al., "Photoinduced Hydrophilicity of Titanium Dioxide Thin Films Prepared by Cathodic Electrode position," Vacuum, vol. 80, pp. 494-498, (2006).

Karuppuchamy et al., "Super-hydrophilic amorphous titanium dioxide thin film deposited by cathodic electrodeposition," Materials Chemisty and Physics, vol. 93, pp. 251-254, (2005).

Karuri et al., "Biological length scale topography enhances cell-substratum adhesion of human corneal epithelial cells," Journal of Cell Science, vol. 117, No. 15, pp. 3153-3164, (2004).

Kasemo et al., "Implant surfaces and interface processes," Adv. Dent. Res. vol. 13, pp. 8-20 Jun. 1999.

Kasemo, "Biological surface science," Surface Science, vol. 500, pp. 656-677, (2002).

Kato et al., "N-succinyl-chitosan as a drug carrier: water-insoluble and water-soluble conjugates," Biomaterials, vol. 25, pp. 907-915, (2004).

Katsumata et at., "Effect of Microstructure on Photoinduced Hydrophilicity of Transparent Anatase Thin Films," Surface Science, vol. 579, pp. 123-130, (2005).

Katz, "Developments in Medical Polymers for Biomaterials Applications," Medical Device Link, Jan. 2001, (http://www.devicelink.com/mddi/archive/01/01/003.html).

Kean et al. "The Analysis of Coatings Produced by Accelerated Nanoparticles," Mantis Deposition Ltd., Presentaction at NSTI Nano Tech 2006, Boston, May 7th-11th 2006.

Kesapragada et al., "Two-component nanopillar arrays grown by Glancing Angle Deposition," Thin Solid Films, vol. 494, pp. 234-239, (2006).

Kesler etal., "Enhanced Strength of Endothelial Attachment on Polyester Elastomer and Polytetrafluoroethylene graft Surfaces with Fibronectin Substrate," Journal of Vascular Surgery, vol. 3, No. 1, pp. 58-64, (1986).

Kesting, "Synthetic Polymeric Membranes—A Structural Perspective", Chapters 6-7, pp. 225-286, Oct. 1985.

Kickelbick, "Concepts for the incorporation of inorganic building blocks into organic polymers on a nanoscale," Progress in Polymer Science, vol. 28, pp. 81-114, (2003).

Kidambi et al., "Selective Depositions on Polyelectrolyte Multilayers: Self-Assembled Monolayers on m-dPEG Acid as Molecular Template," Journal of the American Chemistry Society, vol. 82, No. 9, pp. 4697-4703, (2004).

Kilian et al., "Plasma transglutaminase factor XIII induces microvessel ingrowth into biodegradable hydroxyapatite implants in rats," Biomaterials, vol. 26, pp. 1819-1827, (2005).

Kim et al. "Porous ZrO2 bone scaffold coated with hydroxyapatite with fluorapatite intermediate layer," Biomaterials, vol. 24, pp. 3277-3284, (2003).

Kim et al., "Adhesion of RF bias-sputtered Cr thin films onto photosensitivepolyimide substrates," IEEE, International Symposium on Eelectrical Materials and Pakaging, pp. 202-207, (2001).

Kim et al., "Fabrication of WC-Co coatings by cold spray deposition," Surface & Coatings Technology, vol. 191, pp. 335-340, (2005).

Kim et al., "Hollow Silica Spheres of Controlled Size and Porosity by Sol-Gel Processing," Journal of Americal Ceramic Society, vol. 74, Nol. 8, pp. 1987-1992, (1991).

Kim et al., "Proton conducting polydimethylsiloxane/metal oxide hybrid membranes added with phosphotungstic acid(II)," Electrochimica Acta, vol. 49, pp. 3429-3433, (2004).

Kim et al., "Fabrication and Characterization of $TiO_2$ Thin Film Prepared by a Layer-By-Layer Self-Assembly Method," Thin Solid Films, vol. 499, pp. 83-89, (2006).

Kitagawa et al., "Near-Edge X-Ray Absorption Fine Structure Study for Optimization of Hard Diamond-Like Carbon Film Formation with Ar Cluster Ion Beam," Japanese Journal of Applied Physics, vol. 42, pp. 3971-3975, (2003).

Kitagawa et al., Optimum Incident Angle of Ar Cluster Ion Beam for Superhard Carbon Film Deposition, Japanese Journal of Applied Physics, vol. 43, No. 6B, pp. 3955-3958, (2004).

Kittaka et al., "The Structure of Water Monolayers on a Hydroxylated Chromium Oxide Surface," Adsorption, vol. 11, pp. 103-107, (2005).

Kleinertz et al., "LUSTY Studie: Lunar STF Study," PowerPoint presentation on Sep. 4, 2004.

Kleisner et al., "A system based on metal alkyl species that forms chemically bound organic overlays n hydroxylated planar surfaces," Thin Solid Films, vol. 381, pp. 10-14, (2001).

Kogure et al., "Microstructure of nemalite, fibrous iron-bearing brucite", Mineralogical Journal, vol. 20, No. 3, pp. 127-133, Jul. 1998.

Kohli et al., "Arrays of lipid bilayers and liposomes on patterned polyelectrolyte templates," Journal of Colloid and Interface Science, vol. 301, pp. 461-469, (2006).

Kokubo et al., "Novel bioactive materials with different mechanical properties," Biomaterials, vol. 24, pp. 2161-2175, (2003).

Kommireddy et al., "Layer-by-Layer Assembly of $TiO_2$ Nanoparticles for Stable Hydrophilic Biocompatible Coatings" Journal of Nanoscience and Nanotechnology, vol. 5, pp. 1081-1087, (2005).

Kondyurin et al., "Plasma Immersion ion implantation of polyethylene," Vacuum, vol. 64, pp. 105-111, (2002).

Kong et al., "Polyelectrolyte-functionalized multiwalled carbon nanotubes: preparation, characterization and layer-by-layer self-assembly," Polymer, vol. 46, pp. 2472-2485, (2005).

Konig et al., "Nanoprocessing with nanojoule near-infrared femtosecond laser pulses," Medical Laser Application, vol. 20, pp. 169-184, (2005).

Konishi et al., "Morphology Control of Dy-Ni Alloy Films by Electrochemical Displantation," Electrochemical and Solid-State Letters, vol. 5, No. 12, pp. B37-B39, (2002).

Koo et al., "Co-regulation of cell adhesion by nanoscale RGD organization and mechanical stimulus," Journal of Cellular Science, vol. 115, Part 7, pp. 1423-1433, Apr. 1, 2002.

Kopanski et al., "Scanning Kelvin Force Microscopy For Characterizing Nanostructures in Atmosphere," Characterization and Metrology for Nanoelectronics: 2007 International Conference on Frontiers of Characterization and Metrology. American Institute of Physics Conference Proceedings, vol. 931, pp. 530-534, Sep. 26, 2007.

Kostov et al., "Two Dimensional Computer Simulation of Plasma Immersion Ion Implantation," Brazilian Journal of Physics, vol. 34, No. 4B, pp. 1689-1695, Dec. 2004.

Kötz et al., "XPS Studies of Oxygen Evolution on Ruand $RuO_2$ Anodes," Journal of Electrochemical Society: Electrochemical Science and Technology, pp. 825-829, Apr. 1983.

Kowalski et al., "Corrosion protection of steel by bi-layered polypyrrole doped with molybdophosphate and naphthalenedisulfonate anions," Corrosion Science, Vo. 49, pp. 1635-1644, ( 2007).

Kraft et al., "Thin films from fast clusters: golden TiN layers on a room temperature substrate" Surface and Coatings Technology 158-159, pp. 131-135, (2002).

Krumeich et al., "HyFraSurf-Advanced Surface Technology for Superior Electrode Performance," European Cells and Materials, vol. 1, Suppl. 1, p. 43, (2001).

Kumar et al., "Influence of electric field type on the assembly of single walled carbon nanotubes," Chemical Physics Letters, vol. 383, pp. 235-239, (2004).

Kumar et al., "Polyanhydrides: an overview," Advanced Drug Delivery Reviews, vol. 54, pp. 889-910, (2002).

Kunitake et al., "Molecular imprinting in ultrathin titania gel films via surface sol-gel process," Analytica Chimica Acta, vol. 504, pp. 1-6, (2004).

Kurth et al., "Multilayers on Solid Planar Substrates: From Structure to Function," Multilayer Thin Films: Sequential Assembly of Nanocomposite Materials, Chapter 14, pp. 393-426, Mar. 7, 2003.

Kutsenko et al., "Structural changes in Mg alloy induced by plasma immersion ion implantation of Ag," Acta Materialia, vol. 52, pp. 4329-4335, (2004).

Kutz, "Biomaterials to Promote Tissue Regeneration," in Standard Handbook of Biomedical Engineering and Design, ISBN 0-07-135637-1, pp. 16.13-16.29, (2003).

Kvastek et al., "Electochemical properties of hydrous rithenium oxide films formed and measured at different potentials," Journal of Electroanalytical Chemistry, vol. 511, pp. 65-78, (2001).

Lakard et al., "Adhesion and proliferation of cells on new polymers modified biomaterials," Bioelectrochemistry, vol. 62, pp. 19-27, (2004).

Lakatos-Varsanyi et al., "Cyclic voltammetry measurements of different single-, bi- and multilayer TiN and single layer CrN coatings on low-carbon-steel substrates," Corrosion Science, vol. 41, pp. 1585-1598, (1999).

Lamaka et al., "$TiO_x$ self-assembled networks prepared by templating approach as nanostructured reservoirs for self-healing anticorrosion pre-treatments," Electrochemistry Comunications, vol. 8, pp. 421-428, (2006).

Lamer et al., "The Challenge of Plasma Processing—Its Diversity," Presented at the ASM Materials and Processes for Medical Devices Conference, Aug. 25-27, 2004.

Laser-Induced Forward Transfer (LIFT): Paul Scherrer Institut, (http://materials.web.psi.ch/Research/Thin_Films/Methods/LIFT.htm), downloaded Dec. 7, 2006.

Lau et al., "Hot-wire chemical vapor deposition (HWCVD) of fluorocarbon and organosilicon thin films," Thin Solid Films, vol. 395, pp. 288-291, (2001).

LaVan et al., Small-scale systems for *in vivo* drug delivery, Nature Biotechnology, vol. 21, No. 10, pp. 1184-1191, Oct. 2003.

Leary-Swan et al., "Fabrication and evaluation of nanoporous alumina membranes for osteoblast culture," Journal of Biomedical Materials Research: Part A, vol. 72A, pp. 288-295, (2005).

Lee et al., "A Template-Based Electrochemical Method for the Synthesis of Multisegmented Metallic Nanotubes," Angewandte Chemie, vol. 44, pp. 6050-6054, (2005).

Lee et al., "Biocompatibility and Charge Injection Property of Iridium Film Formed by Ion Beam Assisted Deposition," Biomaterials, vol. 24, pp. 2225-2231, (2003).

Lee et al., "Structural characterization of porous low-k thin films prepared by different techniques using x-ray porosimetry," Journal Of Applied Physics, vol. 95, No. 5, Mar. 1, 2004.

Lee et al., "A study on electrophoretic deposition of Ni nanoparticles on pitted Ni alloy 600 with surface fractality", Journal of Colloid and Interface Science, vol. 308, pp. 413-420, (2007).

Lefaux et al., "Polyelectrolyte Spin Assembly: Influence of Ionic Strenght on the Growth of Multilayered Thin Films," Journal of Polymer Science Part B: Polymer Physics, vol. 42, pp. 3654-3666, (2004).

Lei et al., "Fabrication of Highly Ordered Nanoparticle Arrays Using Thin Porous Alumina Masks," Advanced Materials for Micro- and Nano-Systems (AMMNS), Jan. 2001.

Leng et al., "Mechanical properties and platelet adhesion behavior of diamond-like carbon films synthesized by pulsed vacuum arc plasma deposition," Surface Science, vol. 531, pp. 177-184, (2003).

Lenza et al., "In vitro release kinetics of proteins from bioactive foams," Journal of Biomedical Materials Research: A, vol. 67, No. 1, pp. 121-129, Oct. 2003.

Leoni et al., "Characterization of Nanoporous Membranes for immunoisolation: Diffusion Properties and Tissue Effects," Biomedical Microdevices, vol. 4, No. 2, pp. 131-139, (2002).

Leoni et al., "Nanoporous Platforms for Cellular Sensing and Delivery," Sensors, 51(2), pp. 111-120, (2002).

Leung et al., "Fabrication of photonic band gap crystal using microtransfer molded templates," Journal of Applied Physics, vol. 93, No. 10, pp. 5866-5870, May 15, 2003.

Lewis et al., "Silicon nonopillars formed with gold colloidal partical masking," Journal of Vacuum Science Technology B, vol. 16, No. 6, pp. 2938-2941, Nov./Dec. 1998.

Li et al., "A simple approach to fabricate amorphous silicon pattern on single crystal silicon," Tribology International, vol. 40, pp. 360-364, (2007).

Li et al., "Bioactive Hydroxyapatite Composite Coating Prepared by SOL-Gel Process," Journal of Sol-Gel Science and Technology, vol. 7, pp. 27-34, (1996).

Li et al., "Fabrication and Microstructuring of Hexagonally Ordered Two-Dimensional Nanopore Arrays in Anodic Alumina," Advanced Materials, vol. 11, pp. 483-487, (1999).

Li et al., "Hexagonal pore arrays with a 50-420 nm interpore distance formed by self-organization in anodic alumina," Journal of Applied Physics, vol. 84, No. 11, pp. 6023-6026, Dec. 1, 1998.

Li et al., "Improved biological performance of Ti implants due to surface modification by micro-arc oxidation," Biomaterials, vol. 25, pp. 2867-2875, (2004).

Li et al., "On the growth of highly ordered pores in anodized aluminum oxide," Chem. Mater., vol. 10, pp. 2470-2480, (1999).

Li et al., "pH-compensation effect of bioactive inorganic fillers on the degradation of PLGA," Composites Science and Technology, vol. 65, pp. 2226-2232, (2005).

Li et al., "Polycrystalline nanopore arrays with haxagonal ordering on aluminum," Journal of Vacuum Science Technology: A, vol. 17, pp. 1428-1431, (1999).

Li et al., "A novel method for preparing surface-modified $Mg(OH)_2$ nanocrystallines," Materials Science and Engineering A, 452-453, pp. 302-305, (2007).

Li, "Poly(L-glutamic acid)-anticancer drug conjugates," Advanced Drug Delivery Reviews, vol. 54, pp. 695-713, (2002).

Liaw et al., "Process Monitoring of Plasma Electrolytic Oxidation," presented at the 16th World Conference on Nondestructive Testing, Montreal, Canada, Aug. 30-Sep. 3, 2004.

Liebling et al., "Optical Properties of Fibrous Brucite from Asbestos, Quebec", American Mineralogist, vol. 57, pp. 857-864, (1972).

Lim et al., "Systematic variation in osteoblast adhaesion and phenotype with substratum surface characteristics," Journal of Biomedical Materials and Research, vol. 68A, No. 3, pp. 504-511, (2004).

Lim et al., "UV-Driven Reversible Switching of a Roselike Vanadium Oxide Film between Superhydrophobicity and Superhydrophilicity," Journal of American Chemical Society, vol. 129, pp. 4126-4129, Mar. 15, 2007.

Lin et al., "PWA-doped $PEG/SiO_2$ proton-conducting hybrid membranes for fuel cell applications," Journal of Membrane Science, vol. 254, pp. 197-205, (2005).

Lindstrom et al., "A New Method for Manufacturing Nanostructured Electrodes on Glass Substrates," Solar Energy Materials & Solar Cells, vol. 73, pp. 91-101 (2002).

Lippert et al., "Chemical and Spectroscopic Aspects of Polymer Ablation: Special Features and Novel Directions," Chemical Reviews, vol. 103, pp. 453-485, (2003).

Liu et al., "A metal plasma source ion implantation and deposition system," American Institute of Physics, Review of Scientific Instruments, vol. 70, No. 3, pp. 1816-1820, Mar. 1999.

Liu et al., "Electrodeposition of Polypyrrole Films on Aluminum from Tartrate Aqueous Solution," Journal of Brazilian Chemical Society, vol. 18, No. 1, pp. 143-152, (2007).

Liu et al., "Surface modification of titanium, titanium alloys, and related materials for biomedical applications," Materials Science and Engineering R, vol. 47, pp. 49-121, (2004).

Lu et al., "Fabricating Conducting Polymer Electrochromic Devices Using Ionic Liquids," Journal of the Electrochemical Society, vol. 151, No. 2, pp. H33-H39, (2004).

Lu et al., "Micro and nano-fabrication of biodegradable polymers for drug delivery," Advanced Drug Delivery Reviews, vol. 56, pp. 1621-1633, (2004).

Lv et al., "Controlled growth of three morphological structures of magnesium hydroxide nanoparticles by wet precipitation method," Journal of Crystal Growth, vol. 267, pp. 676-684, (2004).

Lv et al., "Controlled synthesis of magnesium hydroxide nanoparticles with different morphological structures and related properties in flame retardant ethyolene-vinyl acetate blends", Nanotechnology, vol. 15, pp. 1576-1581, (2004).

Lv et al., "In situ synthesis of nanolamellas of hydrophobic magnesium hydroxide", Colloids and Surfaces A: Physicochemical and Engineering Aspects, vol. 296, pp. 97-103, (2007).

Maeda et al., "Effect of Silica Addition on Crystallinity and Photo-Induced Hydrophilicity of Titania-Silica Mixed Films Prepared by Sol-Gel Process," Thin Solid Films, vol. 483, pp. 102-106, (2005).

Maehara et al., "Buildup of Multilayer Structures of Organic-Inorganic Hybrid Ultra Thin Films by Wet Process," Thin Solid Films, vol. 438-439, pp. 65-69, (2003).

Maheshwari et al., "Cell adhesion and motility depend on nanoscale RGD clustering," Journal of Cell Science, vol. 113, Part 10, pp. 1677-1686, May 2000.

Maitz et al., "Blood Compatibility of Titanium Oxides with Various Crystal Structure and Element Doping," Journal of Biomaterials Applications, vol. 17, pp. 303-319, Apr. 2003.

Manna et al., "Microstructural Evalution of Laser Surface Alloying of Titanium with Iridium," Scripta Materialia, vol. 37, No. 5, pp. 561-568, (1997).

Manoharan et al., "Ordered macroporous rutile titanium dioxide by emulsion templating," Proceedings of SPIE, vol. 3937, pp. 44-50, (2000).

Mantis Deposition Ltd., "Nanocluster Deposition," Thame, Oxforshire, United Kingdom, [downloaded on Feb. 2, 2007], (http://www.mantisdeposition.com/nanocluster.html).

Martin et al., "Microfabricated Drug Delivery Systems: Concepts to Improve Clinical Benefit," Biomedical Microdevices, vol. 3, No. 2, pp. 97-107, Jun. 2001.

Martin, "Pulsed Laser Deposition and Plasma Plume Investigations," Andor Technology, Ltd. (2003).

Masuda et al., "Highly ordered nanochannel-array architecture in anodic alumina," Applied Physics Letters, vol. 71, pp. 2770-2772, (1997).

Matijević, "Colloid Chemical Aspects of Corrosion of Metals", Pure & Applied Chemisty, vol. 52, pp. 1179-1193, (1980).

Mattox, "Introduction: Physical Vapor Deposition (PVD) Processes," Vacuum Technology & Coating, pp. 60-63, Jul. 2002.

Mattox, "The History of Vacuum Coating Technology: Part V," Vacuum Technology & Coating, pp. 32-37, Oct. 2002.

Mattox, "The History of Vacuum Coating Technology: Part VI," Vacuum Technology & Coating, pp. 52-59, Oct. 2002.

Mauritz Group Homepage, "Sol-Gel Chemistry and Technology," (htty://www.psrc.usin.edu/mauritz/solgel.html) (downloaded [2006]).

McGuigan et al., "The influence of biomaterials on endothelial cell thrombogenicity," Biomaterials, vol. 28, pp. 2547-2571, (2007).

McNally et at., "Cathodic Electrodeposition of Cobalt Oxide Films Using Polyelectrolytes," Materials Chemistry and Physics, vol. 91, pp. 391-398, (2005).

Meijer et al., "Laser Machining by short and ultrashort pulses, state of the art and new opportunities in the age of the photons," Annals of CIRP 2002: Manufacturing Technology, vol. 51, No. 2, pp., 531-550, (2002).

Meletis et al., "Electrolytic plasma processing for cleaning and metal-coating of steel surfaces," Surface and Coatings Technology, vol. 150, pp. 246-256, (2002).

Merriam-Webster's Dictionary Website: For definition of Strut, [first cited Jul. 21, 2010], (http://www.merriam-webster.com/dictionary/strut).

MicroFab Technologies Inc. "MicroFab: Biomedical Applications—Stents," [first downloaded Mar. 23, 2007], (http://www.microfab.com/technology/biomedical/Stents.html).

Mikhaylova et al., "Nanowire formation by electrodeposition in modified nanoporous polycrystalline anodic alumina templates," Mat. Res. Soc. Symp. Proc., vol. 704, pp. w6.34.1-W6.34.6, (2002).

Miller et al., "Endothelial and vascular smooth muscle cell function on poly(lactic-co-glycolic acid) with nano-structured surface features," Biomaterials, vol. 25, No. 1, pp. 53-61, (2004).

Miller et al., "Mechanism(s) of increased vascular cell adhesion on nanostructured poly(lactic-coglycolic acid) films," Journal of Biomedical Materials Research A, vol. 73, No. 4, pp. 476-484, (2005).

MIV Therapeutics, "Hydroxyapatite Coating," [first downloaded Jun. 25, 2003], (http://www.mivtherapeutics.com/technology/hap/).

Mobedi et al., "Studying the Degradation of Poly($L$-lactide) in Presence of Magnesium Hydroxide", Iranian Polymer Journal, vol. 15, No. 1, pp. 31-39, (2006).

Mu et al., "A novel controlled release formulation for the anticancer drug paclitaxel (Taxol): PLGA nanoparticles containing vitamin E TPGS," Journal of Controlled Release, vol. 86, pp. 33-48, (2003).

Mu et al., "Vitamin E TPGS used as emulsifier in the solvent evaporation/extraction technique for fabrication of polymeric nanospheres O for controlled release of paclitaxel (Taxol)", Journal of Controlled Release, vol. 80, pp. 129-144, (2002).

Muller et al., "Solid lipid nanoparticles (SLN) for controlled drug delivery: a review of the state of the art," European Journal of Pharmaceutics and Biopharmaceutics, vol. 50, pp. 161-177, (2000).

Munchow et al., "Poly[(oligoethylene glycol) Dihydroxytitanate] as Organic-Inorganic Polymer-Electrolytes," Electrochimica Acta, vol. 45, pp. 1211-1221, (2000).

Murray et al., "Electrosynthesis of novel photochemically active inherently conducting polymers using an ionic liquid electrolyte," Electrochimica Acta, vol. 51, pp. 2471-2476, (2006).

Naganuma et al., "Preparation of Sol-Gel Derived Titanium Oxide Thin Films Using Vacuum Ultraviolet irradiation with a Xenon Excimer Lamp," Japanese Journal of Applied Physics, vol. 43, No. 9A, pp. 6315-6318, (2004).

Nair et al., "Biodegradable polymers as biomaterials", Progress in Polymer Science, vol. 32, pp. 732-798, (2007).

Nakajima et al., "Effect of Vacuum Ultraviolet Light Illumination on the Crystallization of Sol-Gel-Derived Titanium Dioxide Precursor Films," Surface & Coatings Technology, vol. 192, pp. 112-116, (2005).

Nakayama et al., "Fabrication of drug-eluting covered stents with micropores and differential coating of heparin and FK506," Cardiovascular Radiation Medicine, vol. 4, pp. 77-82, (2003).

NanoBiotech News, vol. 2, No. 26, Jun. 30, 2004.

Nanoparticle coatings: Application note, "Antimicrobial Coatings," Mantis Deposition Ltd, (2006).

Nanu, "Nanostructured TiO2-CuInS2 based solar cells," Symposium D, Thin Film and Nano-Structured Materials for Photovoltaics, E-MRS Spring Meeting 2003, Jun. 10-13, 2003.

NASA Glenn Research Center, "Fast Three-Dimensional Method of Modeling Atomic Oxygen Undercutting of Protected Polymers," [first downloaded on Jul. 3, 2003], (http://www.grc.nasa.gov/WWW/epbranch/suurtxt/surfaceabs.htm).

Neves et al., "The morphology, mechanical properties and ageing behavior of porous injection molded starch-based blends for tissue engineering scaffolding," Materials Science and Engineering, vol. C25, pp. 195-200, (2005).

Newman et al., "Alloy Corrosion," MRS Bulletin, pp. 24-28, Jul. 1999.

Ngaruiya et al., "Structure formation upon reactive direct current magnetron sputtering of transition metal oxide films," Applied Physics Letters, vol. 85, No. 5, pp. 748-750, Aug. 2, 2004.

Ngaruiya et al., "The reactive DC-Magnetron Sputtering Process," (circa 2004).

Nicoll et al., "In vitro release kinetics of biologically active transforming growth factor-beta 1 from a novel porous glass carrier," Biomaterials, vol. 18, Issue 12, pp. 853-859, (1997).

Nicoll et al., "Nanotechnology and Biomaterials—Drugs, Drug Delivery Systems, Quantum Dots and Disease Treatment," Azom.com, [first downloaded Mar. 22, 2004], (http://www.azom.com/details.asp?ArticleID=1853).

Nie et al., "Deposition of layered bioceramic hydroxyapatite/$TiO_2$ coatings on titanium alloys using a hybrid technique of micro-arc oxidation and electrophoresis," Surface Coatings Technology, vol. 125, pp. 407-414, (2000).

Nishio et al., "Preparation and properties of electrochromic iridium oxide thin film by sol-gel process," Thin Solid Films, vol. 350, pp. 96-100, (1999).

Noguera et al., "3D fine scale ceramic components formed by ink-jet prototyping process," Journal of the European Ceramic Society, vol. 25, pp. 2055-2059, (2005).

O'Brien et al., "Passivation of Nitinol Wire for Vascular Implants-A Demonstration of the Benefits," Biomaterials, vol. 23, pp. 1739-1748, (2002).

Oh et al., "Microstructural characterization of biomedical titanium oxide film fabricated by electrochemical method," Surface & Coatings Technology, vol. 198, pp. 247-252, (2005).

Orloff et al., "Biodegradable implant strategies for inhibition of restenosis," Advanced Drug Delivery Reviews, vol. 24, pp. 3-9, (1997).

Oxford Applied Research, "Nanocluster Deposition Systems—Nanodep60," [first downloaded Nov. 3, 2006], (http://www.oaresearch.co.uk.nanodep60.htm).

Paik et al., "Micromachining of mesoporous oxide films for microelectromechanical system structures," Journal of Materials Research, vol. 17, pp. 2121-2129, (2002).

Palasis et al., "Analysis of Adenoviral Transport Mechanisms in the Vessel Wall and Optimization of Gene Transfer Using Local Delivery Catheters," Human Gene Therapy, vol. 11, pp. 237-246, Jan. 20, 2000.

Palasis et al., "Site-Specific Drug Delivery from Hydrogel Coated Angioplasty Catheters," Proceedings of the International Symposium on Controlled Release: Bioactive Materials, vol. 24, pp. 825-826, (1997).

Palmaz et al., "Influence of surface topography on endothelialization of intravascular metallic material," Journal of Vascular and Interventional Radiology, vol. 10, No. 4, pp. 439-444, (1999).

Pang et al., "Electrodeposition of composite hydroxyapatite-chitosan films," Materials Chemistry and Physics, vol. 94, pp. 245-251, (2005).

Pang et al., "Electropolymerization of high quality electrochromic poly(3-alkyl-thiophene)s via a room ternmperature ionic liquid," Electrochimica Acta, vol. 52, pp. 6172-6177, (2007).

Park et al., "Multilayer Transfer Printing for Polyelectrolyte Multilayer Patterning: Direct Transfer of Layer-by-Layer Assembled Micropatterned Thin Films," Advanced Materials, vol. 16, No. 6, pp. 520-525, Mar. 18, 2004.

Park et al., "Novel Phenylethynyl Imide Silanes as Coupling Agents for Titanium Alloy," The 22nd Annual Meeting of the Adhesion Society, Feb. 21-24, 1999.

Park et al., "Cathodic electrodeposition of $RuO_2$ thin films from $Ru(III)Cl_3$ solution", Materials Chemistry and Physics, vol. 87, pp. 59-66, (2004).

Park et al., "Microstructural change and precipitation hardeningin melt-spun Mg-X-Ca alloys," Science and Technology of Advanced Materials, vol. 2, pp. 73-78, (2001).

Pathan et al., "A chemical route to room-temperature synthesis of nanocrystalline TiO2 thin films," Applied Surface Science, vol. 246, pp. 72-76, (2005).

Pelletier et al., "Plasma-based ion implantation and deposition: A review for physics, technology, and applications," Lawrence Berkeley and National Laboratory, pp. 1-68, May 16, 2005.

Peng et al., "Role of polymers in improving the results of stenting in coronary arteries," Biomaterials, vol. 17, No. 7, pp. 658-694 (1996).

Perlman et al., "Evidence for rapid onset of apoptosis in medial smooth muscle cells after balloon injury," Circulation, vol. 95, No. 4, pp. 981-987, Feb. 18, 1997.

Pharmaceutical Science Technology, Chapter 6: Electropolymerization, pp. 24-28, (2007).

Piazza et al., "Protective diamond-like carbon coatings for future optical storage disks," Diamond & Related Materials, vol. 14, pp. 994-999, (2005).

Pitt et al., "Attachment of hyaluronan to metallic surfaces," Journal of Biomedical Materials Research, vol. 68A, pp. 95-106, (2004).

Polygenetics, "Advanaced Drug Delivery," [first downloaded on May 4, 2007], 5 pages, (http://www.polygenetics.com/drug_delivery.htm).

Ponte et al., "Porosity determination of nickel coatings on copper by anodic voltammetry," Journal of Applied Electrochemistry, vol. 32, pp. 641-646, (2002).

Prior Clinicals, Boston Scientific memo, (more than a year prior to May 23, 2007).

Prokopowicz et al., "Synthesis and Application of Doxorubicin-Loaded Silica Gels as Solid Materials for Spectral Analysis," Talanta, vol. 65, pp. 663-671, (2005).

Prokopowicz et al., "Utilization of Standards Generated in the Process of Thermal Decomposition Chemically Modified Silica Gel or a Single Point Calibration of a GC/FID System," Talanta, vol. 44, pp. 1551-1561, (1997).

Pulsed Laser Deposition, (http://www.physandtech.net), Apr. 28, 2001.

PVD Materials—Materials Available for Physical Vapour Deposition (PVD) from Williams Advanced Materials. (www.azom.com), [first downloaded Apr. 28, 2006].

Qasem et al., "Kinetics of Paclitaxel 2'-N-Methylpyridinium Mesylate Decomposition," AAPS PharmaSciTech, vol. 4, No. 2, Article 21, (2003).

Qian et al., "Preparation, characterization and enzyme inhibition of methylmethacrylate copolymer nanoparticles with different hydrophilic polymeric chains," European Polyer Journal, vol. 42, pp. 1653-1661, (2006).

Qiang et al., "Hard coatings (TiN, $Ti\chi Al_{1-\chi}N$) deposited at room temperature by energetic cluster impact," Surface and Coatings Technology, 100-101, pp. 27-32, (1998).

Qiu et al., "Self-assembled growth of MgO nanosheet arrays via a micro-arc oxidations technique," Applied Surface Science vol. 253, pp. 3987-3990, (2007).

Radin et al., "Biocompatible and Resorbable Silica Xerogel as a Long-Term Controlled Release Carrier of Vancomycin," Orthopaedic Research Society, 47th Annual Meeting, Feb. 25-28, 2001, San Francisco, CA.

Radin et al., "Silica sol-gel for the controlled release of antibiotics. I. Synthesis, characterization, and in vitro release," Journal of Biomedical Materials Research, vol. 27, No. 2, pp. 313-320, Nov. 2001.

Radin, S. et al., "In vitro bioactivity and degradation behavior of silica xerogels intended as controlled release materials," Biomaterials. vol. 23, No. 15, pp. 3113-3122, Aug. 2002.

Radtchenko et al., "A Novel Method for Encapsulation of Poorly Water-Soluble Drugs: precipitation in Polyelectrolyte multilayer shells", International Journal of Pharmaceutics, vol. 242, pp. 219-223, (2002).

Razzacki et al., "Integrated microsystems for controlled drug delivery," Advanced Drug Delivery Reviews, vol. 56, pp. 185-198, (2004).

Rees et al., "Glycoproteins in the Recognition of Substratum by Cultured Fibroblasts," Symposia of the Society for Experimental Biology: Cell-Cell Recognition, No. 32, pp. 241-260 (1978).

Reyna-Gonzales et al., "Influence of the acidity level on the electropolymerization of N-vinylcarbazole: Electrochemical study and characterization of poly(3,6-N-vinylcarbazole)," Polymer, vol. 47, pp. 6664-6672, (2006).

Rice, "Limitations of pore-stress concentrations on the mechanical properties of porous materials," Journal of Material Science, vol. 32, pp. 4731-4736, (1997).

Ristoscu, "Thin Films and Nanostructured Materials." [first downloaded Jul. 3, 2003], (http://www..fisica.unile.it/radiazioni/ThinYO2Ofilms%20and%2Onanostmctured%20materials.htm).

Robbie et al., "Advanced techniques for glancing angle deposition," Journal of Vacuum Science and Technology B, vol. 16, No. 3, pp. 1115-1122, (May/Jun. 1998).

Robbie et al., "Sculptured thin films and glancing angle deposition: Growth mechanics and applications," Journal of Vacuum Science Technology: A., vol. 15, pp. 1460-1465, (1997).

Roder et al., "Tuning the microstructure of pulsed laser deposited polymer-metal nanocomposites," Applied Physics A. vol. 85, pp. 15-20 (2006).

Rosen et al., "Fibrous Capsule Formation and Fibroblast Interactions at Charged Hydrogel Interfaces," Hydrogels or Medical and Related Applications, Chapter 24, pp. 329-343, Jun. 1, 1976.

Rossi et al., "Pulsed Power Modulators for Surface Treatment by Plasma Immersion Ion Impantation," Brazilian Journal of Physics, vol. 34, No. 4B, pp. 1565-1571, Dec. 2004.

Routkevitch, "Nano- and Microfabrication with Anodic Alumina: A Route to Nanodevices," Foresight Institute 9th Conference on Molecular Nanotechnology, Nov. 8-11, 2001, Santa Clara, CA.

Ryu et al., "Biomimetic apatite induction on Ca-containing titania," Current Applied Physics, vol. 5, pp. 512-515, (2005).

Santos et al., "Si-Ca-P xerogels and bone morphogenetic protein act synergistically on rat stromal marrow cell differentiation in vitro," Journal of Biomedical Materials Research, vol. 41, No. 1, pp. 87-94, Jul. 1998.

Santos et al., "Sol-Gel Derived Carrier for the Controlled Release of Proteins," Biomaterials, vol. 20, pp. 1695-1700, (1999).

Sardella et al., "Plasma-Aided Micro- and Nanopatterning Processes for Biomedical Applications," Plasma Processes and Polymers, vol. 3, pp. 456-469, (2006).

Sasahara et al., "Macroporous and nanosized ceramic films prepared by modified sol-gel methods with PMMA microsphere templates," Journal of the European Ceramic Society, vol. 24, pp. 1961-1967, (2004).

Sawitowski, "Nanoporous alumina for implant coating—A novel approach towards local therapy,"NanoMed 3rd Workshop, Medical Aplications of nanotechnology, Berlin, Feb. 17-18, 2003.

Sawyer et al., "The Role of Electrochemical Surface Properties in Thrombosis at Vascular Interfaces: Cumulative Experience of Studies in Animals and Man," Bulletin of the New York Academy of Medicine, Second Series, vol. 48, No. 2, pp. 235-256, (1972).

Sawyer, "Electrode-Biologic Tissue Interreactions at Interfaces—A Review;" Biomat. Med. Dev. Art. Org., 12(3-4), pp. 161-196 (1984).

Schetsky, "Shape Memory Alloys", Encyclopedia of Chemical Technology (3rd ed.), John Wiley & Sons, vol. 20, pp. 726-736, (1982).

Schlottig et al., "Characterization of nanoscale metal structures obtained by template synthesis," Fresenius' Journal of Analytical Chemistry, vol. 361, pp. 684-686, (1998).

Schneider, "Laser Cladding with Powder: Effect of some machining parameters on clad properties," Doctoral Thesis—University of Twente, The Netherlands, ISBN 9036510988, Mar. 1998.

Schnitzler et al., "Organic/Inorganic Hybrid Materials Formed From TiO2 Nanoparticles and Polyaniline," Journal of Brazilian Chemistry Society, vol. 15, No. 3, pp. 378-384, (2004).

Selective laser sintering, from Wikipedia, (http://en.wikipedia.org/wiki/Selective_laser_sintering), downloaded on Sep. 28, 2007.

Senior et al., "Synthesis of tough nanoporous metals by controlled electrolytic dealloying," Nanotechnology, vol. 17, pp. 2311-2316, (2006).

Serra et al., "Preparation of functional DNA microarrays through laser-induced forward transfer," Applied Physics Letters, vol. 85, No. 9, pp. 1639-1641, Aug. 30, 2004.

Serruys et al., "The Effect of Variable Dose and Release Kinetics on Neointimal Hyperplasia Using a Novel Paclitaxel—Eluting Stent Platform," Journal of the American College of Cardiology, vol. 46, No. 2, pp. 253-260, Jul. 19, 2005.

Sgura et al., The Lunar Stent: characteristics and clinical results, Herz, vol. 27, pp. 1 -X, (2002).

Shabalovskaya et al., "Surface Conditions of Nitinol Wires, Tubing, and As-Cast Alloys. The Effect of Chemical Etching, Aging in Boiling Water, and Heat Treatment," Wiley Periodicals, Inc., Journal of Biomedical Materials Research Part B: Appiled Biomaterials, vol. 65B: pp. 193-203, (2003).

Shamiryan et al., "Comparative study of SiOCH low-k films with varied porosity interacting with etching and cleaning plasma," Journal of Vacuum Science Technology B, vol. 20, No. 5, pp. 1923-1928, Sep./Oct. 2002.

Shang et al., "Structure and photocatalytic characters of TiO2 film photocatalyst coated on stainless steel webnet," Journal of Molecular Catalysis A: Chemical, vol. 202, pp. 187-1995, (2003).

Shao et al., "Fiber mats of poly(vinyl alcohol)/silica composite via Electrospinning," Materials Letters, vol. 57, pp. 1579-1584, (2003).

Shchukin et al., "Micron-scale hollow polyelectrolyte capsules with naosized magnetic $Fe_3O_4$ inside," Materials Letters, vol. 57, pp. 1743-1747, (2003).

Shevchenko et al., "Porous Surface of NiTi Alloy Produced by Plasma Ion Implantation," Institute of Ion Beam Physics and Materials Research, May 2005.

Shevchenko, "Formation of nonoporous structures on stainless steel surface," Report, Apr. 2007.

Shibli et al., "Development of phosphate inter layered hydroxyapatite coating for stainless steel implants", Applied Surface Science, vol. 254, pp. 4103-4110, (2008).

Shockravi et al., "Soluable and thermally stable polyamides bearing 1,1'-thiobis(2-naphthoxy) groups," European Polymer Journal, vol. 43, pp. 620-627, (2007).

Shustak et al., "n-Alkanoic Acid Monolayers on 316L Stainless Steel Promote the Adhesion of electropolymerized Polypyrrole Films," Langmuir, vol. 22, pp. 5237-5240, (2006).

Siegfried et al., "Reactive Cylindrical Magnatron Deposition of Titanium Nitride and Zirconium Nitride Films," Society of Vacuum Coaters, 39th Annual Technical Conference Proceedings, pp. 97-101, (1996).

Silber et al., "A new stainless-steel-free stent with a potential of artifact free magnetic resonance compatibility: first clinical experience (Ein neuer Edelstahl-freier Stent mit Potential zur artefaktfreien MR-Kompatibilität: Erste klinische Erfahrungen)," German Society for Cardiology—Heart and Cardiovascular Research (Deutche Gesellschaft fur Kardiologie—Herz and Kreislaufforschung), Oct. 30, 2005.

Silber et al., "A new stainless-steel-free stent with a potential of artifact free magnetic resonance compatibility: first clinical experience," Abstract and Poster, May 2006.

Silber, "LUSTY-FIM Study: Lunar Starflex First In Man Study, " PowerPoint presentation at the Paris Course on Revascularization, May 2003.

Silber, "Ein edelstahfreier stent aus niobium mit iridiumoxyd (IrOx)-beschichtung: Erste Ergebnisse der LUSTY-studie" (*Stainless steel-free Stent out of niobium with iridiumoxyd (IrOx)-coating: Initial results of the LUSTY-study*), PowerPoint presentation on Oct. 15, 2004.

Silber, "LUSTY-FIM Study: Lunar Starflex First In Man Study," PowerPoint presentation in 2003.

Silber, "Niobium/iridiumoxide Stents: LUSTY randomized trial, LUNAR ROX registry," PowerPoint presentation in 2003.

Silva et al., "Electrochemical characterisation of oxide films formed on Ti-6A1-4V alloy implanted with Ir for Bioengineering applications," Electrochimica Acta, vol. 43, Nos. 1-2, pp. 203-211, (1998).

Simon et al., "Influence of topography on endothelialization of stents: Clues for new designs,"Journal of Long-Term Effects Of Medical Implants, Voo. 10, No. 1-2, pp. 143-151, (2000).

Singer, "Paclitaxel Poliglumex (XYOTAX, CT-2103): A Macromolecular Taxane," Journal of Controlled Release, vol. 109, 120-126, (2005).

Singh et al., "Review: Nano and macro-structured component fabrication by electron beam-physical vapor deposition (EB-PVD)," Journal of Materials Science, vol. 40, pp. 1-26, (2005).

Sniadecki et al., "Nanotechnology for Cell-Substrate Interactions," Annals of Biomedical Engineering, vol. 34, No. 1, pp. 59-74, Jan. 1, 2006.

Sofield et al., "Ion beam modification of polymers," Nuclear Instruments and Methods in Physics Research, vol. B67, pp. 432-437, (1992).

Soler-Illia et al., "Block Copolymer-Templated Mesoporous Oxides," Current Opinion in Colloid and Interface Science, vol. 8, pp. 109-126, (2003).

Song et al., "Biomimetic apatite coatings on micro-arc oxidized titania," Biomaterials, vol. 25, pp. 3341-3349, (2004).

Sousa et al., "New Frontiers in Cardiology: Drug-Eluting Stents: Part I," Circulation: Journal of the Americal Heart Associate, vol. 107, pp. 2274-2279, http/www.circ.ahajournals.org, (2003).

Spasova et al., "Magnetic and optical tunable microspheres with a magnetite/gold nanoparticle shell," Journal of Material Chemisty, vol. 115, pp. 2095-2098, (2005).

Sprague et al., "Endothelial cell migration onto metal stent surfaces under static and flow conditions," Journal of Long-Term Effects of Medical Implants, vol. 10, No. 1-2, pp. 97-110, (2000).

Startschuss fur "lusty" -studie, (*Launch of "lusty" -study*), Cardio News, Oct. 2002.

Stucky "High Surface Area Materials," Published: Jan. 1998, WTEC Hyper-Librarian, (http://www.wtec.org/loyola/nano/US.Review/07_03.htm).

Studart et al., "Colloidal Stabilization of Nanoparticles in Concentrated Suspensions," Langmuir, vol. 23, pp. 1081-1090, (2007).

Sun et al., "Construction of Size-Controllable Hierarchical Nanoporous $TiO_2$ Ring Arrays and Their Modifications," Chem. Mater, vol. 18, pp. 3774-3779, (2006).

Sun et al., "Non-Fouling Biomaterial Surfaces: II Protein Adsorption on Radiation Grafted Polyethylene Glycol Methacrylate Copolymers," Polymer Preprints, vol. 28, No. 1, pp. 292-294, Apr. 1987.

Sundararaj an et al., "Mechanisms underlying the formation of thick alumina coatings through the MAO coating technology," Surface and Coatings Technolgy, vol. 167, pp. 269-277, (2003).

Sung et al., "Formation of Nanoporous and Nanocrystalline Anatase Films by Pyrolysis of $PEO-TiO_2$ Hybrid Films," Journal of Crystal Growth, vol. 286, pp. 173-177, (2006).

Szycher et al., "Drug-Eluting Stents to Prevent Coronary Restenosis," CardioTech International, (2002).

Tabata et al., "Generalized Semiempirical Equations for the Extrapolated Range of Electronics," Nuclear Instruments and Methods, vol. 103, pp. 85-91, Mar. 28, 1972.

Takitani et al., "Desorption of Helium from Austenitic Stainless Steel Heavily Bombarded by Low Energy He Ions," Journal of Nuclear Materials, vol. 329-333, pp. 761-765, (2004).

Tamura et al., "Surface Hydroxyl Site Densities on Metal Oxides as a Measrure for the Ion-Exchange Capacity," Journal of Colloid and Interface Science, vol. 209, pp. 225-231, (1999).

Tan et al., "Corrosion and wear-corrosion behavior of NiTi modified by plasma source ion implantation," Biomaterials, vol. 24, pp. 3931-3939, (2003).

Tanaka et al., "Micrometer-scale fabrication and assembly using focused ion beam," Thin Solid Films, vol. 509, pp. 113-117, (2006).

Tang et al., "Electrochemical Study of a Polarized Electrochemical Vapor Deposition Process," Journal of the Electrochemical Society, vol. 147, No. 9, pp. 3338-3344, (2000).

Tang et al., "Fabrication of Macroporous Alumina with Tailored Porosity," Jornal of American Ceramic Society, vol. 86, No. 12, pp. 2050-2054, (2003).

Tang et al., "Preparation of Porous anatase titania film," Materials Letters, vol. 58, pp. 1857-1860, (2004).

Tapphorn et al., "The Solid-State Spray Forming of Low-Oxide Titanium Components," Journal of Metals, vol. 50, No. 9, pp. 45-46,76, (1998).

Tassin et al., "Improvement of the Wear Resistance of 316 L Stainless Steel by Laser Surface Alloying," Surface and Coatings Technology, vol. 80, No. 9, pp. 207-210, (1996).

Terlingen, "Functionalization of Polymer Surfaces," Europlasma Technical Paper, pp. 1-29, May 8, 2004.

Terumo Europe, "Terumo Europe N.V. Enrols First Patient in Clinical Trial of the Nobori Drug-Eluting Coronary Stent," Press Release May 26, 2005, (http://www.terumo-europe.com/_press_release/may_262005.html.).

Thierry et al., "Bioactive Coatings of Endovascular Stents Based on Polyelectrolyte Multilayers," Biomacromolecules, vol. 4, pp. 1564-1571, (2003).

Thompson et al., "Tuning compliance of nanoscale polyelectrolyte multilayers to modulate cell adhesion," Biomaterials, vol. 26, pp. 6836-6845, (2005).

Tierno et al., "Using Electroless Deposition for the Preparation of Micron Sized Polymer/Metal Core/Shell Particles and Hollow Metal Spheres," Journal of Physics Chemistry B, vol. 110, pp. 3043-3050, (2006).

Tollon, "Fabrication of coated biodegradable polymer scaffolds and their effects on murin embryonic stem cells," Thesis presented to the University of Florida, (2005).

Tonosaki et al., "Nano-indentation testing for plasma-based ion-implanted surface of plastics," Surface and Coatings Technology, vol. 136, pp. 249-251, (2001).

Torres-Costa et al., "RBS Characterization of Porous Silicon Multilayer Interference Filters," Electrochemical and Solid-State Letters, vol. 7, No. 11, pp. G244-G249 (2004).

Toth et al., "Ar+laser-induced forward transfer (LIFT): a novel method for micrometer-size surface patterning," Applied Surface Science, vol. 69, pp. 317-320, (1993).

Tsyganov et al., "Blood compatibilty of titanium-bases coatings prepared by metal plasma immersion ion implantation and deposition," Applied Surface Science, vol. 235, pp. 156-163, (2004).

Tsyganov et al., "Structure and Properties of Titanium Oxide Layers prepared by Metal Plasma Immersion Ion Implantation and Deposition," Surface & Coatings Technology, vol. 174-175, pp. 591-596, (2003).

Tsyganov et al., "Correlation between blood compatibility and physical surface properties of titanium-based coatings," Surface & Coatings Technology, vol. 200, pp. 1041-1044, (2005).

Uchida et al., "Apatite-forming ability of a zirconia/alumina nanocomposite induced by chemical treatment," Journal of Biomedical Materials Research, vol. 60, No. 2, pp. 277-282, May 2002.

University of Wisconsin, "Effect of Nano-Scale Textured Biomimetic Surfaces on Proliferation and Adhesion of Corneal Epithelial Cells," Materials Research Science and Engineering Center, (1997), (http://mrsec.wisc.edu/Past_proiects/seedproi4/Seedproi4.html).

Uyama et al., "Surface Modifications of Polymers by Grafting," Advances in Polymer Science, vol. 139, (1998).

Valsesia et al., "Selective immobilization of protein clusters on polymeric nanocraters," Advanced Functional Materials, vol. 16, pp. 1242-1246, (2006).

Valsesia, A. et al., "Fabrication of nanostructured polymeric surfaces for biosensing devices," Nanoletters, vol. 4, No. 6, pp. 1047-1050, (2004).

Van Alsten, "Self-Assembled Monolayers on Engineering Metals: Structure, Derivatization, and Utility," Langmuir, vol. 15, pp. 7605-7614, (1999).

Van Den Berg, "Nano particles play with electrons," [first downloaded on Nov. 12, 2003], (http://www.delftoutlook.tudelft.nl/info/index21fd.html?hoofdstuk=Article&ArtID=2243).

van der Eijk et al., "Metal Printing Process Development of a New Rapid Manufacturing Process for Metal Parts," Proceedings of the World PM2004 Conference held in Vienna, Oct. 17-21, 2004.

Van Steenkiste et al., "Kinetic spray coatings," Surface & Coatings Technology, vol. 111, pp. 62-71, (1999).

Vayssieres, "On the design of advanced metal oxide nanomaterials," International Journal of Nanotechnology, vol. 1, Nos. 1/2, (2004).

Velev et al., "Colloidal crystals as templates for porous materials," Current Opinion in Colloid & Interface Science, vol. 5, pp. 56-63, (2000).

Velev et al., "Porous silica via colloidal crystallization," Nature, vol. 389, pp. 447-448, Oct. 2, 1997.

Verheye et al., "Reduced Thrombus Formation by Hyaluronic Acid Coating of Endovascular Devices," Arteriosclerosis, Thrombosis, and Vascular Biology: Journal of the American Heart Association, vol. 20, pp. 1168-1172, (2000).

Vidal et al., "Electropolymerization of pyrrole and immobilization of glucose oxidase in a flow system: influence of the operating conditions on analytical performance," Biosensors & Bioelectronics, vol. 13, No. 3-4, pp. 371-382, (1998).

Vigil et al., "$TiO_2$ Layers Grown from Flowing Precursor Solutions Using Microwave Heating," Langmuir, vol. 17, pp. 891-896, (2001).

Viitala et al., "Surface properties of in vitro bioactive and non-bioactive sol-gel derived materials," Biomaterials, vol. 23, pp. 3073-3086, (2002).

Vitte et al., "Is there a predictable relationship between surface physical-chemical properties and cell behaviour at the interface?" European Cells and Materials, vol. 7, pp. 52-63, (2004).

Volkel et al., "Electrodeposition of coppeer and cobalt nanostructures using self-assembled monolayer templates," Surface Science, vol. 597, pp. 32-41, (2005).

Vu et al., "Eletrophoretic deposition of nanocomposites formed from polythiophene and metal oxides," Electrochimica Acta, vol. 51, pp. 1117-1124, (2005).

Vuković et al., "Anodic stability and electrochromism of electrodeposited ruthenium-iridium coatings on titanium," Journal of Electroanalytical Chemisty, vol. 330, pp. 663-673 (1992).

Walboomers et al., "Effect of microtextured surfaces on the performance of percutaneous devices," Journal of Biomedical Materials Research Part A, vol. 74A, No. 3, pp. 381-387, (2005).

Wang et al., "Deposition of in-plane textured MgO on amorphous $Si_3N_4$ substrates by ion-beam-assisted deposition and comparisons with ion-beam-assistend deposidted yttria-stabilized-zirconia," Applied Physics Letters, vol. 71, No. 17, Issue 20, pp. 2955-2957, Nov. 17, 1997.

Wang et al., "Effect of substrate temperature on structure and electrical resistivity of laser ablated $Ir_2$ thin films," Applied Surface Science, vol. 253, pp. 2911-2914, (2006).

Wang et al., "Effect of the discharge pulsating on microarc oxidation coating formed on Ti6A14V alloy," Materials Chemistry and Physics, vol. 90, pp. 128-133, (2005).

Wang et al., "Novel Poly(3-nonylthiophene)-$TiO_2$ Hybrid Materials for Photovoltaic Cells," Synthetic Metals, vol. 155, pp. 677-680, (2005).

Wang et al., "Polyelectrolyte-Coated Colloid Spheres as Templates for Sol-Gel Reactions," Chem. Mater., vol. 14, pp. 1909-1913, (2002).

Wang et al., "Pulsed laser deposition of organic thin films," This Solid Films, vol. 363, pp. 58-60, (2000).

Wang et al., "Synthesis of Macroporous Titania and Inorganic Composite Materials from Coated Colloidal Spheres—A Novel Route to Tune Pore Morphology," Chem. Mater., vol. 13, pp. 364-371, (2001).

Webster et al." Enhanced functions of osteoblasts on nanophase ceramics," Biomaterials, vol. 21, No. 17, pp. 1803-1810, Sep. 2000.

Webster et al., "Increased osteoblast adhesion on nanophase metals: Ti, Ti6A14V, and CoCrMo," Biomaterials, vol. 25, No. 19, pp. 4731-4739, (2004).

Webster et al., "Specific proteins mediate enhanced osteoblast adhesion on nanophase ceramics," Journal of Biomedical Materials Research, vol. 5, No. 51, pp. 475-483, Sep. 2000.

Wei et al., "Structural Characterisation of Doped and Undoped Nanocrystalline Zinc Oxides Deposited by Ultrasonic Spray Assisted Chemical Vapour Deposition," Journal of Physics: Conference Series, vol. 26, pp. 183-186 (2006).

Wells, "Patterned Plasma Immersion Exposure of Insulating Materials for the Purpose of Modifying Optical Properties," thesis submitted to the college of William and Mary, Williamsburg, Virginia, Apr. 2000.

Wesolowski et al., "Surface Charge and Ion Adsorption on Metal Oxides to 290°C," Division of Chemical Sciences, Geosciences, and Biosciences, Office of Basic Energy Sciences, U.S. Department of Energy, (2001).

Wessling et al., "RF-sputtering of iridium oxide to be used as stimulation material in functional medical implants," Journal of Micromechanics and Microengineering, vol. 16, pp. S142-S148 (2006).

Whelan, "Targeted Taxane Therapy for Cancer," Drug Discovery Today, vol. 7, No. 2, pp. 90-92, Jan. 2002.

Which stent is right for you? (circa 2004).

Wieneke et al., "Synergistic Effects of a Novel Nanoporous Stent Coating and Tacrolimus on Intima Proliferation in Rabbits," Catheterization and Cardiovascular Interventions, vol. 60, pp. 399-407, (2003).

Wilkinson et al., "Nanofabrication in cellular engineering," Journal of Vacuum Science & Technology B, vol. 16, No. 6, pp. 3132-3136, (1998).

Wilkinson et al., "The use of materials patterned on a nano- and micro-metric scale in cellular engineering," Materials Science & Engineering C, vol. 19, No. 1-2, pp. 263-269, (2002).

Wilson et al., "Mediation of biomaterial-cell interactions by adsorbed proteins: A review," Tissue Engineering, vol. 11, No. 1-2, pp. 1-18, (2005).

Wong et al., "Balance of chemistry, topography, and mechanics at the cell-biomaterial interface: Issues and challenges for assessing the role of substrate mechanics on cell response," Surface Science, vol. 570, No. 1-2, pp. 119-133, (2004).

Wong et al., "Polymer segmental alignment in polarized pulsed laser-induced periodic surface structures," Applied Physics A, vol. 65, pp. 519-523, (1997).

Wood, "Next-generation drug-eluting stents tackle shortcomings of Cypher, Taxus," Heart Wire, Feb. 7, 2006, (http://www.theheart.org/article/641591.do.).

World Reference definition, "Interconnected," WorldReference.com, [downloaded Jan. 21, 2010].

Wu et al., "Characterization of Mesoporous Nanocrystalline $TiO_2$ Photocatalysts Synthesized Via a Sol-Solvothermal Process at a Low Temperature," Journal of Solid State Chemistry, vol. 178, pp. 321-328, (2005).

Wu et al., "Chitosan-Mediated and Spatially Selective Electrodeposition of Nanoscale Particles," Langmuir, vol. 21, pp. 3641-3646, (2005).

Wu et al., "Corrosion resistance of $BaTiO_3$ films prepared by plasma electrolytic oxidation," Surface and Coatings Technology, vol. 166, pp. 31-36, (2002).

Wu et al., "Design of Doped Hybrid Xerogels for a Controlled Release of Brilliant Blue FCF," Journal of Non-Crystalline Solids, vol. 342, pp. 46-53, (2004).

Wu et al., "The effects of cathodic and anodic voltages on the characteristics of purous nanocrystalline titania coatings fabricated by microarc oxidation," Materials Letters, vol. 59, pp. 370-375, (2005).

Xia et al., "Monodispersed Colloidal Spheres: Old Materials with New Applications," Advanced Materials, vol. 12, No. 10, pp. 693-713, (2000).

Xu et al., "An Improved Method to Strip Aluminum from Porous Anodic Alumina Films," Langmuir, vol. 19, pp. 1443-1445, (2003).

Xu et al., "Cold spay deposition of thermoplastic powder," Surface & Coatings Technology, vol. 2001, pp. 3044-3050, (2006).

Xu et al., "Synthesis of porosity controlled ceramic membranes," Journal of Material Research, vol. 6, No. 5, pp. 1073-1081, May 1991.

Yamato et al. "Nanofabrication for micropatterned cell arrays by combining electron beam-irradiated polymer grafting and localized laser ablation," Journal of Biomedical Materials Research, vol. 67, No. 4, pp. 1065-1071, Dec. 15, 2003.

Yan et al., "New MOCVD precursor for iridium thin films deposition," Materials Letters, vol. 61, pp. 216-218, (2007).

Yan et al., "Sol-gel Processing," Handbook of Nanophase and Nanostructured Materials, vol. 1: Synthesis, Chapter 4, (2003).

Yang et al., "Laser spray cladding of porous NiTi coatings on NiTi substrates," The Hong Kong Polytechnic University, Dec. 28, 2006.

Yang et al., "Poly($_{L,L}$-lactide-co-glycolide)/tricalcium phosphate composite scaffold and its various changes during degradation in vitro," Polymer Degradation and Stability, vol. 91 pp. 3065-3073, (2006).

Yang et al., "Thermal oxidation products and kinetics of polyethylene composites," Polymer Degradation and Stability, vol. 91, pp. 1651-1657, (2006).

Yang et al., "Solution phase synthesis of magnesium hydroxide sulfate hydrate nanoribbons", Nanotechology, vol. 15, pp. 1625-1627, (2004).

Yankov et al., "Reactive plasma immersion ion implantation for surface passivation," Surface and Coatings Technology, vol. 201, pp. 6752-6758, (2007).

Yap et al., "Protein and cell micropatterning and its integration with micro/nanoparticles assembley," Biosensors and Bioelectronics, vol. 22, pp. 775-788, (2007).

Yerokhin et al., "Kinetic aspects of aluminium titanate layer formation on titanium alloys by plasma electrolytic oxidation," Applied Surface Science, vol. 200, pp. 172-184, (2002).

Yerokhin et al., "Plasma electrolysis for surface engineering," Surface Coatings Technology, vol. 122, pp. 73-93, (1999).

Yim et al., "Nanopattern-induced changes in morphology and motility of smooth muscle cells," Biomaterials, vol. 26, pp. 5405-5413, (2005).

Yim et al., "Significance of synthetic nanostructures in dictating cellular response," Nanomedicine: Nanotechnology, Biology and Medicine, vol. 1, No. 1, pp. 10-21, Mar. 1, 2005.

Yoldi et al., "Electrophoretic deposition of colloidal crystals assisted by hydrodynamic flows," Journal of Materials Science, vol. 41, pp. 2964-2969, (2006).

Yoshida et al., "Impact of Low Energy Helium Irradiation on Plasma Facing Metals," Journal of Nuclear Materials, vol. 337-339, pp. 946-950, (2005).

Young et al., "Polarized electrochemical vapor deposition for cermet anodes in solid oxide fuel cells," Solid State Ionics, vol. 135, pp. 457-462, (2000).

Yu et al., "Encapsulated cells: an atomic force microscopy study," Biomaterials, vol. 25, pp. 3655-3662, (2004).

Yu et al., "Enhanced photocatalytic activity of mesoporous and ordinary $TiO_2$ thin films by sulfuric acid treatment," Applied Catalysis B: Environmental, vol. 36, pp. 31, 43, (2002).

Yu et al., "Enhanced photoinduced super-hydrophilicity of the sol-gel-derived TiO2 thin films by Fe-doping," Materials Chemistry and Physics, vol. 95, pp. 193-196, (2006).

Yu et al., "Light-induced super-hydrophilicity and photocatalytic activity of mesoporous TiO2 thin films," Journal of Photochemistry and Photobiology A: Chemistry, vol. 148, pp. 331-339, (2002).

Yun et at., "Low-Temperature Coating of Sol-Gel Anatase Thin Films," Materials Letters, vol. 58, pp. 3703-3706, (2004).

Zakharian et al., "A Fullerene- Paclitaxel Chemotherapeutic: Synthesis, Characterization, and Study of Biological Activity in Tissue Culture," Journal of American Chemistry Society, vol. 127, pp. 12508-12509, (2005).

Zbroniec et al., "Laser ablation of iron oxide in various ambient gases," Applied Surface Science, vol. 197-198, pp. 883-886, (2002).

Zeng et al., "Biodegradable electrospun fibers for drug delivery," Journal of Controlled Release, vol. 92, pp. 227-231, (2003).

Zhang et al., "Surface analyses of micro-arc oxidized and hydrothermally treated titanium and effect on osteoblast behavior," Journal of Biomedical Materials Research, vol. 68A, pp. 383-391, (2004).

Zhang et al., "Surface treatment of magnesium hydroxide to improve its dispersion in organic phase by the ultrasonic technique", Applied Surface Science, vol. 253, pp. 7393-7397, (2007).

Zhao et al., "Coating deposition by the kinetic spray process," Surface & Coatings Technology, vol. 200, pp. 4746-4754, (2006).

Zhao et al., "Designing Nanostructions by Glancing Angle Deposition," Proceedings of SPIE, vol. 5219: Nanotubes and Nanowires, pp. 59-73, (2003).

Zhao et al., "Formulation of a ceramic ink for a wide-array drop-on-demand ink jet printer," Ceramics International, vol. 29, pp. 887-892, (2003).

Zheng et al., "Substrate temperature dependent morphology and resistivity of pulsed laser deposited iridium oxide thin films," Thin Solid Films, vol. 496, pp. 371-375, (2006).

Zheng et al., "Synthesis of Mesoporous Silica Materials via Nonsurfactant Templated Sol-Gel Route Using Mixture of Organic Compounds as Template," Journal of Sol-Gel Science and Technology, vol. 24. pp. 81-88, (2002).

Zhitomirsky et al., "Cathodic electrodeposition of MnOx films for electrochemical supercapacitors," Electrochimica Acta, vol. 51, pp. 3039-3045, (2006).

Zhitomirsky et al., "Electrodeposition of composite hydroxyapatite-chitosan films," Materials Chemistry and Physics, vol. 94, pp. 245-251, (2005).

Zhou et al., "Branched Ta nanocolumns grown by glancing angle deposition," Applied Physics Letters, vol. 88, p. 203117, (2006).

Zoppi et al., "Hybrid Films of Poly(ethylene oxide-b-amide 6) Containing Sol-Gel Silicon or Titanium Oxide as Inorganic Fillers: Effect of Morphology and Mechanical Properties on Gas Permeability," Polymer, vol. 41, pp. 5461-5470, (2000).

Zou et al., "Highly textural lamellar mesostructured magnesium hydroxide via a cathodic electrodeposition process", Materials Letters, vol. 61, pp. 1990-1993, (2007).

US 6,533,715, 03/2003, Hossainy et al. (withdrawn)

* cited by examiner

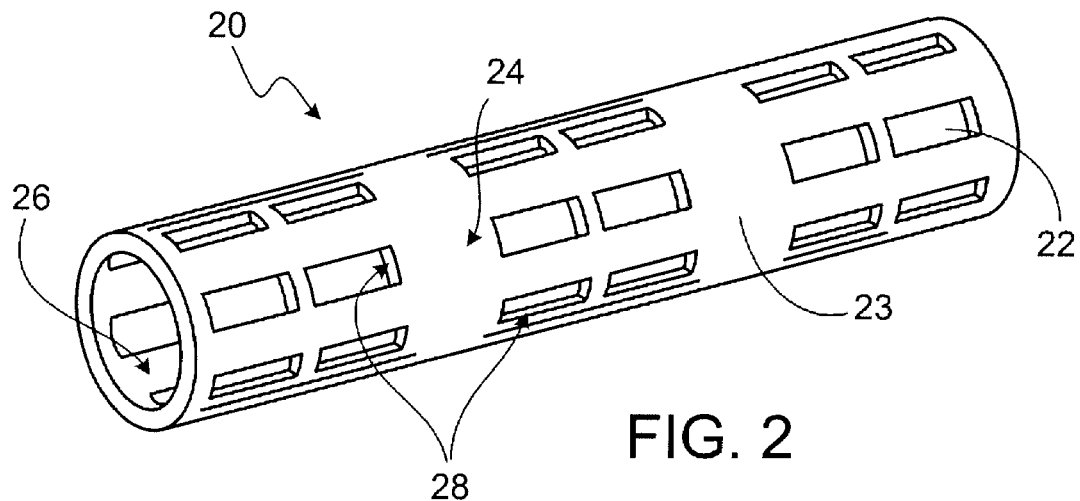
FIG. 2
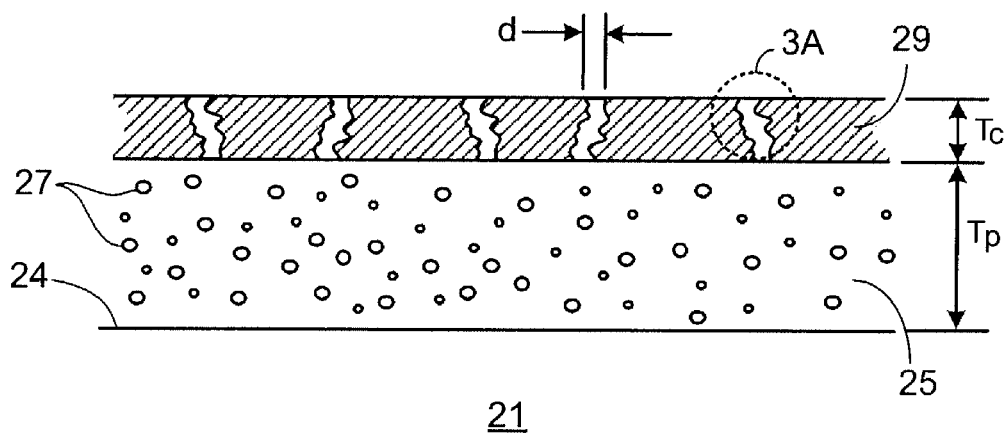
FIG. 3
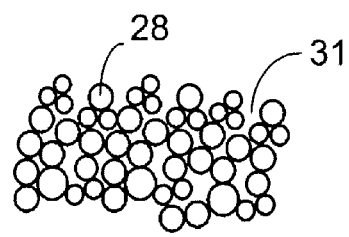
FIG. 3A

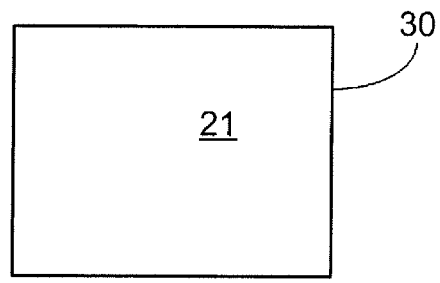
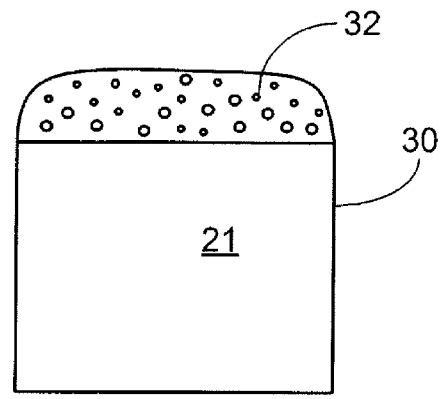
FIG. 4A                FIG. 4B
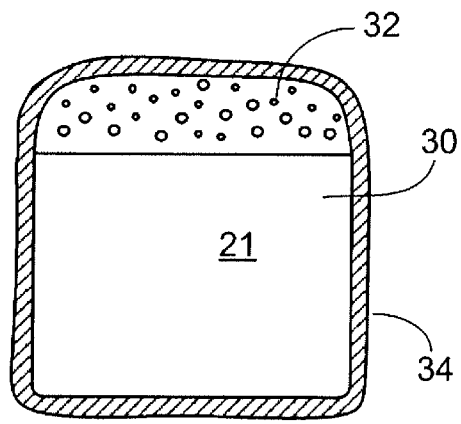
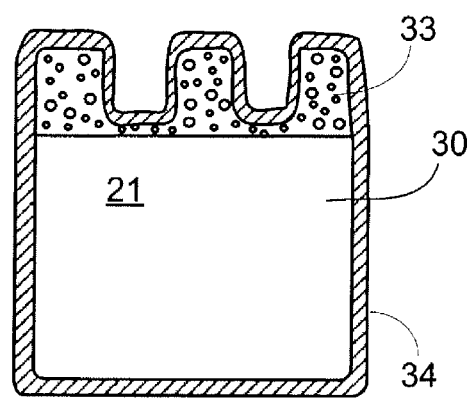
FIG. 4C                FIG. 5

ENDOPROSTHESIS WITH COATINGS

CROSS-REFERENCE TO RELATED APPLICATIONS

This application claims priority from U.S. Provisional Patent Application No. 60/857,849, filed Nov. 9, 2006, the entire contents of which is hereby incorporated by reference.

TECHNICAL FIELD

This invention relates to endoprostheses with coatings.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced with a medical endoprosthesis. An endoprosthesis is typically a tubular member that is placed in a lumen in the body. Examples of endoprostheses include stents, covered stents, and stent-grafts.

Endoprostheses can be delivered inside the body by a catheter that supports the endoprosthesis in a compacted or reduced-size form as the endoprosthesis is transported to a desired site. Upon reaching the site, the endoprosthesis is expanded, e.g., so that it can contact the walls of the lumen. Stent delivery is further discussed in Heath, U.S. Pat. No. 6,290,721, the entire contents of which is hereby incorporated by reference herein.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn from the lumen.

Passageways containing endoprostheses can become re-occluded. Re-occlusion of such passageways is known as restenosis. It has been observed that certain drugs can inhibit the onset of restenosis when the drug is contained in the endoprosthesis. It is sometimes desirable for an endoprosthesis-contained therapeutic agent, or drug to elute into the body fluid in a predetermined manner once the endoprosthesis is implanted.

SUMMARY

In an aspect, the document features an endoprosthesis having a first coating including a polymer, and a second coating over the first coating formed of a porous ceramic or metal.

In another aspect, the document features a method of forming an endoprosthesis, including forming a polymer coating that has a drug on the endoprosthesis, and forming a layer of porous ceramic or metal over the drug-containing polymer coating.

Embodiments may include one or more of the following features. The polymer can include a drug. The polymer can have a drug content of about 8.8% by weight or more (e.g., 15% or more, 25% or more). The polymer can be a non-biodegradable polymer such as styrene-isobutylene-styrene (SIBS) or polybutylene succinate (PBS). The first coating can have a plurality of depressions. The second coating can be formed of a porous ceramic. The second coating can have pores with a pore diameter of about 1 nm to 20 nm. The ceramic can be an oxide. The ceramic can be iridium oxide (IROX), titanium oxide (TIOX), tantalum oxide, or niobium oxide. The ceramic can have a smooth globular morphology to enhance endothelial cell growing over the ceramic. The ceramic can have a porosity of about 80% or less. The second coating can have a thickness less than the thickness of the first coating. The thickness of the second coating can be about 10 to 500 nm. The thickness of the first coating is about 0.1 to about 10 micron (e.g., about 0.5 to about 3 micron). The first coating can contact a surface of an endoprosthesis body. The endoprosthesis body can be formed of a metal. The metal is stainless steel. The endoprosthesis body can be formed of a polymer. The polymer can be a biostable polymer. The polymer can be a bioerodible polymer. The second coating can be formed of porous metal. The porous metal can be copper, gold, ruthenium, titanium, tantalum, platinum, palladium, stainless steel or an alloy thereof.

Embodiments may also include one or more of the following features. The polymer coating can be formed by spraying a solution of a polymer and a drug to a surface of an endoprosthesis body. The endoprosthesis body can be a metal. The metal can be stainless steel. The endoprosthesis body can be a polymer. The drug can be introduced by coating, dipping, or spraying in a solvent. The polymer coating can be formed by introducing a polymer to the endoprosthesis by dipping, spraying, brushing, pressing, laminating, or pulsed laser deposition (PLD). The drug can be introduced by PLD. The layer can be formed by PLD. The layer can be formed by magnetron sputtering. The layer can be a metal, such as copper, gold, silver, ruthenium, titanium, tantalum, platinum, palladium, stainless steel or an alloy thereof. The layer can be ceramic. The layer can be IROX. The ceramic can have a smooth globular morphology to enhance endothelial cell growing over the ceramic. The method can further include forming depressions in the polymer coating by laser irradiation.

Embodiments may include one or more of the following advantages. Stents can be formed with coatings of a ceramic or metal and a polymer that have morphologies and/or compositions that enhance therapeutic performance. In particular, the ceramic or metal can be deposited over the polymer coating to form a porous coating or membrane that controls drug release rate from the polymer as well as reduces the likelihood of direct contact of polymer to the body tissue. The over coating or membrane can be formed of a ceramic, e.g. IROX, which can have therapeutic advantages such as reducing the likelihood of restenosis and enhancing endothelialization. The morphology of the ceramic coating can be controlled to tune the therapeutic properties and the porosity of the membrane to provide a desired drug release profile over an extended period. The over coating or membrane may also reduce polymer flaking or delamination by further fixing it to one side, e.g., the abluminal side of an endoprosthesis body due to integrity of the over coating. The over coating can also facilitate deployment from a delivery device during deployment by reducing friction between the stent and delivery device. The membrane can be formed by low temperature deposition process, such as PLD or sputtering, which reduces the likelihood of degradation of the underlying polymer and/or a drug in the polymer coating. The polymer coating can be selected to accommodate a large quantity of drug and at the same time be relatively thin. Likewise, the membrane can be relatively thin, so as not to substantially increase the overall thickness of the stent wall.

Still further aspects, features, embodiments, and advantages follow.

DESCRIPTION OF DRAWINGS

FIG. 2 is a perspective view of a stent.

FIG. 3 is a cross-sectional view of region of a stent wall while FIG. 3A is a greatly enlarged view of region 3A of FIG. 3.

FIGS. 4A-4C are cross-sectional views illustrating a method for forming a stent.

FIG. 5 is a cross-sectional view of another embodiment.

FIGS. 7A and 7B are enlarged plan views of a stent wall surface, FIG. 7C is an enlarged cross-sectional view of a stent wall surface.

DETAILED DESCRIPTION

Figure 1:
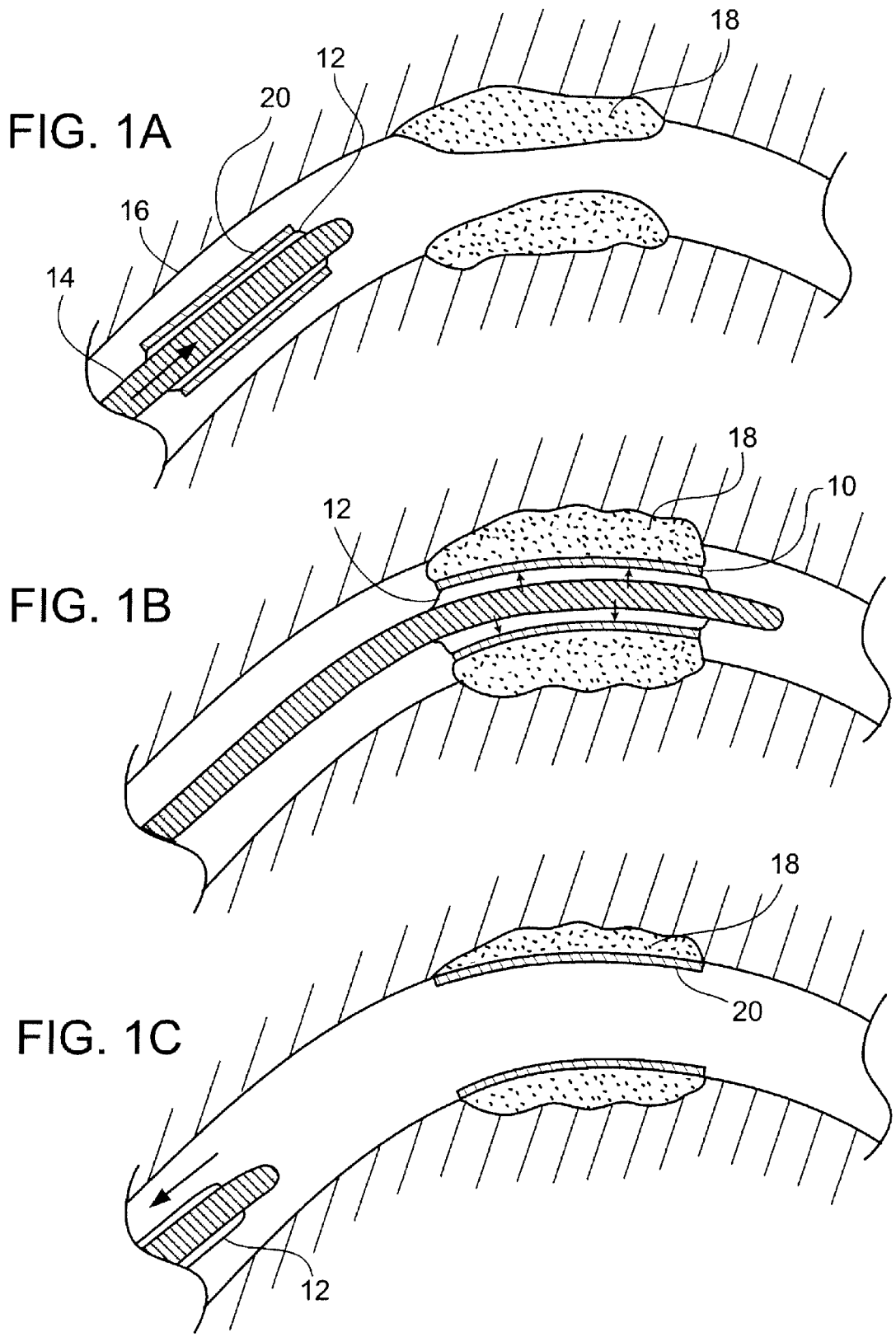
FIGS. 1A-1C are longitudinal cross-sectional views illustrating delivery of a stent in a collapsed state, expansion of the stent, and deployment of the stent.

Referring to FIGS. 1A-1C, a stent 20 is placed over a balloon 12 carried near a distal end of a catheter 14, and is directed through the lumen 16 (FIG. 1A) until the portion carrying the balloon and stent reaches the region of an occlusion 18. The stent 20 is then radially expanded by inflating the balloon 12 and compressed against the vessel wall with the result that occlusion 18 is compressed, and the vessel wall surrounding it undergoes a radial expansion (FIG. 1B). The pressure is then released from the balloon and the catheter is withdrawn from the vessel (FIG. 1C).

Referring to FIG. 2, the stent 20 includes a plurality of fenestrations 22 defined in a wall 23. Stent 20 includes several surface regions, including an outer, or abluminal, surface 24, an inner, adluminal, surface 26, and a plurality of cut-face surfaces 28. The stent can be balloon expandable, as illustrated above, or a self-expanding stent. Examples of stents are described in Heath '721, supra.

Referring to FIG. 3, a cross-sectional view, a stent wall 23 includes a stent body 21 formed, e.g. of a metal, and includes a first coating 25, such as a polymer that includes a drug 27 (e.g. a drug eluting polymer, "DEP"), on the abluminal side 24, and a second coating, such as a porous ceramic or metal coating 29 on both the first coating 25 and the adluminal side 26. An interface region (not shown) formed, e.g., of a mixture of the polymer and the ceramic or metal may exist between the two coatings. The polymer will have substantially no direct contact with body tissue once the stent is implanted, thus allowing the use of a broader range of polymers, optimized, for example, for drug eluting properties with less concern for biocompatibility, tissue irritation, tendency to adhere to deployment devices.

Referring to FIG. 3A, the ceramic is deposited as small clusters 28, e.g., 100 nm or less, such as 1-10 nm, and preferably smaller than the gross morphological features of the coating. In embodiments, the clusters amalgamate or bond at contact points forming an almost continuous coating with open-cell porous structures or interconnected pores 31 that serve as passageways between the interior and the exterior of the ceramic coating. The thickness, the average pore size, and/or the pore to total (solid and pores) volume ratio (e.g., porosity) of the ceramic coating 29 can be selected to control drug release profile over time by, e.g., controlling the diffusion rate of the drug to the surrounding environment and/or controlling the diffusion rate of body fluid to the DEP, when the stent is implanted. In embodiments, the coating can have a thickness Tc of about a few nanometers ("nm") to a few hundred nanometers, e.g., of about 10 nm to 500 nm, or about 10-350 nm, or about 10-20 nm. In embodiments, the pore size d is selected to be about 1-20 nm in pore diameter. In embodiments, the porosity is selected to be about 10% to 40%.

In embodiments, the polymer coating 25 can be a drug eluting polymer ("DEP"), e.g., a biodegradable or non-biodegradable DEP. The coating 25 has a thickness Tp of about 100 nm to about 50 μm, e.g., about 200 nm to about 10 μm, or about 300 nm to about 2 μm, which is selected to control the total amount of the releasable drug once the stent is implanted. In embodiments, the drug content in the DEP is selected to be about 5 to about 50 weight percent (wt. %), e.g. about 8.8 to about 25 wt. %. In embodiments, compared to a DEP without coating 29, the polymer can be provided with higher loadings of drug since the ceramic coating 29 modulates the delivery of drug to the body.

In embodiments, the porous coating 29 is formed of a ceramic, such as iridium oxide ("IROX"). Certain ceramics, e.g. oxides, can reduce restenosis through the catalytic reduction of hydrogen peroxide and other precursors to smooth muscle cell proliferation. The oxides can also encourage endothelial growth to enhance endothelialization of the stent. When a stent is introduced into a biological environment (e.g., in vivo), one of the initial responses of the human body to the implantation of a stent, particularly into the blood vessels, is the activation of leukocytes, white blood cells which are one of the constituent elements of the circulating blood system. This activation causes an increase of reactive oxygen compound production. One of the species released in this process is hydrogen peroxide, $H_2O_2$, which is released by neutrophil granulocytes, which constitute one of the many types of leukocytes. The presence of $H_2O_2$ may increase proliferation of smooth muscle cells and compromise endothelial cell function, stimulating the expression of surface binding proteins which enhance the attachment of more inflammatory cells. A ceramic, such as IROX can catalytically reduce $H_2O_2$. The morphology of the ceramic can enhance the catalytic effect and reduce proliferation of smooth muscle cells. In a particular embodiment, IROX is selected to form the coating 29, which can have therapeutic benefits such as enhancing endothelialization. IROX and other ceramics are discussed further in Alt et al., U.S. Pat. No. 5,980,566 and U.S. Ser. No. 10/651,562 filed Aug. 29, 2003.

Referring to FIGS. 4A-4C, cross-section views of a stent strut illustrate exemplary procedures of forming a stent. Referring particularly to FIGS. 4A and 4B, the stent strut 30 includes a body 21 over which is formed a coating 32 of polymer on a selected side of the strut, such as the abluminal side. Polymeric coating 32 is formed by, e.g., rolling, dipping, spraying, pulsed laser deposition ("PLD"), pressing, brushing, or laminating. In embodiments, the polymer can contain a drug or a therapeutic agent (circles). The drug may be co-applied to the stent with the polymer by the above-mentioned techniques or be loaded into the polymeric coating by, e.g., absorption by the polymer, after the polymer coating is formed on the stent strut. For example, a DEP coating can be formed by spraying the stent with a polymer or a drug saturated solvent which also contains the polymer and drying under low temperature, e.g. ambient conditions. The DEP coating can also be formed by PLD using a drug target and a polymer target. In other embodiments, the coating 32 may be a polymer precursor, or a mixture of a polymer precursor and a drug.

Referring particularly to FIG. 4C, a ceramic coating 34 is deposited conformally over the coating 32 and other surfaces of the strut, such as the adluminal and cut-face surfaces. The ceramic coating may be applied by physical deposition processes, such as sputtering or pulsed laser deposition ("PLD"), or by chemical methods such as sol-gel reactions.

An advantage of having coating 34 surrounding the stent strut as illustrated in FIG. 4C is that the polymer is further fixed or bound to the abluminal side of the stent due to integrity of the coating 34. As a result, polymer delamination due to, e.g., sheer force during the stent insertion in a body passageway, or body liquid seeping to the polymer-stent interface during or after the insertion, may be diminished. In embodiments, the surface topography of the polymer coating or the ceramic-polymer interface structure is selected to modify drug release profile. In other embodiments, the stent body is first coated with a conformal ceramic coating having, e.g. a high roughness defined grain morphology, a polymer coating, including drug is applied to the high roughness coating on a select portion, e.g. the adluminal portion, and a porous ceramic coating is then applied over the polymer.

Referring particularly to FIG. 5, in embodiments, a series of depressions, e.g., wells, in the polymeric coating 33 are created using, e.g., laser ablation or lithography, before depositing a substantially conformal ceramic coating over the polymer. In this embodiment, larger surface areas of the polymer are contacted by the ceramic over coating and thus possible increase of initial drug release rate can be achieved. In an alternative embodiment, the ceramic over coating is not conformal, for example, the ceramic is applied to the polymer in a manner such that at least one side of the polymer depression, e.g., the side wall, is not covered by the ceramic, allowing the drug to come out via the polymer without being obstructed by the ceramic layer. In such case, a non-porous ceramic over coating can be used instead of the porous ceramic material. This partial over coating can be achieved by, e.g., pulsed-laser depositing the ceramic under an angle such that one side of the depressions is not exposed to the ablated ceramic since PLD is a directional process. It can also be achieved by first depositing the ceramic over a flat polymer layer on a stent surface after which depressions can be formed using e.g., a excimer or ultrashort laser to selectively remove both the ceramic and the polymer in some regions.

Figure 6:
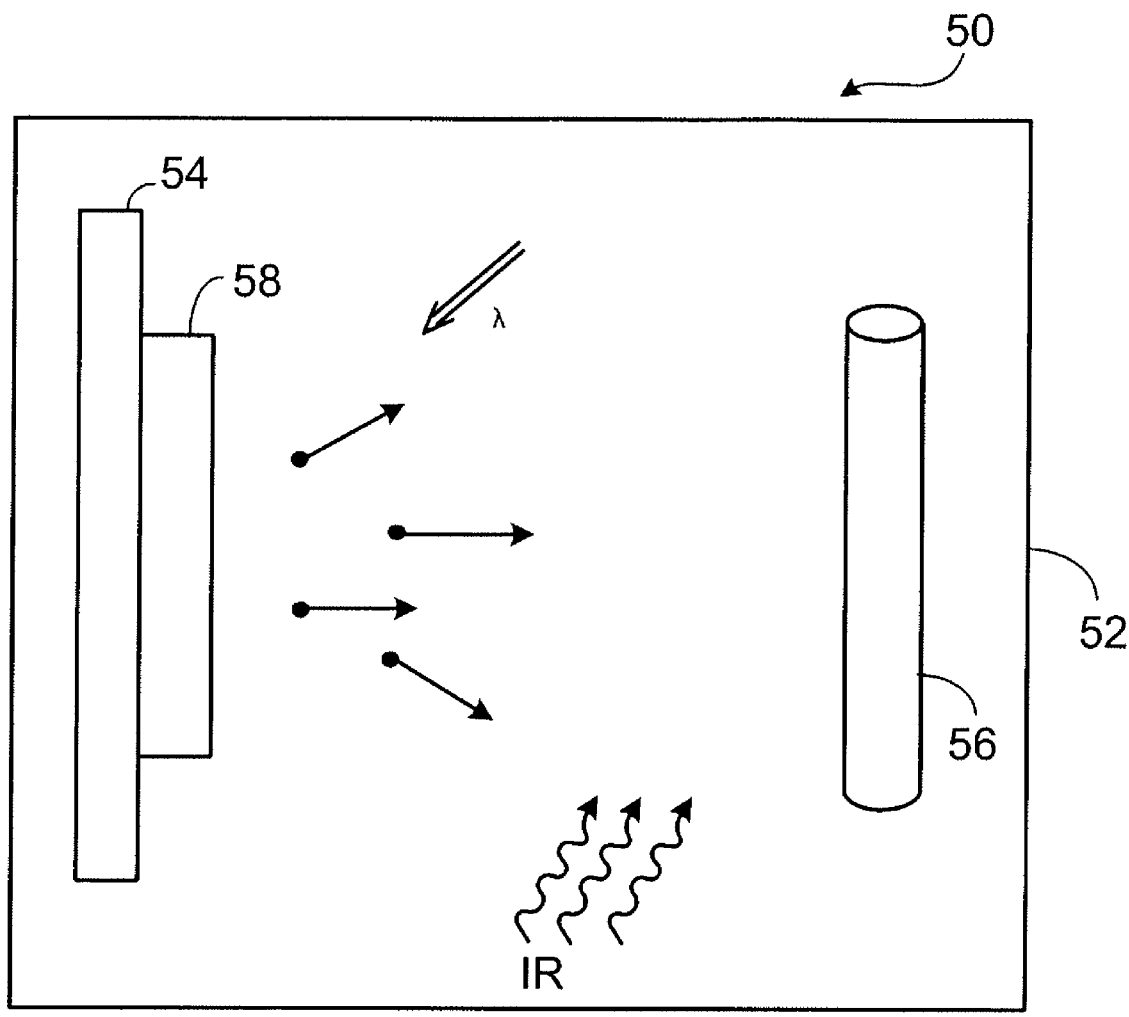
FIG. 6 is a schematic cross-sectional view of a PLD system.

In embodiments, the ceramic is provided over the polymeric coating by a technique that uses low temperature to reduce the likelihood of damaging the drug and/or the polymer, such as PLD. Referring to FIG. 6, a PLD system 50 includes a chamber 52 in which is provided a target assembly 54 and a stent substrate 56, such as a stent body or a pre-stent structure such as a metal tube. The target assembly includes a target material 58, such as a ceramic (e.g., IROX) or a precursor to a ceramic (e.g., iridium metal). Laser energy (double arrows) is selectively directed onto the target materials to cause the target materials to be ablated and sputtered from the target assembly. The sputtered material is imparted with kinetic energy in the ablation process such that the material is transported within the chamber (single arrows) and deposited on the stent 56. The target assembly may include more than one target (e.g., two targets) so that different materials, e.g., drugs, ceramics or mixtures of a ceramic and a polymer or of a polymer and a drug, can be deposited simultaneously or sequentially on the stent 56 for controlling drug release profiles. In addition, the temperature of the deposited material can be controlled by heating, e.g. using an infrared source (squiggly arrows).

The porosity of the ceramic can be controlled by selecting the morphology, crystallinity, thickness, and size of the clusters ablated and deposited. Higher crystallinity, more defined grain morphologies, and thinner coatings provide greater porosity. Coating thickness is controlled by controlling deposition time. Higher laser energies can provide larger cluster sizes.

In certain embodiments, if more than one targets, e.g., a polymer target and a ceramic target are needed for deposition, the composition of the deposited material is selected by controlling the exposure of the target materials to laser energy. For example, to deposit pure polymer or pure ceramic, only the polymer or ceramic material is exposed to laser energy. To deposit a composite layer of ceramic and polymer, both materials are exposed simultaneously or alternately exposed in rapid succession. The relative amount of polymer and ceramic is controlled by the laser energy and/or exposure time. In embodiments, the ceramic or polymer is deposited as small clusters, e.g., 100 nm or less, such as 1-10 nm, and preferably smaller than the gross morphological features of the layers. In embodiments, the clusters bond at contact points forming a continuous coating that is an amalgamation of the clusters. The molecular weight of the polymer can be controlled by selecting the laser wavelength and energy. In the ablation process, energy absorbed by the target can result in cleavage of covalent bonds in polymers, such that the chain lengths and molecular weight of the polymer in the target is reduced in the deposition material. The efficiency of the cleavage process can be enhanced by selecting a laser wavelength that the polymer absorbs strongly. In addition, at higher energies, the size of ablated clusters is increased, with less overall chain cleavage.

In particular embodiments, the laser energy is produced by an excimer laser operating in the ultraviolet, e.g. at a wavelength of about 248 nm. The laser energy is about 100-700 mJ, the fluence is in the range of about 10 to 50 mJ/cm2. The background pressure is in the range of about 1E-5 mbar to 1 mbar. The background gas includes oxygen. The substrate temperature is also controlled. The temperature of the substrate is between 0 to 150° C. during deposition. Substrate temperature can be controlled by directing an infrared beam onto the substrate during deposition using, e.g. a halogen source. The temperature is measured by mounting a heat sensor in the beam adjacent the substrate. The temperature can be varied to control the morphology of the ceramic and melting of the polymer. The selective sputtering of the ceramic or polymer is controlled by mounting the target material on a moving assembly that can alternately bring the materials into the path of the laser. Alternatively, a beam splitter and shutter can be used to alternatively or simultaneously expose multiple materials. PLD deposition services are available from Axyntec, Augsburg, Germany. Suitable ceramics include metal oxides and nitrides, such as of iridium, zirconium, titanium, hafnium, niobium, tantalum, ruthenium, platinum and aluminum. In embodiments, the thickness of the coatings is in the range of about 10 m to about 2 um, e.g. 100 nm to 500 nm. Pulsed laser deposition is also described in application U.S. Ser. No. 11/752,736, filed May 23, 2007 . The target can be a pure metal, e.g. IR target or iridium oxide in the form of compressed powder. The polymer, e.g. including drug, can also be deposited by PLA. In embodiments, the polymer is SIBS and the drug is paclitaxal at e.g. 8.8%. The laser power is 100 to 250 mn and the pressure between about 0.04 mbar and 0.2 mbar.

In other embodiments, another physical vapor deposition ("PVD") process is selected such as magnetron sputtering e.g. an iridium target under an oxygen atmosphere or an IROX target. Sputtering deposition is described in application U.S. Ser. No. 11/752,772, filed May 23, 2007 . In the case of a ceramic or a metal over coating, the porosity can be further controlled by laser ablating apertures into the layer with, e.g. a U.V. laser.

Figures 7A, 7B:
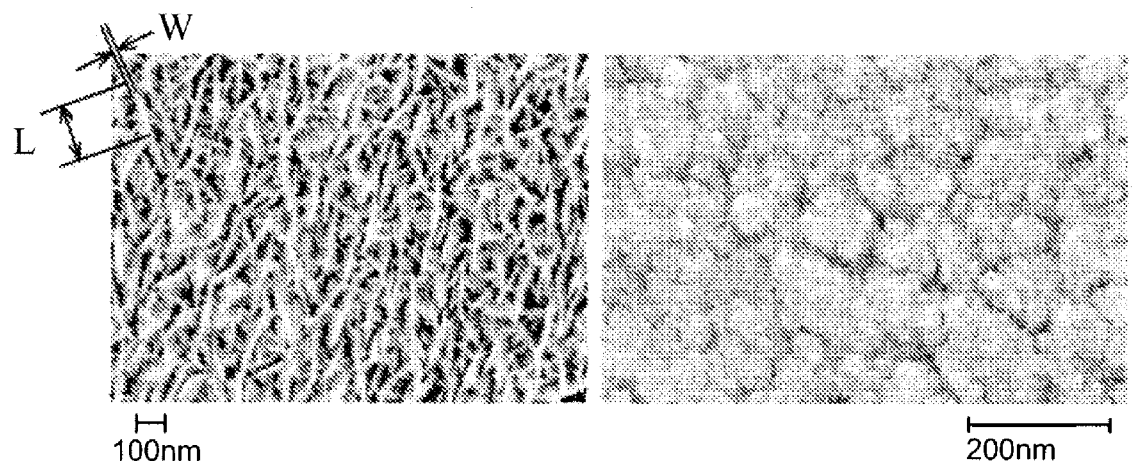
FIGS. 7A-7C are FESEM images.

Referring to FIGS. 7A and 7B, the morphology of the ceramic can be varied between relatively rough surfaces and relatively smooth surfaces, which can each provide particular mechanical and therapeutic advantages, such as a controlled porosity to modulate drug release from the polymer layer. Referring particularly to FIG. 7A, a ceramic coating can have a morphology characterized by defined grains and high roughness. Referring particularly to FIG. 7B, a ceramic coating can have a morphology characterized by a higher coverage, globular surface of generally lower roughness. The defined grain, high roughness morphology provides a high surface area characterized by crevices between and around spaced grains into which the polymer coating can be deposited and interlock to the surface, greatly enhancing adhesion. Defined grain morphologies also allow for greater freedom of motion and are less likely to fracture as the stent is flexed in use and thus the matrix coating resists delamination of the ceramic from an underlying surface and reduces delamination of a possible overlaying coating. The stresses caused by flexure of the stent, during expansion or contraction of the stent or as the stent is delivered through a tortuously curved body lumen increase as a function of the distance from the stent axis. As a result, in embodiments, a morphology with defined grains is particularly desirable on abluminal regions of the stent or at other high stress points, such as the regions adjacent fenestrations which undergo greater flexure during expansion or contraction. Smoother globular surface morphology provides a surface which is tuned to facilitate endothelial growth by selection of its chemical composition and/or morphological features. Certain ceramics, e.g. oxides, can reduce restenosis through the catalytic reduction of hydrogen peroxide and other precursors to smooth muscle cell proliferation. The oxides can also encourage endothelial cell growth to enhance endothelialization of the stent. As discussed above, when a stent, is introduced into a biological environment (e.g., in vivo), one of the initial responses of the human body to the implantation of a stent, particularly into the blood vessels, is the activation of white blood cells. This activation causes a release of hydrogen peroxide, $H_2O_2$. The presence of $H_2O_2$ may increase proliferation of smooth muscle cells and compromise endothelial cell function, stimulating the expression of surface binding proteins which enhance the attachment of more inflammatory cells. A ceramic, such as IROX can catalytically reduce $H_2O_2$. The smoother globular surface morphology of the ceramic can enhance the catalytic effect and enhance growth of endothelial cells.

Figure 7C:
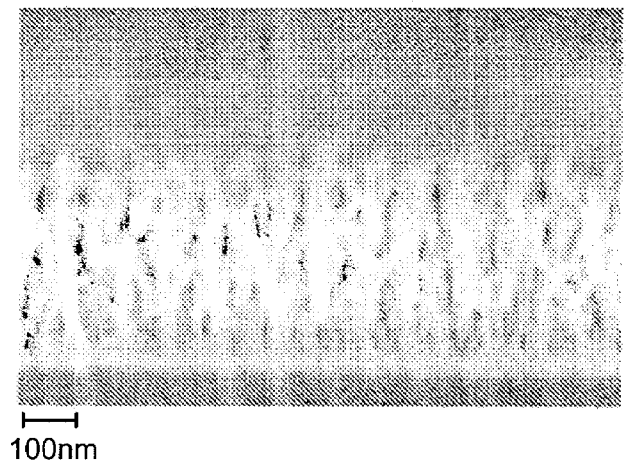

Referring particularly to FIG. 7C, a cross-sectional view of the ceramic layer with surface morphology shown in FIG. 7B, channels formed of interconnected pores in the ceramic are visible. In embodiments, the channels have a diameter selectively controlled by deposition parameters as discussed above. The bigger the diameter, the faster the drug release rate. In particular embodiments, the channel diameter is selected to be about 10 nm or less to control the drug release over a extended period of time.

The morphology of the ceramic is controlled by controlling the energy of the sputtered clusters on the stent substrate. Higher energies and higher temperatures result in defined grain, higher roughness surfaces. Higher energies are provided by increasing the temperature of the ceramic on the substrate, e.g. by heating the substrate or heating the ceramic with infrared radiation. In embodiments, defined grain morphologies are formed at temperatures of about 250° C. or greater. Globular morphologies are formed at lower temperatures, e.g. ambient temperatures without external factors. The heating enhances the formation of a more crystalline ceramic, which forms the grains. Intermediate morphologies are formed at intermediate values of these parameters. The composition of the ceramic can also be varied. For example, oxygen content can be increased by providing oxygen gas in the chamber.

The morphology of the surface of the ceramic is characterized by its visual appearance, its roughness, and/or the size and arrangement of particular morphological features such as local maxima. In embodiments, the surface is characterized by definable sub-micron sized grains. Referring particularly to FIG. 7A, for example, in embodiments, the grains have a length, L, of the of about 50 to 500 nm, e.g. about 100-300 nm, and a width, W, of about 5 nm to 50 nm, e.g. about 10-15 nm. The grains have an aspect ratio (length to width) of about 5:1 or more, e.g. 10:1 to 20:1. The grains overlap in one or more layers. The separation between grains can be about 1-50 nm. In particular embodiments, the grains resemble rice grains.

Referring particularly to FIG. 7B, in embodiments, the surface is characterized by a more continuous surface having a series of shallow globular features. The globular features are closely adjacent with a narrow minima between features. In embodiments, the surface resembles an orange peel. The diameter of the globular features is about 100 nm or less, and the depth of the minima, or the height of the maxima of the globular function is e.g. about 50 nm or less, e.g. about 20 nm or less. In other embodiments, the surface has characteristics between high aspect ratio definable grains and the more continuous globular surface and/or has a combination of these characteristics. For example, the morphology can include a substantially globular base layer and a relatively low density of defined grains. In other embodiments, the surface can include low aspect ratio, thin planar flakes. The morphology type is visible in FESEM images at 50 KX.

Figure 8A:
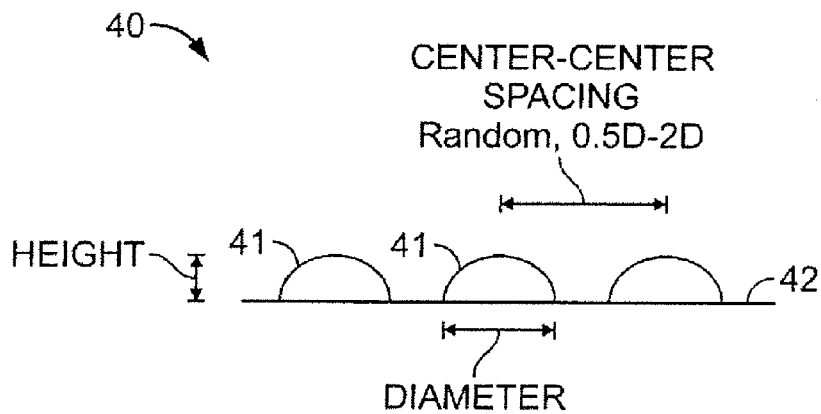
FIGS. 8A-8C are schematic views of ceramic morphologies.
Figure 8B:
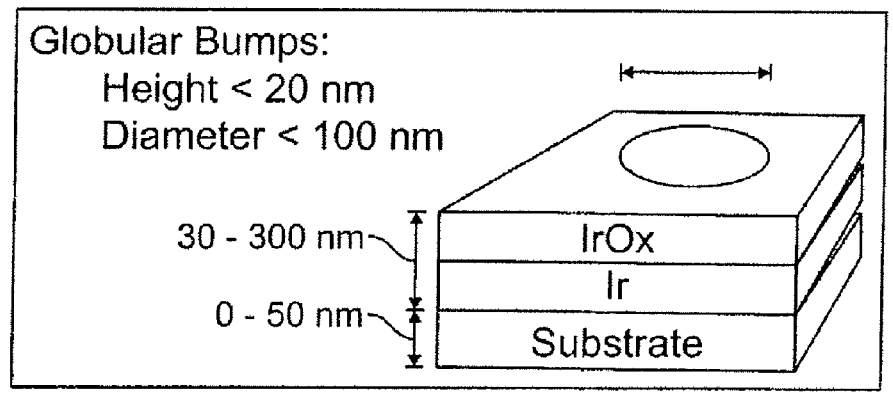
Figure 8C:
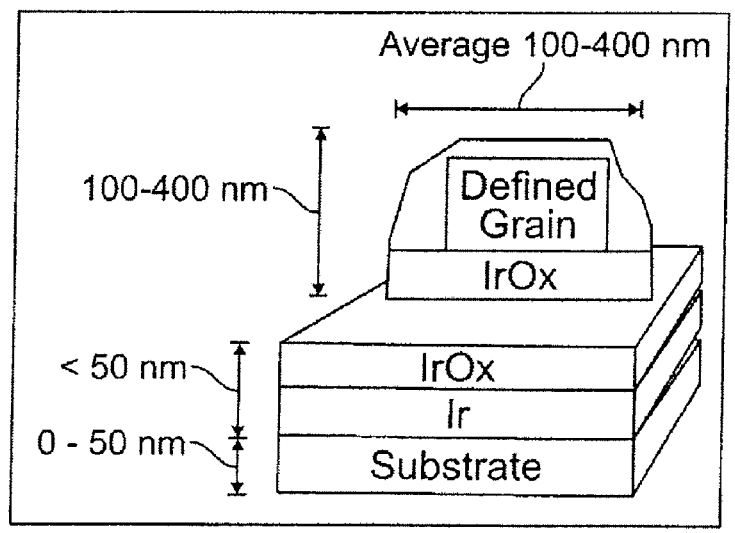

Referring to FIGS. 8A-8C, morphologies are also characterized by the size and arrangement of morphological features such as the spacing, height and width of local morphological maxima. Referring particularly to FIG. 5A, a coating 40 on a substrate 42 is characterized by the center-to-center distance and/or height, and/or diameter and/or density of local maxima. In particular embodiments, the average height, distance and diameter are in the range of about 400 nm or less, e.g. about 20-200 nm. In particular, the average center-to-center distance is about 0.5 to 2× the diameter.

Referring to FIG. 8B, in particular embodiments, the morphology type is a globular morphology, the width of local maxima is in the range of about 100 nm or less and the peak height is about 20 nm or less. In particular embodiments, the ceramic has a peak height of less than about 5 nm, e.g., about 1-5 nm, and/or a peak distance less than about 15 m, e.g., about 10-15 nm. Referring to FIG. 8C, in embodiments, the morphology is defined as a grain type morphology. The width of local maxima is about 400 nm or less, e.g. about 100-400 nm, and the height of local maxima is about 400 nm or less, e.g. about 100-400 nm. As illustrated in FIGS. 8B and 8C, the select morphologies of the ceramic can be formed on a thin layer of substantially uniform, generally amorphous IROX, which is in turn formed on a layer of iridium metal, which is in turn deposited on a metal substrate, such as titanium or stainless steel. The spacing, height and width parameters can be calculated from AFM data.

The roughness of the surface is characterized by the average roughness, Sa, the root mean square roughness, Sq, and/or the developed interfacial area ratio, Sdr. The Sa and Sq parameters represent an overall measure of the texture of the surface. Sa and Sq are relatively insensitive in differentiating peaks, valleys and the spacing of the various texture features. Surfaces with different visual morphologies can have similar Sa and Sq values. For a surface type, the Sa and Sq parameters indicate significant deviations in the texture characteristics. Sdr is expressed as the percentage of additional surface area contributed by the texture as compared to an ideal plane the size of the measurement region. Sdr further differentiates surfaces of similar amplitudes and average roughness. Typically Sdr will increase with the spatial intricacy of the texture whether or not Sa changes.

In embodiments, the ceramic has a defined grain type morphology. The Sdr is about 30 or more, e.g. about 40 to 60. In addition or in the alternative, the morphology has an Sq of about 15 or more, e.g. about 20 to 30. In embodiments, the Sdr is about 100 or more and the Sq is about 15 or more. In other embodiments, the ceramic has a globular type surface morphology. The Sdr is about 20 or less, e.g. about 8 to 15. The Sq is about 15 or less, e.g. about less than 8 to 14. In still other embodiments, the ceramic has a morphology between the defined grain and the globular surface, and Sdr and Sq values between the ranges above, e.g. an Sdr of about 1 to 200 and/or an Sq of about 1 to 30. The Sa, Sq, and Sdr can be calculated from AFM data.

The morphology of the ceramic coating can exhibit high uniformity. The uniformity provides predictable, tuned therapeutic and mechanical performance of the ceramic. The uniformity of the morphology as characterized by Sa, Sq or Sdr and/or average peak spacing parameters can be within about +/−20% or less, e.g. +/−10% or less within a tam square. In a given stent region, the uniformity is within about +/−10%, e.g. about +/−1%. For example, in embodiments, the ceramic exhibits high uniformity over an entire surface region of stent, such as the entire abluminal or adluminal surface, or a portion of a surface region, such as the center 25% or 50% of the surface region. The uniformity is expressed as standard deviation. Uniformity in a region of a stent can be determined by determining the average in five randomly chosen 1 μm square regions and calculating the standard deviation. Uniformity of a morphology type in a region is determined by inspection of FESEM data at 50 kx.

The ceramics are also characterized by surface composition, composition as a function of depth, and crystallinity. In particular, the amounts of oxygen or nitride in the ceramic is selected for a desired catalytic effect on, e.g., the reduction of $H_2O_2$ in biological processes. The composition of metal oxide or nitride ceramics can be determined as a ratio of the oxide or nitride to the base metal. In particular embodiments, the ratio is about 2 to 1 or greater, e.g. about 3 to 1 or greater, indicating high oxygen content of the surface. In other embodiments, the ratio is about 1 to 1 or less, e.g. about 1 to 2 or less, indicating a relatively low oxygen composition. In particular embodiments, low oxygen content globular morphologies are formed to enhance endothelialization. In other embodiments, high oxygen content defined grain morphologies are formed, e.g., to enhance adhesion and catalytic reduction. Composition can be determined by x-ray photoelectron spectroscopy (XPS). Depth studies are conducted by XPS after FAB sputtering. The crystalline nature of the ceramic can be characterized by crystal shapes as viewed in FESEM images, or Miller indices as determined by x-ray diction. In embodiments, defined grain morphologies have a Miller index of <101>. Globular materials have blended amorphous and crystalline phases that vary with oxygen content. Higher oxygen content typically indicates greater crystallinity. Further discussion of ceramics and ceramic morphology and computation of roughness parameters is provided in U.S. Ser. No. 11/752,736, filed May 23, 2007, U.S. Ser. No. 11/752,772, filed May 23, 2007, and appendices.

Figure 9:
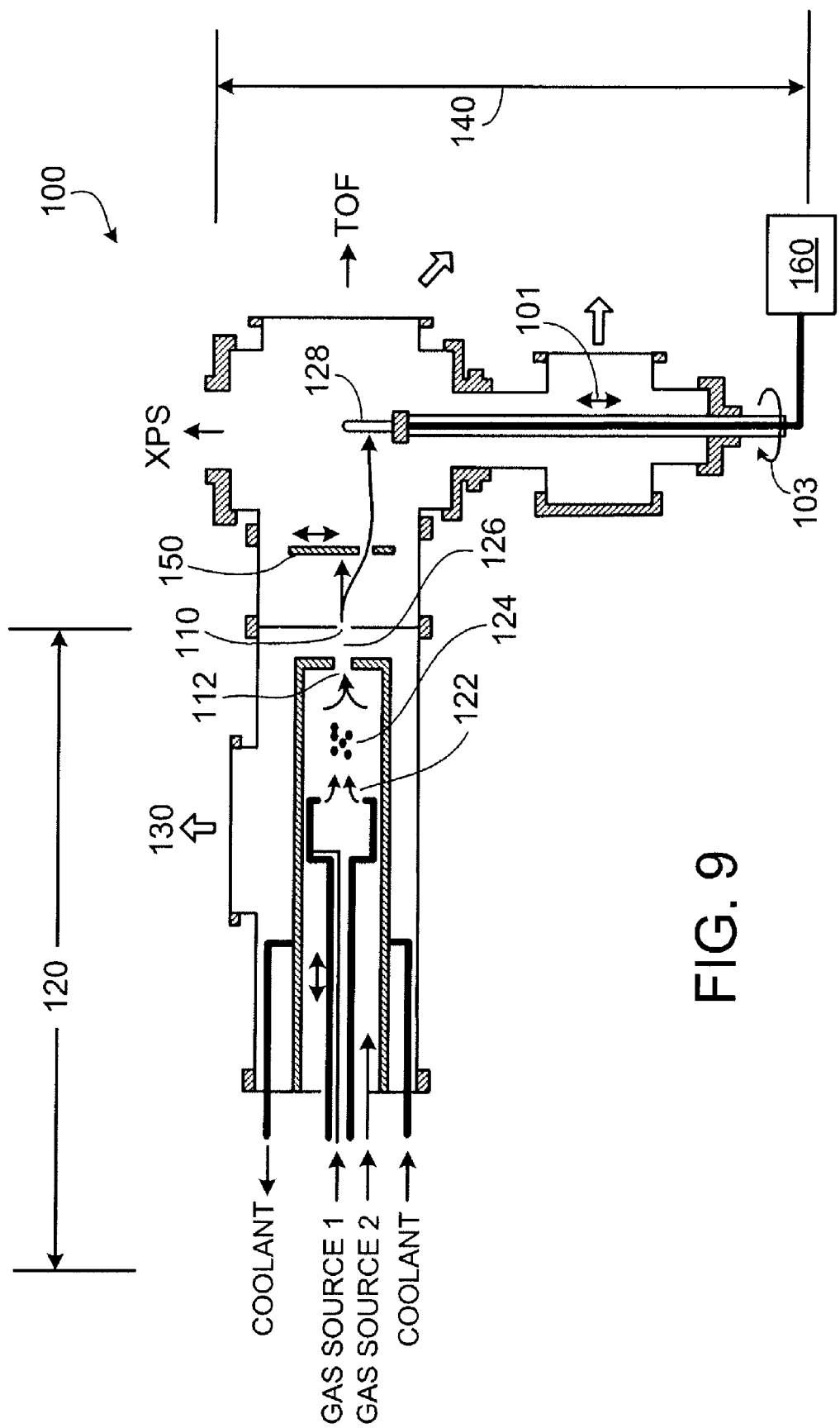
FIG. 9 is a schematic top view of a deposition system.

In certain embodiments, referring back to FIG. 3, the second coating 29 can be a porous metallic coating, formed for example, by using a nanocluster deposition system ("NCDS"). Referring particularly to FIG. 9, an NCDS 100 includes several differentially pumped chambers: a cluster source chamber 120 and a deposition chamber 140. The system may also have a load lock for rapid substrate change; a time of flight mass spectrometer (TOF) chamber (not shown) for analysis of the cluster size distribution; and/or an XPS system for elemental analysis with a separate transfer chamber (not shown). In the cluster source chamber, nanoparticles or clusters, such as copper, gold, ruthenium, stainless steel, iron, magnesium, and tungsten can be produced by high-pressure magnetron sputtering, for example, operating a magnetron head 122 in a pressure of about 0.1 to a few millibars with a flow of a working gas, e.g., argon provided by "Gas Source 1" shown in the figure. The relative high pressure allows the sputtered atoms or small clusters to aggregate or condensate in an aggregation zone 124 to form nanoparticles or clusters of desired size before they are transported to the deposition chamber. The clusters are carried by the flowing gas through an aperture 112, whose diameter can be varied during operation of the cluster source. After aperture 112, the clusters enter a differential pumping zone 126, where most of the carrier gas, atoms and/or lighter clusters are pumped away through vacuum port 130, while the heavier clusters pass through a further aperture 110 into the deposition chamber. Clusters are then electrically separated by ion optics 150 into a neutral (n) and a charged (c) beam. The charged clusters of one polarity can be accelerated up to about 50 keV and impinge on the substrate holder 128, which is connected to a voltage source 160 and can be moved horizontally (double-head arrow 101) and rotated (arrow 103) by a small motor (not shown). The charged clusters or nanoparticles generated may further be mass selected by a linear quadrupole (not shown) and selectively deposited on the substrate. For example, typical diameter of the clusters generated can be about 0.7 to 20 nm and size distribution of the clusters can be selectively narrowed to about +/−20%, or even to +/−2%.

The kinetic energy (e.g., about 100 V to 50 keV) of the clusters partly controlled by the applied voltage on the substrate holder may induce clusters melting upon impact the substrate and may cause damage to the polymeric substrate due to local heating. In embodiments, a first collection of clusters are deposited with a kinetic energy, e.g., 0.1 keV, that is high enough for the clusters to adhere to or penetrate the polymer substrate but substantially causes no heat damage to the polymer and/or the drug incorporated in the polymer. A second collection of clusters with higher kinetic energy, e.g., 5 keV, can then be deposited on top of the first collection. In embodiments, the magnetron head can be moved within the aggregation zone. Reducing the distance from the magnetron head to the first aperture reduces the distance and time whereby condensation can occur so the average cluster size is reduced. In embodiments, several other gases (shown as "Gas Source 2") can be added into the source chamber. For example, introducing helium can lead to a reduction of the cluster size while introducing oxygen or nitrogen can lead to generation of ceramic clusters or nanoparticles by reactive sputtering and ceramic coating on the polymer substrate. Nanocluster or nanoparticle deposition services are available, e.g., from Mantis Deposition Ltd., England (http://www.mantisdeposition.com) and the relevant techniques are further disclosed by Weber et al., Provisional Application No. 60/857,849, A. H. Kean et al., Mantis Deposition Ltd., NSTI Nano Tech 2006, Boston, May 7-11, 2006, in Y. Qiang et al., Surface and Coating Technology, 100-101, 27-32 (1998) and in Kraft et al., Surface and Coating Technology, 158-159, 131-135 (2002).

In embodiments, the ceramic or metal is adhered only on the abluminal surface of the stent. This construction may be accomplished by, e.g. coating the stent before forming the fenestrations, as described in e.g., Weber, U.S. Pat. No. 6,517,888. In other embodiments, the ceramic or metal is adhered only on abluminal and cut-face surfaces of the stent. This construction may be accomplished by, e.g., coating a stent containing a mandrel, which shields the luminal surfaces. Masks can be used to shield portions of the stent. In embodiments, the stent metal can be stainless steel, chrome, nickel, cobalt, tantalum, superelastic alloys such as nitinol, cobalt chromium, MP35N, and other metals. Suitable stent materials and stent designs are described in Heath '721, supra. Other suitable ceramics include metal oxides and nitrides, such as of iridium, zirconium, titanium, hafnium, niobium, tantalum, ruthenium, platinum and aluminum. The ceramic can be crystalline, partly crystalline or amorphous. The ceramic can be formed entirely of inorganic materials or a blend of inorganic and organic material (e.g. a polymer). In other embodiments, the morphologies described herein can be formed of metal. As discussed above, different ceramic materials can be provided in different regions of a stent. For example, different materials may be provided on different stent surfaces. A rougher, defined grain material may be provided on the abluminal surface to, e.g. enhance porosity or adhesion to the polymer while a smooth globular material can be provided on the adluminal surface to enhance endothelialization. In yet some embodiments, a material of a defined grain morphology may be provided first on the stent surface to, e.g. enhance adhesion of the polymer while a smooth globular material can be provided on top of the polymer to enhance endothelialization.

The ceramic material can also be selected for compatibility with a particular polymer coating to, e.g. enhance adhesion. For example, for a hydrophilic polymer, the surface chemistry of the ceramic is made more hydrophilic by e.g., increasing the oxygen content, which increases polar oxygen moieties, such as OH groups. Suitable drug eluting polymers may be hydrophilic or hydrophobic. Suitable polymers include, for example, polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics such as polystyrene and copolymers thereof with other vinyl monomers such as isobutylene, isoprene and butadiene, for example, styrene-isobutylene-styrene (SIBS), styrene-isoprene-styrene (SIS) copolymers, styrene-butadiene-styrene (SBS) copolymers, polyethylene oxides, glycosaminoglycans, polysaccharides, polyesters including polyethylene terephthalate, polybutylene succinate (PBS), and polybutylene suucinate adipate (PBSA), polyacrylamides, polyethers, polyether sulfone, polycarbonate, polyalkylenes including polypropylene, polyethylene and high molecular weight polyethylene, halogenerated polyalkylenes including polytetrafluoroethylene, natural and synthetic rubbers including polyisoprene, polybutadiene, polyisobutylene and copolymers thereof with other vinyl monomers such as styrene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers. Coatings from polymer dispersions such as polyurethane dispersions (BAYHDROL®, etc.) and acrylic latex dispersions are also within the scope of the present disclosure. The polymer may be a protein polymer, fibrin, collagen and derivatives thereof, polysaccharides such as celluloses, starches, dextrans, alginates and derivatives of these polysaccharides, an extracellular matrix component, hyaluronic acid, or another biologic agent or a suitable mixture of any of these, for example. U.S. Pat. No. 5,091,205 describes medical devices coated with one or more polyiocyanates such that the devices become instantly lubricious when exposed to body fluids. In embodiments, a suitable polymer is polyacrylic acid, available as HYDROPLUS®. (Boston Scientific Corporation, Natick, Mass.), and described in U.S. Pat. No. 5,091,205, the disclosure of which is hereby incorporated herein by reference. Another polymer can be a copolymer of polylactic acid and polycaprolactone. The polymer can be biostable or biodegradable. Suitable polymers are discussed in U.S. Publication No. 2006/0038027.

In embodiments, the polymer is capable of absorbing a substantial amount of drug solution. In embodiments, when applied as a coating on a medical device, the dry polymer is typically on the order of from about 1 to about 50 microns thick, preferably about 1 to 10 microns thick, and more preferably about 2 to 5 microns. In embodiments, very thin polymer coatings, e.g., of about 0.2-0.3 microns and much thicker coatings, e.g., more than 10 microns, are also possible. In some embodiments, multiple layers of polymer coating can be provided onto a medical device. Such multiple layers are of the same or different polymer materials. Such multiple layers can contain different drugs in each layer, or some of the multiple layers may not contain any drugs. Suitable DEP coating are further disclosed in U.S. Pat. Nos. 5,605,696 and 5,447,724. In certain embodiments, the polymer can only act as a membrane to regulate drug release. For example, drug particles can first be applied to the stent, then a layer of polymer can be applied on top of the drugs and between the drugs and the ceramic coating to function a first drug release regulating layer while the ceramic coating functions as a second drug release regulating layer.

The terms "therapeutic agent", "pharmaceutically active agent", "pharmaceutically active material", "pharmaceutically active ingredient", "drug" and other related terms may be used interchangeably herein and include, but are not limited to, small organic molecules, peptides, oligopeptides, proteins, nucleic acids, oligonucleotides, genetic therapeutic agents, non-genetic therapeutic agents, vectors for delivery of genetic therapeutic agents, cells, and therapeutic agents identified as candidates for vascular treatment regimens, for example, as agents that reduce or inhibit restenosis. By small organic molecule is meant an organic molecule having 50 or fewer carbon atoms, and fewer than 100 non-hydrogen atoms in total.

Exemplary non-genetic therapeutic agents for use in conjunction with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) alpha receptor antagonist (such as doxazosin, Tamsulosin) and beta receptor agonists (such as dobutamine, salmeterol), beta receptor antagonist (such as atenolol, metaprolol, butoxamine), angiotensin-II receptor antagonists (such as losartan, valsartan, irbesartan, candesartan and telmisartan), and antispasmodic drugs (such as oxybutynin chloride, flavoxate, tolterodine, hyoscyamine sulfate, diclomine), (u) bARKct inhibitors, (v) phospholamban inhibitors, (w) Serca 2 gene/protein, (x) immune response modifiers including aminoquizolines, for instance, imidazoquinolines such as resiquimod and imiquimod, and (y) human apolioproteins (e.g., AI, AII, AIII, AIV, AV, etc.).

Specific examples of non-genetic therapeutic agents include paclitaxel, (including particulate forms thereof, for instance, protein-bound paclitaxel particles such as albumin-bound paclitaxel nanoparticles, e.g., ABRAXANE), sirolimus, everolimus, tacrolimus, Epo D, dexamethasone, estadiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well a derivatives of the forgoing, among others.

Exemplary genetic therapeutic agents for use in conjunction with the present invention include anti-sense DNA and RNA as well as DNA coding for the various proteins (as well as the proteins themselves): (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Cells for use in conjunction with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and f-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin, macrolide antibiotics such as erythromycin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and trailast (bb) endothelialization facilitators such as VEGF and RGD peptide, and (cc) blood rheology modulators such as pentoxifylline.

Further additional therapeutic agents include immunosuppressents such as sirolimus and antibiotics such as macrolide antibiotics, evorolimus, and Tacrolimus for the practice of the present invention are also disclosed in U.S. Pat. No. 5,733, 925.

Where a therapeutic agent is included, a wide range of therapeutic agent loadings can be used in conjunction with the medical devices of the present invention, with the therapeutically effective amount being readily determined by those of ordinary skill in the art and ultimately depending, for example, upon the condition to be treated, the age, sex and condition of the patient, the nature of the therapeutic agent, the nature of the ceramic region(s), and/or the nature of the medical device, among other factors.

EXAMPLE

In a particular embodiment a 1% toluene solution of SIBS with 8.8 wt. % paclitaxel was sprayed onto a stainless steel stent with masks on its adluminal and cut-face surfaces until the thickness reached a desired value, e.g., 10 microns. The stent coated with DEP was then dried in air. The drug content of the dry DEP coating was about 8.8% by weight. Subsequently, the DEP-coated stent was mount in an Axplorer PLD system by Axyntec, Augsburg, Germany. An iridium (99.9 wt. %) target was ablated by a 248 nm laser of 10 ns pulse at an energy of 600 ml, base pressure of 0.8 mbar oxygen, and substrate temperature of 50 degrees of Celsius. The resultant IROX layer had a thickness of about 15 nm to 150 nm.

Figure 10:
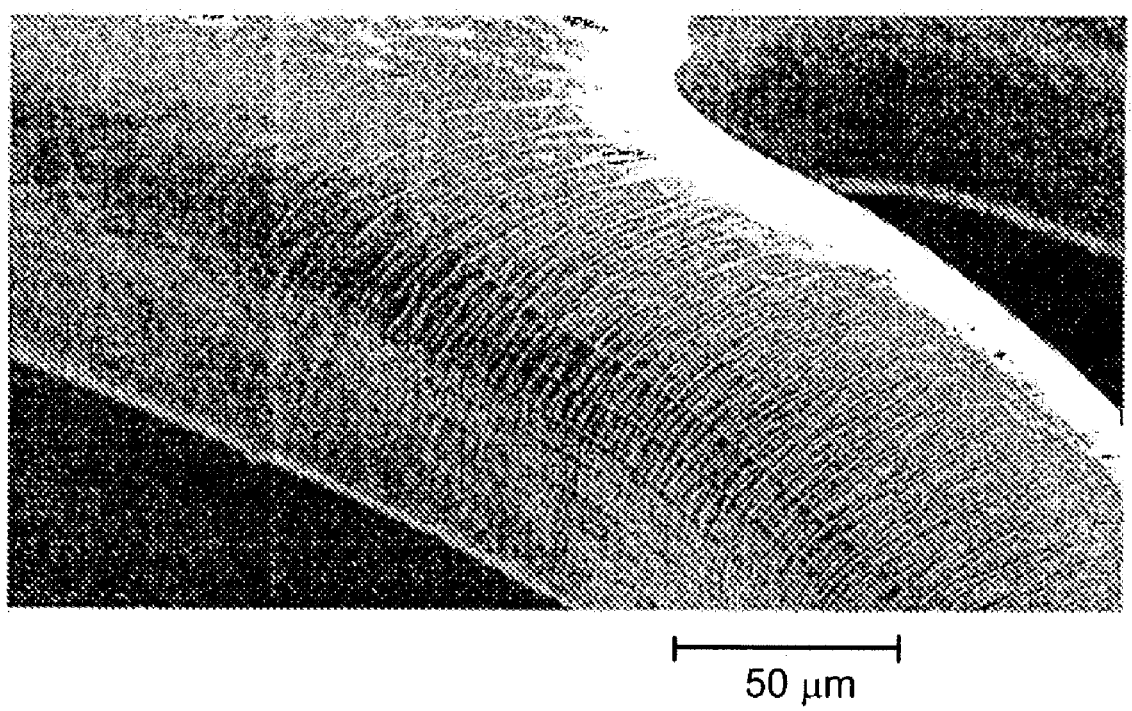
FIG. 10 is an FESEM image of a region of a stent.

Referring to FIG. 10, a field emission scanning electron microscopy ("FESEM") image of the surface of a strut of a stainless steel stent processed with the method disclosed in EXAMPLE is shown. As shown in FIG. 10, about 10-15 nm thick of IROX covers the stent surface, underneath which is about several microns thick of SIBS/paclitaxel ("PTX").

In further embodiments, the polymeric coating may incorporate magnetic particles, e.g., nanoparticles. The embodiments may have one or more additional following advantages, including that the release profile of a therapeutic agent from an endoprosthesis can be controlled through non-invasive means, e.g., a magnetic field. The magnetic field can be used to selectively agitate the particles, to modify drug release from the polymeric coating. Use of magnetic particles is described further in U.S. Provisional Application No. 60/845, 136, filed Sep. 15, 2006.

Any stent described herein can be dyed or rendered radiopaque by addition of, e.g., radiopaque materials such as barium sulfate, platinum or gold, or by coating with a radiopaque material. The stent can include (e.g., be manufactured from) metallic materials, e.g., biostable metallic materials such as stainless steel (e.g., 316L, BioDur® 108 (UNS S29108), and 304L stainless steel, and an alloy including stainless steel and 5-60% by weight of one or more radiopaque elements (e.g., Pt, Ir, Au, W) (PERSS®) as described in US-2003-0018380-A1, US-2002-0144757-A1, and US-2003-0077200-A1), Nitinol (a nickel-titanium alloy), cobalt alloys such as Elgiloy, L605 alloys, MP35N, titanium, titanium alloys (e.g., Ti-6Al-4V, Ti-50Ta, Ti-10Ir), platinum, platinum alloys, niobium, niobium alloys (e.g., Nb-1Zr) Co-28Cr-6Mo, tantalum, and tantalum alloys. Other examples of materials are described in commonly assigned U.S. application Ser. No. 10/672,891, filed Sep. 26, 2003; and U.S. application Ser. No. 11/035,316, filed Jan. 3, 2005. The stent can be formed of bioerodible metal such as magnesium, iron, calcium, aluminum, or their alloys. Other materials include elastic biocompatible metal such as a superelastic or pseudo-elastic metal alloy, as described, for example, in Schetsky, L. McDonald, "Shape Memory Alloys", Encyclopedia of Chemical Technology (3rd ed.), John Wiley & Sons, 1982, vol. 20. pp. 726-736; and commonly assigned U.S. application Ser. No. 10/346,487, filed Jan. 17, 2003.

The stents described herein can be configured for vascular, e.g. coronary and peripheral vasculature or non-vascular lumens. For example, they can be configured for use in the esophagus or the prostate. Other lumens include biliary lumens, hepatic lumens, pancreatic lumens, and urethral lumens.

The stent can be of a desired shape and size (e.g., coronary stents, aortic stents, peripheral vascular stents, gastrointestinal stents, urology stents, tracheal/bronchial stents, and neurology stents). Depending on the application, the stent can have a diameter of between, e.g., about 1 mm to about 46 mm. In certain embodiments, a coronary stent can have an expanded diameter of from about 2 mm to about 6 mm. In some embodiments, a peripheral stent can have an expanded diameter of from about 4 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm. The stent can be balloon-expandable, self-expandable, or a combination of both (e.g., U.S. Pat. No. 6,290,721). Other medical devices, particularly implantable devices can be formed, such as catheters, guide wires, and filters, having implants and electrodes.

A number of embodiments have been described in the disclosure. Nevertheless, it will be understood that various modifications may be made without departing from the spirit and scope of the disclosure. For example, referring back to FIG. 3, the first coating 25, e.g., a polymeric coating can be provided as well or only on the adluminal surface and/or cut-face surfaces; while the second coating, e.g., a porous ceramic coating, can be provided only on the abluminal surface or as well on the cut-face surfaces. Also for another example, a stent formed of a polymeric material (e.g., a biostable polymer such as polyurethane or a bioerodible polymer such as poly(lactic-co-glycolic acid)) can be coated with a similar construction on select surfaces as discussed above, e.g., a DEP or drug coating covered with a porous ceramic or metallic layer over the abluminal surface. In a particular example, in case of a bioerodible polymer stent, porous iron or magnesium can be the over coating. The bioerodible stent can also be covered with an initial porous ceramic or metallic underlayer (e.g., a bioerodible ceramic or metal, for example, calcium carbonate or iron), after which a DEP can be applied to select regions of the underlayer, which then is covered with a porous ceramic or metal over coating. Such an arrangement allows that the drug eluting process lasts longer then the stent erosion process: the drug elutes only through the over coating if the stent is still intact and the drug can elute both through the over coating and the underlayer once the stent is eroded.

All publications, patent applications, patents, and other references mentioned herein are incorporated by reference herein in their entirety.

Still other embodiments are in the following claims.

What is claimed is:

1. An endoprosthesis, comprising:
a first coating comprising a polymer, and
a second coating over the first coating formed of a porous ceramic,
wherein the porous ceramic has a smooth globular morphology to enhance endothelial cell growing over the second coating, the globular morphology having a series of shallow globular features and the globular features having a local maxima width of about 100 nm or less and a peak height of about 50 nm or less.

2. The endoprosthesis of claim 1, wherein the polymer includes a drug.

3. The endoprosthesis of claim 1, wherein the ceramic iridium oxide, titanium oxide, tantalum oxide, or niobium oxide.

4. The endoprosthesis of claim 1, wherein the first coating has a plurality of depressions.

5. The endoprosthesis of claim 1, wherein the second coating has pores with a pore diameter of about 1 nm to about 20 nm.

6. The endoprosthesis of claim 1, wherein the thickness of the second coating is about 10 to about 500 nm.

7. The endoprosthesis of claim 1, wherein the thickness of the first coating is about 0.1 to about 10 micron.

8. The endoprosthesis of claim 1, wherein the first coating contacts a surface of an endoprosthesis body.

9. The endoprosthesis of claim 8, wherein the endoprosthesis body is formed of a metal.

10. The endoprosthesis of claim 8, wherein the endoprosthesis body is formed of a polymer.

11. The endoprosthesis of claim 10, wherein the polymer is a bioerodible polymer.

12. The endoprosthesis of claim 10, wherein the polymer is a biostable polymer.

13. The endoprosthesis of claim 1, further comprising a third coating under the first coating, the third coating formed of a ceramic having a high roughness defined grain morphology.

14. The endoprosthesis of claim 1, wherein the globular morphology has a developed interfacial area ratio of between 8 and 15.

15. A method of forming an endoprosthesis, comprising:
forming a polymer coating on the endoprosthesis wherein the polymer coating comprises a drug, and
forming a layer of porous ceramic or metal over the drug-containing polymer coating, wherein the porous ceramic has a smooth globular morphology to enhance endothelial cell growing over the porous ceramic, the globular morphology having a series of shallow globular features and the globular features having a local maxima width of about 100 nm or less and a peak height of about 50 nm or less.

16. The method of claim 15, comprising forming the polymer coating by spraying a solution of a polymer and a drug to a surface of an endoprosthesis body.

17. The method of claim 15, comprising introducing the drug by coating, dipping, or spraying.

18. The method of claim 15, comprising forming the polymer coating by introducing a polymer by dipping, spraying, brushing, pressing, laminating, or pulsed laser deposition.

19. The method of claim 15 comprising introducing the drug by pulsed laser deposition.

20. The method of claim 15 comprising forming the porous ceramic layer by pulsed laser deposition.

21. The method of claim 15, further comprising forming depressions in the polymer coating by laser irradiation.

22. An endoprosthesis, comprising:
a first coating comprising a polymer;
a second coating over the first coating, the second coating being formed of a porous ceramic having a smooth globular morphology, the globular morphology having a series of shallow globular features and the globular features having a local maxima width of about 100 nm or less and a peak height of about 50 nm or less, and
a third coating under the first coating, the third coating being formed of a ceramic having a high roughness defined grain morphology.

* * * * *

UNITED STATES PATENT AND TRADEMARK OFFICE
CERTIFICATE OF CORRECTION

| | |
|---|---|
| PATENT NO. | : 7,981,150 B2 |
| APPLICATION NO. | : 11/860253 |
| DATED | : July 19, 2011 |
| INVENTOR(S) | : Scheuermann et al. |

It is certified that error appears in the above-identified patent and that said Letters Patent is hereby corrected as shown below:

1.) Cover Page, in section (57) Abstract: after "elution of", delete "drag" and insert --drug--.

2.) Column 18, in claim 3, line 1: after "ceramic", insert --is--.

Signed and Sealed this
Twenty-seventh Day of September, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,981,150 B2 | Page 1 of 1 |
| APPLICATION NO. | : 11/860253 | |
| DATED | : July 19, 2011 | |
| INVENTOR(S) | : Scheuermann et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 68 days.

Signed and Sealed this
Sixth Day of December, 2011

David J. Kappos
*Director of the United States Patent and Trademark Office*